United States Patent
Butora et al.

(10) Patent No.: US 10,428,106 B2
(45) Date of Patent: *Oct. 1, 2019

(54) PHOSPHATE REPLACEMENT MRNA CAP ANALOGS

(71) Applicant: ModernaTX, Inc., Cambridge, MA (US)

(72) Inventors: Gabor Butora, Martinsville, NJ (US); Matthew Stanton, Needham, MA (US); Thomas Steele, Upton, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/008,655

(22) Filed: Jun. 14, 2018

(65) Prior Publication Data

US 2018/0312535 A1 Nov. 1, 2018

Related U.S. Application Data

(63) Continuation of application No. 15/768,199, filed as application No. PCT/US2016/057384 on Oct. 17, 2016.

(60) Provisional application No. 62/242,845, filed on Oct. 16, 2015.

(51) Int. Cl.
*C07H 21/00* (2006.01)
*C07H 21/02* (2006.01)

(52) U.S. Cl.
CPC ............. *C07H 21/02* (2013.01); *C07H 21/00* (2013.01)

(58) Field of Classification Search
None
See application file for complete search history.

(56) References Cited

U.S. PATENT DOCUMENTS

| | | | |
|---|---|---|---|
| 5,861,501 A | 1/1999 | Benseler et al. | |
| 5,936,077 A | 8/1999 | Pfleiderer et al. | |
| 5,962,272 A | 10/1999 | Chenchik et al. | |
| 6,022,715 A | 2/2000 | Merenkova et al. | |
| 7,074,596 B2 | 7/2006 | Darzynkiewicz et al. | |
| 9,751,925 B2 * | 9/2017 | Hoge ................ | C07K 14/505 |
| 2003/0082768 A1 | 5/2003 | Baskerville et al. | |
| 2005/0059624 A1 | 3/2005 | Hoerr et al. | |
| 2005/0137155 A1 | 6/2005 | McSwiggen et al. | |
| 2008/0260706 A1 | 10/2008 | Rabinovich et al. | |
| 2009/0093433 A1 | 4/2009 | Woolf et al. | |
| 2009/0286852 A1 | 11/2009 | Kariko et al. | |
| 2010/0129877 A1 | 5/2010 | Sahin et al. | |
| 2010/0239608 A1 | 9/2010 | Von Der Mulbe et al. | |
| 2010/0261231 A1 | 10/2010 | Kore et al. | |
| 2010/0303851 A1 | 12/2010 | Hoerr et al. | |
| 2011/0077287 A1 | 3/2011 | Von Der Mulbe et al. | |
| 2011/0244026 A1 | 10/2011 | Guild et al. | |
| 2012/0053333 A1 | 3/2012 | Mauro et al. | |
| 2012/0195917 A1 | 8/2012 | Sahin et al. | |
| 2012/0195936 A1 | 8/2012 | Rudolph et al. | |
| 2012/0322865 A1 | 12/2012 | Rossi et al. | |
| 2013/0102655 A1 | 4/2013 | Kore et al. | |
| 2013/0183355 A1 | 7/2013 | Jain et al. | |
| 2013/0195867 A1 | 8/2013 | Hoerr et al. | |
| 2013/0195967 A1 | 8/2013 | Guild et al. | |
| 2013/0197068 A1 | 8/2013 | Kariko et al. | |
| 2014/0147454 A1 | 5/2014 | Chakraborty et al. | |
| 2016/0237108 A1 * | 8/2016 | Fraley .................. | C07H 19/067 |
| 2018/0291055 A1 * | 10/2018 | Butora .................. | C07H 21/02 |

FOREIGN PATENT DOCUMENTS

| | | | | |
|---|---|---|---|---|
| EP | 0194809 B1 | 3/1991 | | |
| EP | 1905844 A2 | 4/2008 | | |
| EP | 2377938 A1 | 10/2011 | | |
| EP | 2548960 A1 | 1/2013 | | |
| PL | 193592 B1 * | 2/2007 | ............. | C07H 21/02 |
| WO | WO 1999/014346 A2 | 3/1999 | | |
| WO | WO 2000/050586 A2 | 8/2000 | | |
| WO | WO 2007/024708 A2 | 3/2007 | | |
| WO | WO 2007/095976 A2 | 8/2007 | | |
| WO | WO 2007/120863 A2 | 10/2007 | | |
| WO | WO 2008/016473 A2 | 2/2008 | | |
| WO | WO 2008/052770 A2 | 5/2008 | | |
| WO | WO 2008/083949 A2 | 7/2008 | | |
| WO | WO 2008/157688 A2 | 12/2008 | | |
| WO | WO 2009/046738 A1 | 4/2009 | | |
| WO | WO 2009/046739 A1 | 4/2009 | | |
| WO | WO 2009/046974 A2 | 4/2009 | | |
| WO | WO 2009/046975 A1 | 4/2009 | | |
| WO | WO 2009/058911 A2 | 5/2009 | | |

(Continued)

OTHER PUBLICATIONS

[No Author Listed], "Messenger RNA", Internet: Wikipedia. Jun. 21, 2013, XP002699196, Retrieved from the Internet: URL: http://en.wikipedia.org/wiki/Messenger RNA.

Alberts, et al., Molecular Biology of the Cell, 3rd ed. Garland Publishing, Inc. New York, NY, 1994, pp. 368-369.

Aurup, H. et al., Translation of 2'-modified mRNA in vitro and in vivo. Nucleic Acids Res. Nov. 25, 1994; 22(23):4963-4968.

Banerjee, A.K., 5'-terminal cap structure in eukaryotic messenger ribonucleic acids. Microbiol Rev. Jun. 1980; 44 (2):175-205.

Bechler, K., Influence of capping and polyadenylation on mRNA expression and on antisense RNA mediated inhibition of gene expression. Biochem Biophys Res Commun. Dec. 8, 1997; 241(1):193-199.

(Continued)

*Primary Examiner* — Nancy J Leith
(74) *Attorney, Agent, or Firm* — Cooley LLP; Heidi A. Erlacher; Christine C. Pemberton

(57) ABSTRACT

The present disclosure relates to cap analogs, which can result in high levels of capping efficiency and transcription and improved translation efficiencies. The present disclosure also relates to methods useful for preparing cap analogs and using mRNA species containing such analogs, as well as kits containing the novel cap analogs.

20 Claims, 2 Drawing Sheets

Specification includes a Sequence Listing.

(56) References Cited

FOREIGN PATENT DOCUMENTS

| WO | WO 2009/095226 A2 | 8/2009 |
|---|---|---|
| WO | WO 2009/127230 A1 | 10/2009 |
| WO | WO 2009/149253 A2 | 12/2009 |
| WO | WO 2010/037408 A1 | 4/2010 |
| WO | WO 2010/088927 A1 | 8/2010 |
| WO | WO 2011/128444 A2 | 10/2011 |
| WO | WO 2011/130624 A2 | 10/2011 |
| WO | WO 2012/138453 A1 | 10/2012 |
| WO | WO 2013/052523 A1 | 4/2013 |
| WO | WO 2013/143698 A1 | 10/2013 |
| WO | WO 2014/071219 A1 | 5/2014 |
| WO | WO 2014/090246 A1 | 6/2014 |
| WO | WO 2014/160243 A1 | 10/2014 |
| WO | WO 2015/024667 A1 | 2/2015 |
| WO | WO 2017/066782 A1 | 4/2017 |
| WO | WO 2017/066789 A1 | 4/2017 |
| WO | WO 2017/066791 A1 | 4/2017 |
| WO | WO 2017/066793 A1 | 4/2017 |
| WO | WO 2017/066797 A1 | 4/2017 |

OTHER PUBLICATIONS

Bolukbasi, Mehmet Faith, et al., miR-1289 and "Zipcode"-like Sequence Enrich mRNAs in Microvesicles. Molecular Therapy-Nucleic Acids (2012) 1, e10: doi:10. 1038/mtna.2011.2, pp. 1-10.
Bouloy, M., et al., Both the 7-methyl and the 2'-O-methyl groups in the cap of mRNA strongly influence its ability to act as primer for influenza virus RNA transcription. Proc. Natl. Acad. Sci. USA, vol. 77, No. 7, pp. 3952-3956, Jul. 1980.
Carrington, J.C. et al., Cap-independent enhancement of translation by a plant potyvirus 5' nontranslated region. J Virol. Apr. 1990; 64(4): 1590-1597.
Cho, E.J. et al., mRNA capping enzyme is recruited to the transcription complex by phosphorylation of the RNA polymerase II carboxy-terminal domain. Genes Dev. Dec. 15, 1997; 11(24): 3319-3326.
Conry, R.M. et al., Characterization of a messenger RNA polynucleotide vaccine vector. Cancer Res. Apr. 1, 1995; 55 (7):1397-1400.
Cowling, "Regulation of mRNA cap methylation," Biochemical Journal, 425 (Pt 2): 295-302 (Jan. 15, 2010, online Dec. 23, 2009).
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Edery, I. et al., An efficient strategy to isolate full-length cDNAs based on an mRNA cap retention procedure (CAPture). Mol Cell Biol. 1995; 15(6): 3363-3371.
Epicentre Forum. Tools and Techniques for Genomics and RNA Research. 2007; 14(1): 1-24.
Gallie, D. R. The 5'-leader of tobacco mosaic virus promotes translation through enhanced recruitment of eIF4F. Nuc Acids Res. 2002; 30(15): 3401-3411.
Gallie, D.R., A tale of two termini: a functional interaction between the termini of an mRNA is a prerequisite for efficient translation initiation. Gene. Aug. 17, 1998; 216(1):1-11.
Gallie, D.R., The cap and poly(A) tail function synergistically to regulate mRNA translational efficiency. Genes Dev. Nov. 1991; 5(11):2108-2116.
Gao, M. et al., A novel mRNA-decapping activity in HeLa cytoplasmic extracts is regulated by Au-rich elements. EMBO J. Mar. 1, 2001; 20(5):1134-1143.
Grosjean, H., et al. Fine-Tuning of RNA Functions by Modification and Editing. Topics in Current Genetics, vol. 12, 2005, XXiV, p. 442.
Grosjean, H., Modification and editing of RNA: historical overview and important facts to remember. Topics Curr Gen. Jan. 2005; 12: 1-22.
Grosjean, H., Nucleic Acids Are Not Boring Long Polymers of Only Four Types of Nucleotides: A Guided Tour. Chapter 1. Landes Bioscience. 2009. pp. 1-18.
Grudzien, E. et al., Novel cap analogs for in vitro synthesis of mRNAs with high translational efficiency. RNA. Sep. 2004; 10(9): 1479-87.
Grudzien-Nogalska, E. et al., Phosphorothioate cap analogs stabilize mRNA and increase translational efficiency in mammalian cells. RNA. Oct. 2007;13(10):1745-1755. Epub Aug. 24, 2007.
Holcik, M. et al., Four highly stable eukaryotic mRNAs assemble 3' untranslated region RNA-protein complexes sharing cis and trans components. Proc Natl Acad Sci USA. Mar. 18, 1997; 94(6):2410-2414.
Hornung, V. et al., 5'-triphosphate RNA is the ligand for RIG-I. Science. Nov. 10, 2006; 314(5801): 994-997.
Jemielity, J. et al., Novel "anti-reverse" cap analogs with superior translational properties. RNA. Sep. 2003; 9 (9):1108-1122.
Keegan, Liam P. et al., The Many Roles of an RNA Editor, Nature Reviews, Genetics, Nov. 2001, vol. 2, pp. 869-878.
Kore, Anilkumar R., et al. Synthesis and biological validation of N7-(4-chlorophenoxyethyl) substituted dinucleotide cap analogs for mRNA translation. Bioorganic & Medicinal Chemistry 21 (2013), pp. 4570-4574.
Kozak, Marilyn, Regulation of translation via mRNA structure in prokaryotes and eukaryotes, Gene 361 (2005), pp. 13-37.
Kudla, G. et al., High guanine and cytosine content increases mRNA levels in mammalian cells. PLoS Biol. Jun. 2006;4(6):e180., 0933-0942 Epub May 23, 2006.
Kuhn, A.N., et al., mRNA as a versatile tool for exogenous protein expression. Current Gene Therapy. Oct. 2012; 12 (5): 347-361.
Lewis, J.D. et al., The influence of 5' and 3' end structures on pre-mRNA metabolism. J Cell Sci Suppl. 19, 1995;19:13-9.
Li, Junjie, et al.; Methylation Protects miRNAs and siRNAs from a 3'-End Uridylation Activity in *Arabidopsis*, Current Biology, 2005, vol. 15, pp. 1501-1507.
Iwase, Reiko et al., Molecular design of a eukaryotic messenger RNA and its chemical synthesis, Nucleic Acids Research, 1992, vol. 20, No. 7, pp. 1643-1648.
Mignone, F. et al., Untranslated regions of mRNAs. Genome Biol. 2002; 3(3): 1-10. Epub Feb. 28, 2002. pp. 1-10.
Myette, J.R. et al., Domain structure of the vaccinia virus mRNA capping enzyme. Expression in *Escherichia coli* of a subdomain possessing the RNA 5'-triphosphatase and guanylyltransferase activities and a kinetic comparison to the full-size enzyme. J Biol Chem. May 17, 1996; 271(20):11936-11944.
Nagata, S., Synthesis and Biological Activity of Artificial mRNA Prepared with Novel Phosphorylating Reagents, Nucleic Acids Research, 2010, vol. 38, No. 21, pp. 7845-7857. (published online Jul. 26, 2010).
Nielsen, Da et al., Preparation of capped RNA transcripts using T7 RNA polymerase. Nucleic Acids Res. Jul. 25, 1986;14(14):5936.
Norbury, C. J., Cytoplasmic RNA: A Case of the Tail Wagging The Dog, Nature Reviews, Molecular Cell Biology, 2013, Advanced Online Publication Aug. 29, 2013, pp. 1-10.
Preiss, T. et al., Dual function of the messenger RNA cap structure in poly(A)-tail-promoted translation in yeast. Nature. Apr. 2, 1998;392(6675):516-520.
Rajagopalan, Le. et al., Turnover and translation of in vitro synthesized messenger RNAs in transfected, normal cells. J Biol Chem. Aug. 16, 1996;271(33):19871-19876.
Régnier, P. et al., Degradation of mRNA in bacteria: emergence of ubiquitous features. BioEssays. Mar. 2000;22 (3):235-244.
Schmidt, W.M. et al., CapSelect: a highly sensitive method for 5' CAP-dependent enrichment of full-length cDNA in PCR-mediated analysis of mRNAs. Nucleic Acids Res. Nov. 1, 1999;27(21):e31, 4 pages.
Shuman, S. et al., Purification and characterization of a GTP-pyrophosphate exchange activity from vaccinia virions. Association of the GTP-pyrophosphate exchange activity with vaccinia mRNA guanylyltransferase. RNA (guanine-7-) methyltransferase complex (capping enzyme). J Biol Chem. Dec. 10, 1980;255(23):11588-11598.
Shuman, S., Capping enzyme in eukaryotic mRNA synthesis. Prog Nucleic Acid Res Mol Biol. 1995;50:101-129.
Shuman, S., Structure, mechanism, and evolution of the mRNA capping apparatus. Prog Nucleic Acid Res Mol Biol. 2001;66:1-40.

(56) References Cited

OTHER PUBLICATIONS

Stepinski, J. et al., Synthesis and properties of mRNAs containing the novel "anti-reverse" cap analogs 7-methyl(3'-O-methyl)GpppG and 7-methyl (3'-deoxy)GpppG. RNA. Oct. 2001;7(10):1486-1495.
Strong, T.V. et al., Incorporation of beta-globin untranslated regions into a Sindbis virus vector for augmentation of heterologous mRNA expression. Gene Ther. Jun. 1997;4(6):624-627.
Tourriere, H. et al., mRNA degradation machines in eukaryotic cells. Biochimie. Aug. 2002;84(8):821-837.
Wang, S.P. et al., Phylogeny of mRNA capping enzymes. Proc Natl Acad Sci USA. Sep. 2, 1997;94(18):9573-9578.
Warren, L. et al. Highly efficient reprogramming to pluripotency and directed differentiation of human cells with synthetic modified mRNA. Cell Stem Cell. Nov. 5, 2010;7(5):618-630.
Wickens, M. et al., A PUF family portrait: 3' UTR regulation as a way of life. Trends Genet. Mar. 2002;18(3):150-157.
Yamamoto et al., Current prospects for mRNA gene delivery, European Journal of Pharmaceutics and Biopharmaceutics 71 (2009) 484-489.
Yamashita, A. et al., Concerted action of poly(A) nucleases and decapping enzyme in mammalian mRNA turnover. Nat Struct Mol Biol. Dec. 2005;12(12):1054-1063. Epub Nov. 13, 2005.
Fukuoka et al., "One-Pot Synthesis of α, γ-Dinucleoside 5'-Triphosphates, G5'pppG and A5'-pppA, Using S, S'-Bis(4-chlorophenyl) phosphorodithioate," Chemistry Letters, pp. 499-502, 1994.
Guranowski et al., "Adenosine-5'-O-phosphorylated and adenosine-5'-D-phosphorothioylated polyols as strong inhibitors of (symmetrical) and (asymmetrical) dinucleoside tetraphosphatases," Biochem. J., (2003) 373, 635-640.
Holstein, "Bioorthogonal site-specific labeling of the 5'-cap structure in eukaryotic mRNAs," Chem. Commun., 2014, 50, 4478-4481.
Holý et al., "Preparation and Properties of some N-(2-hydroxyethyl) Derivatives of Ribonucleosides and Nucleotides," Collection of Czechoslovak Chemical Communications, vol. 36, 1971, 19 pages.
Ikehara et al., "Conformation of Purine Nucleoside Pyrophophates as Studied by Circular Dichroism," Biochemistry, vol. 11, No. 5, 1972, pp. 836-842.
Ishikawa et al., "Preparation of eukaryotic mRNA having differently methylated adenosine at the 5'-terminus and the effect of the methyl group in translation," Nucleic Acids Symposium Series No. 53, 129-130, Sep. 27, 2009.
Jemielity et al., "Synthesis of Novel mRNA 5' Cap-Analogues: Dinucleoside P1, P3-Tri-, P1, P4-Tetra-, and P1, P5-Pentaphosphates," Nucleosides, Nucleotides and Nucleic Acids, 22:5-8, pp. 691-694, 2003.
Kore et al., "Locked Nucleic Acid (LNA)-Modified Dinucleotide mRNA Cap Analogue: Synthesis, Enzymatic Incorporation, and Utilization," J. Am. Chem. Soc., 2009, 131, 6364-6365 (Published on Web Apr. 22, 2009).
Kowalska et al., "Synthesis and Properties of mRNA Cap Analogs Containing Phosphorothiuate Moiety in 5',5'-Triphosphate Chain," Nucleosides, Nucleotides and Nucleic Acids, 24 (5-7):595-600, (2005).
Lewdorowicz et al., "Synthesis of Leishmania Cap-4 Intermediates, Cap-2 and Cap-3," Nucleosides, Nucleotides and Nucleic Acids, 26:1339-1348, 2007.
Moreau et al., "Synthesis of cyclic adenosine 5'-diphosphate ribose analogues: a C2' endo/syn "southern" ribose conformation underlies activity at the sea urchin cADPR receptor," Org. Biomol. Chem., 2011, 9, 278-290.
Niedzwiecka et al., "Biophysical Studies of eIF4E Cap-binding Protein: Recognition of mRNA 5' Cap Structure and Synthetic Fragments of eIF4G and 4E-BP1 Proteins," J. Mol. Biol. (2002) 319, 615-635.
Peyrane et al., "High-yield production of short GpppA- and 7MeGpppA-capped RNAs and HPLC-monitoring of methyltransfer reactions at the guanine-N7 and adenosine-2'O positions," Nucleic Acids Research, 2007, vol. 35, No. 4 e26, 11 pages.

Sawai et al., "Synthesis and Reactions of Nucleoside 5'-Diphosphate Imidazolide. A Nonenzymatic Capping Agent for 5'-Monophosphorylated Oligoribonucleotides in Aqueous Solution," J. Org. Chem. 1999, 64, 5836-5840.
Smith et al., "A Unique Class of Compound, Guanosine-Nucleoside Tetraphosphate G(5')pppp(5')N, Synthesized during the in Vitro Transcription of Cytoplasmic Polyhedrosis Virus of Bombyxmori," The Journal of Biological Chemistry, vol. 257, No. 1, Issue of Jan. 10, 1982, pp. 485-494.
Strenkowska et al., "Towards mRNA with superior translational activity: synthesis and properties of ARCA tetraphosphates with single phosphorothioate modifications," New J Chem., Jan. 2010, 34(5): 993-1007.
Su et al., "Translation, stability, and resistance to decapping of mRNAs containing caps substituted in the triphosphate chain with BH3, Se, and NH," RNA, 2011 17: 978-988, originally published online Mar. 29, 2011.
Tahara et al., "Effect of Eukaryotic Initiation Factor 4F on AUG Selection in a Bicistronic mRNA," The Journal of Biological Chemistry, vol. 266, No. 6, Issue of Feb. 25, 1991, pp. 3594-3601.
Yamada et al., "Cyclic ADP-Ribose via Stereoselective Cyclization of β-NAD," J. Am. Chem. Soc., 1994, 116, 10787-10788.
Yamakawa et al., "Priming of reovirus transcription by GppppG and formation of CpG(5')pppp(5')GpC (mRNA initiation)," Proc. Natl. Acad. Sci. USA, vol. 79, pp. 6142-6146, Oct. 1982.
Yoffe et al., "Binding Specificities and Potential Roles of Isoforms of Eukaryotic Initiation Factor 4E in Leishmania," Eukaryotic Cell, Dec. 2006, pp. 1969-1979, vol. 5, No. 12.
Zhang et al., "Novel Enzymatic Cyclizations of Pyridine Nucleotide Analogs: Cyclic-GDP-Ribose and Cyclic-HDP-Ribose," Tetrahedron Letters, vol. 36, No. 51, pp. 9289-9292, 1995.
Beier et al., "Nucleotides, Part LXI, Phthaloyl Strategy: A New Concept of Oligonucleotide Synthesis," Helvetica Chimica Acta, vol. 82, 1999, pp. 633-644.
Cai et al., "Quantitative Assessment of mRNA Cap Analogues as Inhibitors of in Vitro Translation," Biochemistry, 1999, 38, pp. 8538-8547 (published on Web Jun. 11, 1999).
Darzynkiewicz et al, "Inhibition of Eukaryotic Translation by Analogues of Messenger RNA 5'-Cap: Chemical and Biological Consequences of 5'-Phosphate Modifications of 7-Methylguanosine 5'-Monophosphate," Biochemistry ,1987, 26, pp. 4372-4380.
Franchetti et al., "Synthesis, conformational analysis, and biological activity of new analogues of thiazole-4-carboxamide adenine dinucleotide (TAD) as IMP dehydrogenase inhibitors," Bioorganic & Medicinal Chemistry 13 (2005) pp. 2045-2053 (Available online Jan. 23, 2005).
Holstein et al., "Enzymatic modification of 5'-capped RNA with a 4-vinylbenzyl group provides a platform for photoclick and inverse electron-demand Diels-Alder reaction," Chem. Sci., 2015, 6, pp. 1362-1369.
Muttach et al., "A Biocatalytic Cascade for Versatile One-Pot Modification of mRNA Starting from Methionine Analogues," Angew. Chem. Int. Ed. 2016, 55, pp. 1917-1920.
Piecyk et al., "How to find the optimal partner-studies of snurportin 1 interactions with U snRNA 5' TMG-cap analogues containing modified 2-amino group of 7-methylguanosine," Bioorganic & Medicinal Chemistry 23 (2015) pp. 4660-4668 (Available online Jun. 6, 2015).
Piecyk et al., "Triazole-containing monophosphate mRNA cap analogs as effective translation inhibitors," RNA, 2014, vol. 20, No. 10, pp. 1539-1547.
Schulz et al., "A Chemo-Enzymatic Approach for Site-Specific Modification of the RNA Cap," Angew. Chem. Int. Ed. 2013, 52, pp. 7874-7878.
Stachelska et al., "Kinetics of the Imidazolium Ring-Opening of mRNA 5'-cap Analogs in Aqueous Alkali," Collect. Czech. Chem. Commun. 2006, vol. 71, No. 4, pp. 567-578.
Veliath et al., "Synthesis of Capped RNA using a DMT Group as a Purification Handle," Nucleosides, Nucleotides and Nucleic Acids, 2014 33:1, pp. 40-52.
Worch et al., "Specificity of recognition of mRNA 5' cap by human nuclear cap-binding complex," RNA 2005 11 : pp. 1355-1363.

(56) References Cited

OTHER PUBLICATIONS

Zuberek et al., "Binding Studies of Eukaryotic Initiation Factor eIF4E with Novel mRNA Dinucleotide Cap Analogues," Nucleosides, Nucleotides and Nucleic Acids, vol. 22, No. 5-8, Oct. 2003, pp. 1703-1706.

\* cited by examiner

PHOSPHATE REPLACEMENT MRNA CAP ANALOGS

RELATED APPLICATIONS

This application is a continuation application of U.S. application Ser. No. 15/768,199, filed Apr. 13, 2018, which is a U.S. National Phase application, filed under 35 U.S.C. § 371, of International Application No. PCT/US2016/057384, filed Oct. 17, 2016, which claims priority to, and the benefit of, U.S. Provisional Application No. 62/242,845, filed Oct. 16, 2015, the entire contents of which are incorporated herein by reference in their entireties.

INCORPORATION-BY-REFERENCE OF SEQUENCE LISTING

The contents of the text file named "MRNA008C01SL.txt", which was created on Jul. 16, 2018, and is 764 bytes in size, are incorporated herein by reference in its entirety.

BACKGROUND

Expression of the genetic information coded by a sequence of nucleotides in deoxyribonucleic acid (DNA) requires a biosynthesis of a complementary messenger ribonucleic acid (mRNA). This transcription event, which takes place in the nucleus of eukaryotic cells, is followed by translocation of the mRNA into the cytoplasm, where it is loaded into ribosomes by a complex and highly regulated process. Here the nucleotide sequence, presented as a series of three-nucleotide codons is translated into a corresponding sequence of amino acids ultimately producing the protein corresponding to the original genetic code.

Exogenous mRNA introduced to the cytoplasm can be in principle accepted by the ribosomal machinery (see, e.g., Warren et al., Highly Efficient Reprogramming to Pluripotency and Directed Differentiation of Human Cells with Synthetic Modified mRNA, Cell Stem Cell (2010)). If the mRNA codes for an excreted protein, the modified or exogenous mRNA can direct the body's cellular machinery to produce a protein of interest, from native proteins to antibodies and other entirely novel protein constructs that can have therapeutic activity inside and outside of cells.

There are difficulties with prior methodologies for effecting protein expression. There is a need in the art for biological modalities to address the modulation of intracellular translation of polynucleotides.

SUMMARY

The present disclosure provides mRNA cap analogs and methods of making and using them. The present disclosure also provides mRNA containing the cap analogs.

In one aspect, the present disclosure features a compound of formula (I) below or a stereoisomer, tautomer or salt thereof:

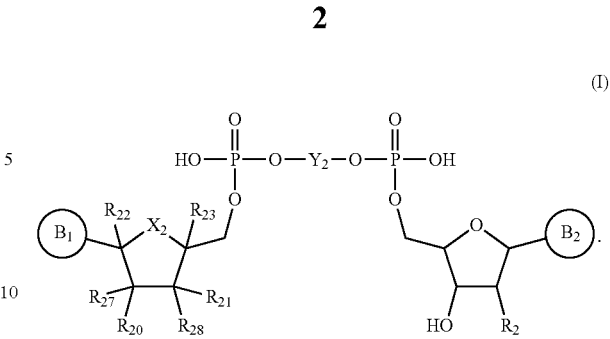

(I)

In formula (I) above,
ring $B_1$ is a modified Guanine;
ring $B_2$ is a nucleobase or a modified nucleobase;
$X_2$ is O, $S(O)_p$, $NR_{24}$ or $CR_{25}R_{26}$ in which p is 0, 1, or 2;
$Y_2$ is —$(CR_{40}R_{41})_u$-$Q_0$-$(CR_{42}R_{43})_v$—, in which $Q_0$ is a bond, O, $S(O)_r$, $NR_{44}$, or $CR_{45}R_{46}$, r is 0, 1, or 2, and each of u and v independently is 1, 2, 3 or 4;
$R_2$ is halo, LNA, or $OR_3$;
$R_3$ is H, $C_1$-$C_6$ alkyl, $C_2$-$C_6$ alkenyl, or $C_2$-$C_6$ alkynyl and $R_3$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;
each of $R_{20}$, $R_{21}$, $R_{22}$, and $R_{23}$ independently is -$Q_3$-$T_3$, in which $Q_3$ is a bond or $C_1$-$C_3$ alkyl linker optionally substituted with one or more of halo, cyano, OH and $C_1$-$C_6$ alkoxy, and $T_3$ is H, halo, OH, $NH_2$, cyano, $NO_2$, $N_3$, $R_{S3}$, or $OR_3$, in which $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, NHC(O)—$C_1$-$C_6$ alkyl, mono-$C_1$-$C_6$ alkylamino, di-$C_1$-$C_6$ alkylamino, 4 to 12-membered heterocycloalkyl, or 5- or 6-membered heteroaryl, and $R_{S3}$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;
each of $R_{24}$, $R_{25}$, and $R_{26}$ independently is H or $C_1$-$C_6$ alkyl;
each of $R_{27}$ and $R_{28}$ independently is H or $OR_{29}$; or $R_{27}$ and $R_{28}$ together form O—$R_{30}$—O;
each $R_{29}$ independently is H, $C_1$-$C_6$ alkyl, $C_2$-$C_6$ alkenyl, or $C_2$-$C_6$ alkynyl and $R_{29}$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;
$R_{30}$ is $C_1$-$C_6$ alkylene optionally substituted with one or more of halo, OH and $C_1$-$C_6$ alkoxyl;
each of $R_{40}$, $R_{41}$, $R_{42}$, and $R_{43}$ independently is H, halo, OH, cyano, $N_3$, OP(O)$R_{47}R_{48}$, or $C_1$-$C_6$ alkyl optionally substituted with one or more OP(O)$R_{47}R_{48}$, or one $R_{41}$ and one $R_{43}$, together with the carbon atoms to which they are attached and $Q_0$, form $C_4$-$C_{10}$ cycloalkyl, 4- to 14-membered heterocycloalkyl, $C_6$-$C_{10}$ aryl, or 5- to 14-membered heteroaryl, and each of the cycloalkyl, heterocycloalkyl, phenyl, or 5- to 6-membered heteroaryl is optionally substituted with one or more of OH, halo, cyano, $N_3$, oxo, OP(O)$R_{47}R_{48}$, $C_1$-$C_6$ alkyl, $C_1$-$C_6$ haloalkyl, COOH, C(O)O—$C_1$-$C_6$ alkyl, $C_1$-$C_6$ alkoxyl, $C_1$-$C_6$ haloalkoxyl, amino, mono-$C_1$-$C_6$ alkylamino, and di-$C_1$-$C_6$ alkylamino;
$R_{44}$ is H, $C_1$-$C_6$ alkyl, or an amine protecting group;
each of $R_{45}$ and $R_{46}$ independently is H, OP(O)$R_{47}R_{48}$, or $C_1$-$C_6$ alkyl optionally substituted with one or more OP(O)$R_{47}R_{48}$, and each of $R_{47}$ and $R_{48}$, independently is H, halo, $C_1$-$C_6$ alkyl, OH, SH, SeH, or $BH_3^-$.

The present disclosure also provides an RNA molecule (e.g., mRNA) whose 5' end contains a compound of formula (I).

Also provided herein is a kit for capping an RNA transcript. The kit includes a compound of formula (I) and an RNA polymerase. The kit may also include one or more of nucleotides, ribonuclease inhibitor, an enzyme buffer, and a nucleotide buffer.

In yet another aspect, the present disclosure provides methods of synthesizing the compound of formula (I).

In still another aspect, the present disclosure provides methods of synthesizing an RNA molecule (e.g., mRNA) in vitro. The method can include reacting unmodified or modified ATP, unmodified or modified CTP, unmodified or modified UTP, unmodified or modified GTP, a compound of formula (I) or a stereoisomer, tautomer or salt thereof, and a polynucleotide template; in the presence an RNA polymerase; under a condition conducive to transcription by the RNA polymerase of the polynucleotide template into one or more RNA copies; whereby at least some of the RNA copies incorporate the compound of formula (I) or a stereoisomer, tautomer or salt thereof to make an RNA molecule (e.g., mRNA).

In yet another aspect, the present disclosure provides a compound (e.g., a cap analog) or a polynucleotide containing the cap analog having an improved eIF4E binding affinity, enhanced resistance to degradation, or both, as compared to, e.g., natural mRNA caps and natural mRNAs.

Further, the compounds or methods described herein can be used for research (e.g., studying interaction of in vitro RNA transcript with certain enzymes) and other non-therapeutic purposes.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

BRIEF DESCRIPTION OF THE FIGURES

FIG. 2 is a histogram of hEPO levels measured after 3 hours of a cell free translation assay using mRNAs carrying different cap analogs, comparing the hEPO levels normalized for % capping obtained using an mRNA carrying Compound 7 to that of an mRNA carrying a triphosphate cap ("Standard" in FIG. 2, with a chemical structure of

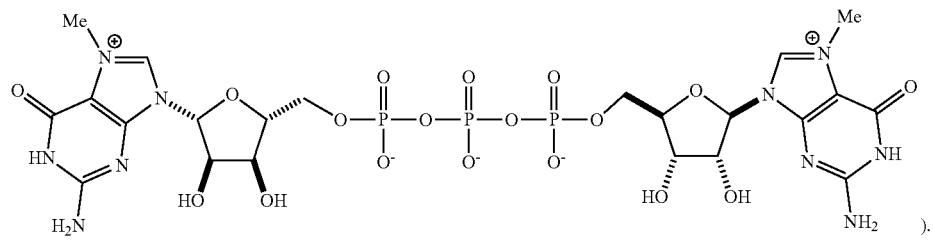

Figure 1:
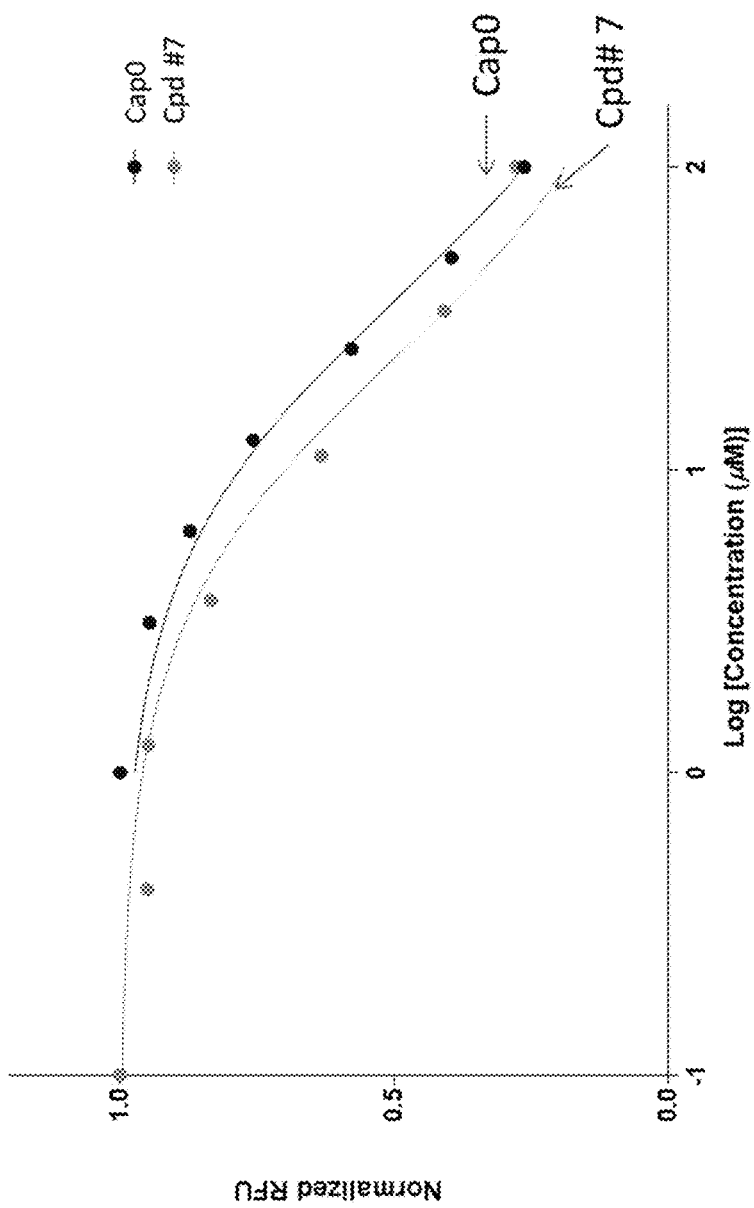
FIG. 1 is a plot of normalized relative fluorescence units (RFU) vs. the concentrations of the cap analogs tested from a cell free translation assay.
Figure 2:
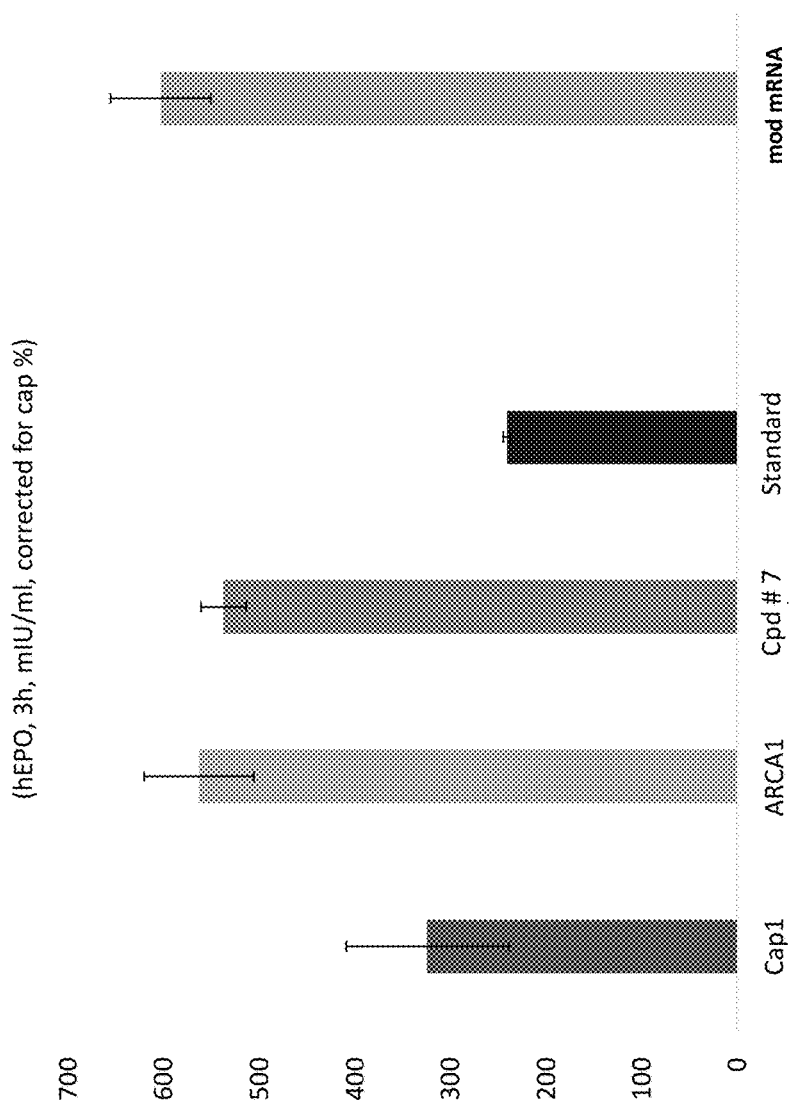

).

The Compound 7-cap-carrying mRNA shows superior expression (comparable to that of ARCA1) in a HeLa-derived cell free system, when compared to the triphosphate analog and/or Cap1. In this Figure, "mod mRNA" refers to a modified mRNA comprising N1-methyl pseudouridine, which replaces each uridine in the RNA sequence.

DETAILED DESCRIPTION

The present disclosure provides novel mRNA cap analogs, synthetic methods for making these cap analogs, and uses thereof. The present disclosure also provides new RNA molecules (e.g., mRNAs) incorporating the cap analogs disclosed herein which impart properties that are advantageous to therapeutic development.

The mRNA consists of an open reading frame (ORF) flanked by the 5'- and 3'-untranslated region (5'UTR, 3'UTR), a poly-adenosine monophosphate tail (polyA) and an inverted N7-methylguanosine containing cap structure. It is both chemically and enzymatically less stable than the corresponding DNA, hence the protein production subsequent to the ribosomal recruitment of the mRNA is temporary. In addition, the mRNA must be present in a so-called "closed loop" conformation for production of the target protein. While part of the active closed-loop conformation, the mRNA makes contact with the ribosomal machinery through the cap that binds to the eukaryotic initiation factor 4E (eIF4E) and the polyA tail attached through the polyA-binding protein (PABP). The eIF4E and PABP are connected through a skeletal protein eIF4G closing the active loop. Disruption of the mRNA circularized form leads to cessation of protein production and eventually enzymatic degradation of the mRNA itself chiefly by action of the de-capping enzyme system DCP1/2 and or through a poly-A ribonuclease (PARN) mediated de-adenylation. See, e.g., Richard J. Jackson et al., "The mechanism of eukaryotic translation initiation and principles of its regulation", *Molecular Cell Biology*, vol. 110, 113-127, 2010.

The cap-structure is a crucial feature of all eukaryotic mRNAs. It is recognized by the ribosomal complex through the eukaryotic initiation factor 4E (eIF4E). mRNAs lacking the 5'-cap terminus are not recognized by the translational machinery and are incapable of producing the target protein (see, e.g., Colin Echeverria Aitken, Jon R Lorsch: "A mechanistic overview of translation initiation in eukaryotes", *Nature Structural and Molecular Biology*, vol. 16, no. 6, 568-576, 2012.)

The crude messenger RNA produced during the transcription process ("primary transcript") is terminated by a 5'-triphosphate, which is converted to the respective 5'-diphosphate by the action of the enzyme RNA-triphosphatase. Then a guanylyl-transferase attaches the terminal inverted guanosine monophosphate to the 5'-terminus, and an N7MTase-mediated N7-methylation of the terminal, inverted guanosine, completes the capping process.

The 5'-cap structure is vulnerable to enzymatic degradation, which is part of the regulation mechanism controlling protein expression. According to this the enzymatic system DCP1/2 performs a pyrophosphate hydrolysis between the second and the third phosphate groups of the cap structure, removing the N7-methylated guanosine diphosphate moiety leaving behind an mRNA terminated in a 5'-monophosphate group. This in turn is quite vulnerable to exonuclease cleavage and will lead to rapid decay of the remaining oligomer. See, e.g., R. Parker, H. Song: "The Enzymes and Control of Eukaryotic Turnover", *Nature Structural & Molecular Biology*, vol. 11, 121-127, 2004.

High resolution X-ray crystallographic data of the eukaryotic initiation factor 4E (eIF4E) co-crystallized with P1-N7-methylguanosine-P3-adenosine-5',5'-triphosphate (N7GpppA) suggests a close molecular interaction between the terminal purine and the triphosphate moiety on one hand and the receptor surface on the other. See, e.g., Koji Tomoo, et al., "Crystal structures of 7-methylguanosine 5'-triphosphate (m(7)GTP)- and P(1)-7-methylguanosine-P(3)-adenosine-5',5'-triphosphate (m(7)GpppA)-bound human full-length eukaryotic initiation factor 4E: biological importance of the C-terminal flexible region.", *Biochem. J.* 362(Pt 3): 539-544, 2002. The terminal guanine is sandwiched between two aromatic side chains of TRP56 and TRP102 and this 7i-stacking interaction is further stabilized by two hydrogen bonds between the N7-guanine NH hydrogens and GLU103. The first two phosphate groups are interacting with basic residues of ARG112 and ARG157 as well as LYS 162 either directly or through water mediated hydrogen bonds. The third phosphate group forms a hydrogen bond with the basic residue of ARG112. In short, the high resolution x-ray crystallographic data suggests that the both the guanine and the triphosphate make direct contact with the protein and contribute to the binding efficiency of capped mRNAs.

The triphosphate moiety of the eukaryotic cap structure plays an important role in binding to the eIF4E as well as the stability of the mRNA. See, e.g., Anna Niedzwiecka et al., "Biophysical Studies of eIF4E Cap-binding Protein: Recognition of mRNA 50 Cap Structure and Synthetic Fragments of eIF4G and 4E-BP1 Proteins.", *Journal of Molecular Biology*, 319, 615-635, 2002. In addition, a DCP1/2-mediated hydrolysis of the pyrophosphate bond is the chief de-capping mechanism. See, e.g., Ewa Grudzien et al., "RNA: Structure, Metabolism, and Catalysis: Differential Inhibition of mRNA Degradation Pathways by Novel Cap Analogs.", *Journal of Biological Chemistry*, 281:1857-1867, 2006. Accordingly, the present disclosure is based, at least in part, on the assumption that replacement of the central phosphate with hydrophilic groups will be capable of maintaining the affinity to the binding pocket. Without wishing to be bound by theory, replacement of this phosphate with non-phosphate bridges could decrease the overall electrophilicity of the pyrophosphate grouping present in triphosphates, and since de-capping requires a nucleophilic attack of an enzyme-guided water molecule on the γ-phosphate, this in turn will result in cap structures resistant to enzymatic hydrolysis. The internucleoside distance can be tuned by the choice of appropriately sized moiety replacing the central triphosphate, such as glycols (e.g., diethylene- or triethylene-glycols). In addition to the distance, the overall special orientation of the two nucleosides can be altered by inclusion of cyclic structures such as cyclohexane-1,3-diol. Presence of hydrophilic groups such as that of a sulfoxide (SO), sulfone ($SO_2$) or even a phosphate can facilitate interaction with the polar groups lining the eIF4E binding pocket, while maintaining chemical and enzymatic stability. These chemical modifications will have an impact on cap's binding affinity to the eIF4E. In addition to altered binding behavior, these chemical modifications will affect the affinity of these caps towards the DCP1/2 enzyme system, and potentially improve stability of the respective mRNA. This will allow for development of novel distinct SAR for these new cap structures for eIF4E-cap protein and lead to messenger RNA caps with improved eIF4E binding, and enhanced resistance to degradation, which in turn can result in increased rate of translation, extended stability of the "closed-loop" conformation and enhanced production of target proteins of therapeutic value.

In one aspect, the present disclosure provides a compound (e.g., a cap analog) of formula (I) below or a stereoisomer, tautomer or salt thereof:

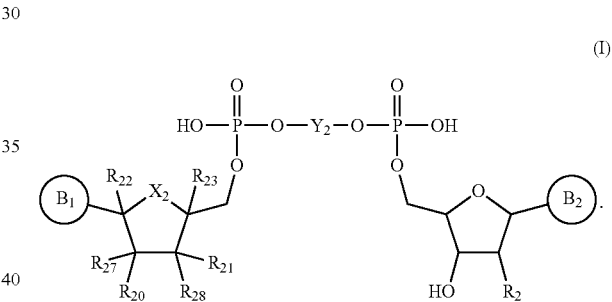

(I)

In formula (I) above, ring $B_1$ is a modified Guanine;

ring $B_2$ is a nucleobase or a modified nucleobase;

$X_2$ is O, $S(O)_p$, $NR_{24}$ or $CR_{25}R_{26}$ in which p is 0, 1, or 2;

$Y_2$ is —$(CR_{40}R_{41})_u$-$Q_0$-$(CR_{42}R_{43})_v$—, in which $Q_0$ is a bond, O, $S(O)_r$, $NR_{44}$, or $CR_{45}R_{46}$, r is 0, 1, or 2, and each of u and v independently is 1, 2, 3 or 4;

$R_2$ is halo, LNA, or $OR_3$;

$R_3$ is H, $C_1$-$C_6$ alkyl, $C_2$-$C_6$ alkenyl, or $C_2$-$C_6$ alkynyl and $R_3$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;

each of $R_{20}$, $R_{21}$, $R_{22}$, and $R_{23}$ independently is-$Q_3$-$T_3$, in which $Q_3$ is a bond or $C_1$-$C_3$ alkyl linker optionally substituted with one or more of halo, cyano, OH and $C_1$-$C_6$ alkoxy, and $T_3$ is H, halo, OH, $NH_2$, cyano, $NO_2$, $N_3$, $R_{S3}$, or $OR_{S3}$, in which $R_{S3}$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, NHC(O)—$C_1$-$C_6$ alkyl, mono-$C_1$-$C_6$ alkylamino, di-$C_1$-$C_6$ alkylamino, 4 to 12-membered heterocycloalkyl, or 5- or 6-membered heteroaryl, and $R_{S3}$ is optionally substituted with one or more substituents selected from the group consisting of halo, OH, oxo, $C_1$-$C_6$ alkyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

each of $R_{24}$, $R_{25}$, and $R_{26}$ independently is H or $C_1$-$C_6$ alkyl;

each of $R_{27}$ and $R_{28}$ independently is H or $OR_{29}$; or $R_{27}$ and $R_{28}$ together form O—$R_{30}$—O;

each $R_{29}$ independently is H, $C_1$-$C_6$ alkyl, $C_2$-$C_6$ alkenyl, or $C_2$-$C_6$ alkynyl and $R_{29}$, when being $C_1$-$C_6$ alkyl, $C_2$-$C_6$ alkenyl, or $C_2$-$C_6$ alkynyl, is optionally substituted with one or more of halo, OH and $C_1$-$C_6$ alkoxyl that is optionally substituted with one or more OH or OC(O)—$C_1$-$C_6$ alkyl;

$R_{30}$ is $C_1$-$C_6$ alkylene optionally substituted with one or more of halo, OH and $C_1$-$C_6$ alkoxyl;

each of $R_{40}$, $R_{41}$, $R_{42}$, and $R_{43}$ independently is H, halo, OH, cyano, $N_3$, OP(O)$R_{47}R_{48}$, or $C_1$-$C_6$ alkyl optionally substituted with one or more OP(O)$R_{47}R_{48}$, or one $R_{41}$ and one $R_{43}$, together with the carbon atoms to which they are attached and $Q_0$, form $C_4$-$C_{10}$ cycloalkyl, 4- to 14-membered heterocycloalkyl, $C_6$-$C_{10}$ aryl, or 5- to 14-membered heteroaryl, and each of the cycloalkyl, heterocycloalkyl, phenyl, or 5- to 6-membered heteroaryl is optionally substituted with one or more of OH, halo, cyano, $N_3$, oxo, OP(O)$R_{47}R_{48}$, $C_1$-$C_6$ alkyl, $C_1$-$C_6$ haloalkyl, COOH, C(O)O—$C_1$-$C_6$ alkyl, $C_1$-$C_6$ alkoxyl, $C_1$-$C_6$ haloalkoxyl, amino, mono-$C_1$-$C_6$ alkylamino, and di-$C_1$-$C_6$ alkylamino;

$R_{44}$ is H, $C_1$-$C_6$ alkyl, or an amine protecting group;

each of $R_{45}$ and $R_{46}$ independently is H, OP(O)$R_{47}R_{48}$, or $C_1$-$C_6$ alkyl optionally substituted with one or more OP(O)$R_{47}R_{48}$, and each of $R_{47}$ and $R_{48}$, independently is H, halo, $C_1$-$C_6$ alkyl, OH, SH, SeH, or BH3.

The compound of formula (I) or a stereoisomer, tautomer or salt thereof can have one or more of the following features when applicable.

For example, $R_2$ is halo (e.g., fluorine, chlorine, bromine, and iodine).

For example, $R_2$ is fluorine.

For example, $R_2$ is LNA.

For example, $R_2$ is $OR_3$.

For example, $R_3$ is H.

For example, $R_3$ is $C_1$-$C_3$ alkyl, e.g., methyl.

For example, $R_3$ is $C_1$-$C_3$ alkyl substituted with one or more of $C_1$-$C_6$ alkoxyl that is optionally substituted with one or more OH or OC(O)—$C_1$-$C_6$ alkyl.

For example, $R_3$ is $CH_2CH_2OCH_3$.

For example, $R_3$ is $CH(OCH_2CH_2OH)_2$.

For example, $R_3$ is $CH(OCH_2CH_2OCOCH_3)_2$.

For example, $R_3$ is unsubstituted or substituted $C_2$-$C_6$ alkenyl, e.g., propen-3-yl.

For example, $R_3$ is unsubstituted or substituted $C_2$-$C_6$ alkynyl, e.g., propyn-3-yl.

For example, ring $B_1$ is

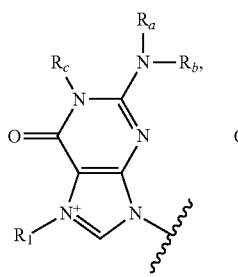 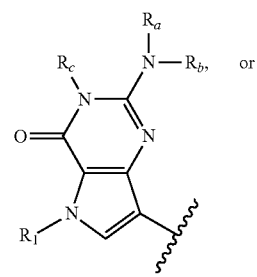 or

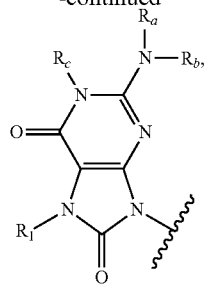

in which $R_1$ is $C_1$-$C_6$ alkyl, $C_2$-$C_6$ alkenyl, or $C_2$-$C_6$ alkynyl, each of which is optionally substituted with one or more substituents selected from the group consisting of $C_6$-$C_{10}$ aryl, $C_6$-$C_{10}$ aryloxyl, 5- to 10-membered heteroaryl, and 5- to 10-membered heteroaryloxyl, each being optionally substituted with one or more of halo and cyano;

each of $R_a$ and $R_b$ independently is H or $C_1$-$C_6$ alkyl; and $R_c$ is H, $NH_2$, or $C_1$-$C_6$ alkyl; or $R_c$ and one of $R_a$ and $R_b$, together with the two nitrogen atoms to which they attach and the carbon atom connecting the two nitrogen atoms form a 5- or 6-membered heterocycle which is optionally substituted with one or more of OH, halo, $C_1$-$C_6$ alkyl, $C_2$-$C_6$ alkenyl, and $C_2$-$C_6$ alkynyl, a stereoisomer, tautomer or salt thereof.

For example, ring $B_1$ is

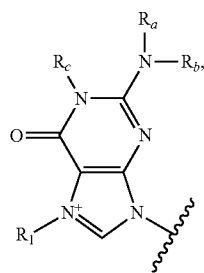

in which each of $R_a$, $R_b$ and $R_c$ independently is H or $C_1$-$C_6$ alkyl.

For example, ring $B_1$ is

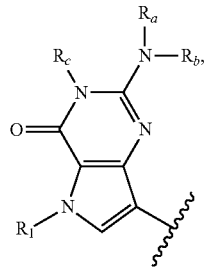

in which each of $R_a$, $R_b$ and $R_c$ independently is H or $C_1$-$C_6$ alkyl.

For example, ring $B_1$ is

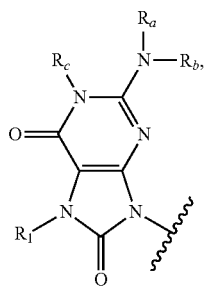

in which each of $R_a$, $R_b$ and $R_c$ independently is H or $C_1$-$C_6$ alkyl, and $R_1$ is $C_1$-$C_6$ alkyl or $C_2$-$C_6$ alkenyl (e.g., propen-3-yl).

For example, each of $R_a$ and $R_b$ independently is H or $C_1$-$C_3$ alkyl.

For example, $R_c$ is H.

For example, $R_c$ is $NH_2$.

For example, $R_c$ and one of $R_a$ and $R_b$, together with the two nitrogen atoms to which they attach and the carbon atom connecting the two nitrogen atoms form a 5- or 6-membered heterocycle which is optionally substituted with one or more of OH, halo, $C_1$-$C_6$ alkyl, $C_2$-$C_6$ alkenyl, and $C_2$-$C_6$ alkynyl. For example, the other of $R_a$ and $R_b$ that does not form the heterocycle is absent, H, or $C_1$-$C_6$ alkyl.

For example, ring $B_1$ is

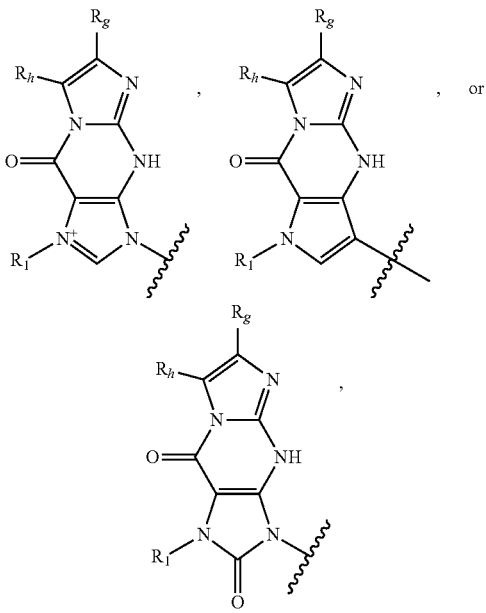

in which each of $R_g$ and $R_h$ independently is H or $C_1$-$C_3$ alkyl.

For example, $R_g$ is H or methyl.
For example, $R_h$ is H or methyl.
For example, $R_1$ is $C_1$-$C_3$ alkyl.
For example, $R_1$ is methyl.
For example, $R_1$ is ethyl substituted with phenoxyl that is substituted with one or more of halo and cyano.
For example, $R_1$ is 4-chlorophenoxylethyl, 4-bromophenoxylethyl, or 4-cyanophenoxylethyl.

For example, $R_1$ is $C_2$-$C_6$ alkenyl (e.g., propen-3-yl).
For example, ring $B_2$ is

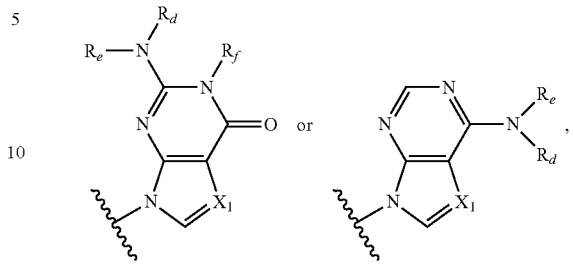

in which
$X_1$ is N or $N^+(R_5)$;
$R_5$ is $C_1$-$C_6$ alkyl, $C_2$-$C_6$ alkenyl, or $C_2$-$C_6$ alkynyl, each of which is optionally substituted with one or more substituents selected from the group consisting of $C_6$-$C_{10}$ aryl, $C_6$-$C_{10}$ aryloxyl, 5- to 10-membered heteroaryl, and 5- to 10-membered heteroaryloxyl, each being optionally substituted with one or more of halo and cyano;
each of $R_d$ and $R_e$ independently is H or $C_1$-$C_6$ alkyl; and
$R_f$, when present, is H, $NH_2$, or $C_1$-$C_6$ alkyl; or $R_f$ and one of $R_d$ and $R_e$, together with the two nitrogen atoms to which they attach and the carbon atom connecting the two nitrogen atoms form a 5- or 6-membered heterocycle which is optionally substituted with one or more of OH, halo, $C_1$-$C_6$ alkyl, $C_2$-$C_6$ alkenyl, and $C_2$-$C_6$ alkynyl, or
a stereoisomer, tautomer or salt thereof.

For example, each of $R_d$ and $R_e$ independently is H or $C_1$-$C_3$ alkyl.

For example, $R_d$ is H or methyl.
For example, $R_e$ is H or methyl.
For example, $R_f$, when present, is H.
For example, $R_f$, when present, is $NH_2$.
For example, $R_f$, when present, is $C_1$-$C_6$ alkyl.

For example, $R_f$ and one of $R_d$ and $R_e$, together with the two nitrogen atoms to which they attach and the carbon atom connecting the two nitrogen atoms form a 5- or 6-membered heterocycle which is optionally substituted with one or more of OH, halo, $C_1$-$C_6$ alkyl, $C_2$-$C_6$ alkenyl, and $C_2$-$C_6$ alkynyl.

For example, the other of $R_d$ and $R_e$ that does not form the heterocycle is absent, H, or $C_1$-$C_6$ alkyl.

For example, ring $B_2$ is

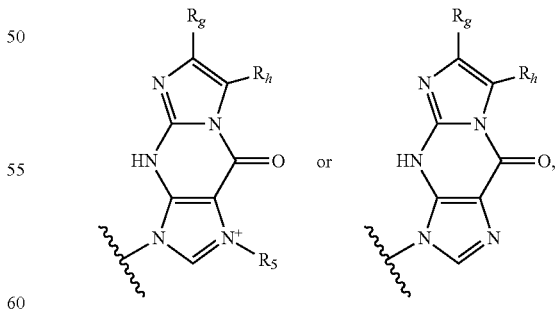

in which each of $R_g$ and $R_h$ independently is H or $C_1$-$C_3$ alkyl. For example, $R_g$ is H or methyl. For example, $R_h$ is H or methyl.

For example, $X_1$ is N.
For example, $X_1$ is $N^+(R_5)$.
For example, $R_5$ is methyl.

For example, $R_5$ is ethyl substituted with phenoxyl that is substituted with one or more of halo and cyano.

For example, $R_5$ is 4-chlorophenoxylethyl, 4-bromophenoxylethyl, or 4-cyanophenoxylethyl.

For example, $X_2$ is O.

For example, $X_2$ is S, SO, or $SO_2$.

For example, $X_2$ is $NR_{24}$.

For example, $X_2$ is $CR_{25}R_{26}$.

For example, $R_{24}$ is H.

For example, $R_{24}$ is straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $R_{25}$ is H.

For example, $R_{25}$ is straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $R_{26}$ is H.

For example, $R_{26}$ is straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, each of $R_{25}$ and $R_{26}$ is H.

For example, $R_{27}$ is H.

For example, $R_{28}$ is H.

For example, $R_{27}$ is OH.

For example, $R_{28}$ is OH.

For example, both $R_{27}$ and $R_{28}$ are OH.

For example, $R_{27}$ is $OR_{29}$.

For example, $R_{28}$ is $OR_{29}$.

For example, both $R_{27}$ and $R_{28}$ are $OR_{29}$.

For example, at least one of $R_{27}$ and $R_{28}$ is $OR_{29}$.

For example, each $R_{29}$ independently is H.

For example, each $R_{29}$ independently is $C_1$-$C_3$ alkyl, e.g., methyl.

For example, each $R_{29}$ independently is $C_1$-$C_3$ alkyl substituted with one or more of $C_1$-$C_6$ alkoxyl that is optionally substituted with one or more OH or OC(O)—$C_1$-$C_6$ alkyl.

For example, each $R_{29}$ independently is $CH_2CH_2OCH_3$.

For example, each $R_{29}$ independently is $CH(OCH_2CH_2OH)_2$.

For example, each $R_{29}$ independently is $CH(OCH_2CH_2OCOCH_3)_2$.

For example, each $R_{29}$ independently is unsubstituted or substituted $C_2$-$C_6$ alkenyl, e.g., propen-3-yl.

For example, each $R_{29}$ independently is unsubstituted or substituted $C_2$-$C_6$ alkynyl, e.g., propyn-3-yl.

For example, $R_{27}$ is $OCH_2CH_2OCH_3$ and $R_1$ is ethyl substituted with phenoxyl that is substituted with one or more of halo and cyano, e.g., $R_1$ being 4-chlorophenoxylethyl, 4-bromophenoxylethyl, or 4-cyanophenoxylethyl.

For example, $R_{27}$ and $R_{28}$ together form O—$R_{30}$—O.

For example, $R_{30}$ is $C_1$-$C_6$ alkylene optionally substituted with one or more of OH, halo, and $C_1$-$C_6$ alkoxyl.

For example, $R_{30}$ is —$C(CH_3)_2$—, —$CH_2$—, —$CH_2CH_2$—, —$CH_2CH_2CH_2$—, or —$CH_2CH(CH_3)_2$—.

For example, one subset of the compounds of formula (I) includes those of formula (Ia) or (Ib):

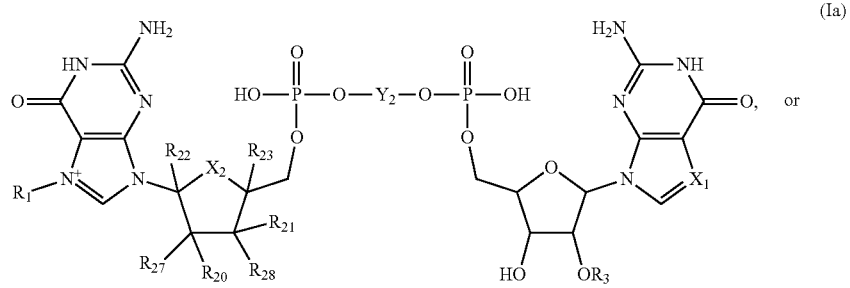

(Ia)

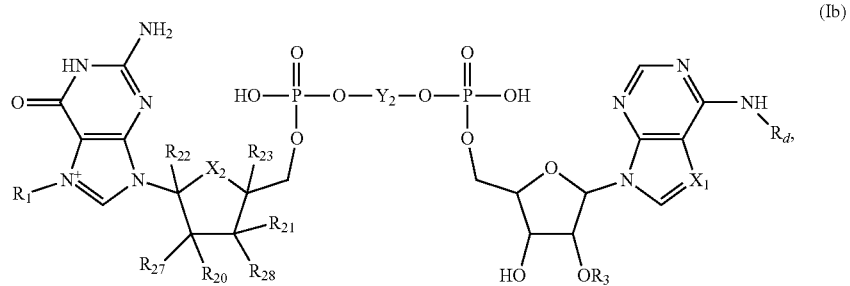

(Ib)

or a stereoisomer, tautomer or salt thereof.

For example, another subset of the compounds of formula (I) includes those of formula (IIa) or (IIb):
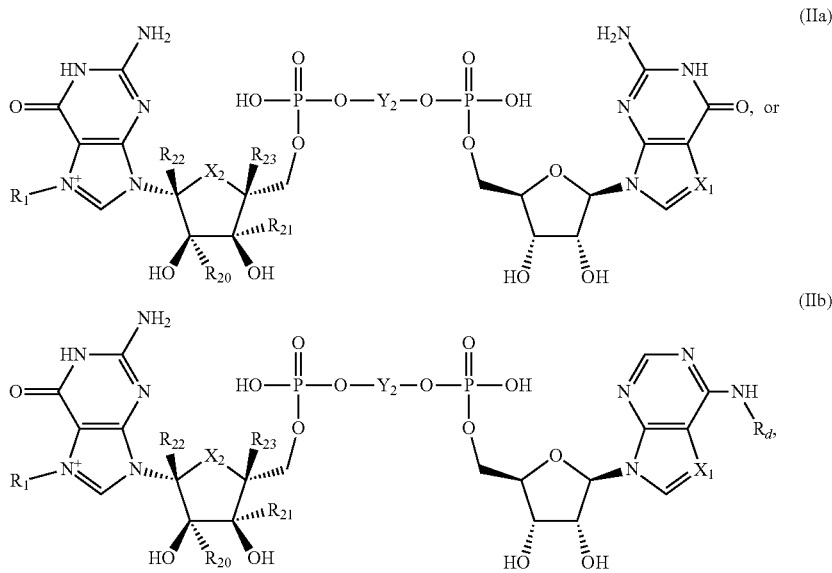
or a stereoisomer, tautomer or salt thereof.
For example, another subset of the compounds of formula (I) includes those of formula (IIc), (IId), (IIe), or (IIf):
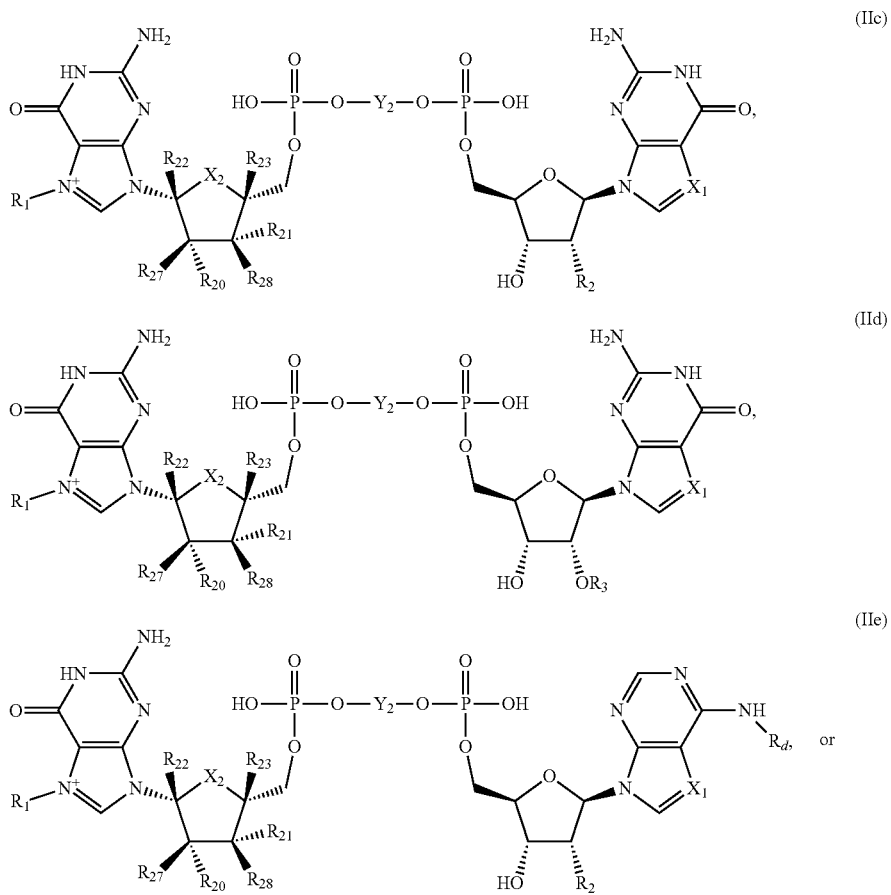

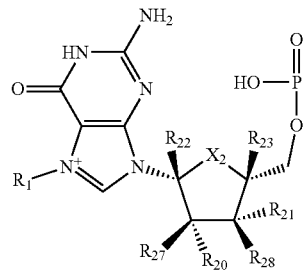
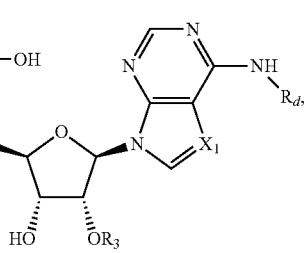

(IIf)

or a stereoisomer, tautomer or salt thereof.

For example, each of $R_{20}$, $R_{21}$, $R_{22}$, and $R_{23}$, independently, is -$Q_3$-$T_3$.

For example, $Q_3$ is a bond.

For example, $Q_3$ is an unsubstituted $C_1$-$C_3$ alkyl linker.

For example, $T_3$ is H or OH.

For example, $T_3$ is $N_3$.

For example, $T_3$ is cyano.

For example, $T_3$ is $NO_2$.

For example, $T_3$ is $NH_2$.

For example, $T_3$ is NHCO—$C_1$-$C_6$ alkyl, e.g., NHCOCH$_3$.

For example, $T_3$ is $R_{S3}$ or $OR_{S3}$ in which $R_{S3}$ is optionally substituted $C_1$-$C_6$ alkyl, $C_2$-$C_6$ alkenyl, $C_2$-$C_6$ alkynyl, or $C_6$-$C_{10}$ aryl.

For example, $R_{S3}$ is an unsubstituted or substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $R_{S3}$ is unsubstituted or substituted $C_2$-$C_6$ alkenyl, e.g., propen-3-yl.

For example, $R_{S3}$ is unsubstituted or substituted $C_2$-$C_6$ alkynyl, e.g., propyn-3-yl.

For example, $T_3$ is an unsubstituted or substituted straight chain $C_1$-$C_6$ or branched $C_3$-$C_6$ alkyl, including but not limited to, methyl, ethyl, n-propyl, i-propyl, n-butyl, s-butyl, t-butyl, n-pentyl, s-pentyl and n-hexyl.

For example, $T_3$ is optionally substituted $C_3$-$C_6$ cycloalkyl, including but not limited to, cyclopentyl and cyclohexyl.

For example, $T_3$ is optionally substituted phenyl.

For example, $T_3$ is halo (e.g., fluorine, chlorine, bromine, and iodine).

For example, $T_3$ is optionally substituted 4 to 7-membered heterocycloalkyl (e.g., azetidinyl, oxetanyl, thietanyl, pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like).

For example, $T_3$ is optionally substituted 5 to 6-membered heteroaryl (e.g., pyrrolyl, pyrazolyl, imidazolyl, pyridyl, pyrimidinyl, pyrazinyl, pyridazinyl, triazolyl, tetrazolyl, oxazolyl, isoxazolyl, thiazolyl, isothiazolyl, and the like).

For example, each of $R_{20}$, $R_{21}$, $R_{22}$, and $R_{23}$ independently is H, OH, halo, $NH_2$, cyano, $NO_2$, $N_3$, $C_1$-$C_6$ alkoxyl, benzyl, or $C_1$-$C_6$ alkyl optionally substituted with halo.

For example, each of $R_{20}$, $R_{21}$, $R_{22}$, and $R_{23}$ independently is H, cyano, $N_3$, $C_1$-$C_6$ alkyl, or benzyl.

For example, one of $R_{20}$ and $R_{21}$ is H and the other is $R_{20}$ is cyano, $NO_2$, $N_3$, or $C_1$-$C_3$ alkyl.

For example, both $R_{20}$ and $R_{21}$ are H.

For example, at least one of $R_{20}$ and $R_{27}$ is H.

For example, at least one of $R_{21}$ and $R_{28}$ is H.

For example, $R_{22}$ and $R_{23}$ are each H.

For example, one of $R_{22}$ and $R_{23}$ is H and the other is cyano, $NO_2$, $N_3$, or $C_1$-$C_3$ alkyl.

For example, at least one of $R_{20}$, $R_{21}$, $R_{22}$, and $R_{23}$ is not H.

For example, each of $R_{20}$, $R_{21}$, $R_{22}$, and $R_{23}$ is H.

For example, $Y_2$ is —$CH_2CH_2$—.

For example, $Y_2$ is —$CH_2CH_2$-$Q_0$-$CH_2CH_2$—.

For example, $Y_2$ is —$(CR_{40}R_{41})_{u-1}$—$CH(R_{41})$-$Q_0$-$CH(R_{43})$—$(CR_{42}R_{43})_{v-1}$—.

For example, u is 1 or 2.

For example, u is 3.

For example, u is 4.

For example, v is 1 or 2.

For example, v is 3.

For example, v is 4.

For example, u is the same as v.

For example, u is different from v.

For example, $Q_0$ is a bond.

For example, $Q_0$ is O.

For example, $Q_0$ is S, SO, or $SO_2$.

For example, $Q_0$ is $NR_{44}$, e.g., NH.

For example, $Q_0$ is $CR_{45}R_{46}$.

For example, each of $R_{41}$ and $R_{43}$ is H.

For example, each of $R_{40}$ and $R_{42}$ is H.

For example, one $R_{41}$ and one $R_{43}$, together with the carbon atoms to which they are attached and $Q_0$, form $C_5$-$C_8$ cycloalkyl, 5- to 8-membered heterocycloalkyl, phenyl, or 5- to 6-membered heteroaryl, and each of the cycloalkyl, heterocycloalkyl, phenyl, or 5- to 6-membered heteroaryl is optionally substituted with one or more of OH, halo, cyano, oxo, $C_1$-$C_6$ alkyl, or $C_1$-$C_6$ haloalkyl.

For example, $Y_2$ is —$CH(R_{41})$-$Q_0$-$CH(R_{43})$—. For example, each of $R_{41}$ and $R_{43}$ is H. For example, $R_{41}$ and $R_{43}$, together with the carbon atoms to which they are attached and $Q_0$, form $C_5$-$C_8$ cycloalkyl (e.g., cyclopentyl, cyclohexyl, and the like). For example, $R_{41}$ and $R_{43}$, together with the carbon atoms to which they are attached and $Q_0$, form 5- to 8-membered heterocycloalkyl (e.g., pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like). For example, $R_{41}$ and $R_{43}$, together with the carbon atoms to which they are attached and $Q_0$, form phenyl. For example, $R_{41}$ and $R_{43}$, together with the carbon atoms to which they are attached and $Q_0$, form 5- to 6-membered heteroaryl (e.g., pyrrolyl, pyrazolyl, imidazolyl, pyridyl, pyrimidinyl, pyrazinyl, pyridazinyl, triazolyl, tetrazolyl, oxazolyl, isoxazolyl, thiazolyl, isothiazolyl, and the like). For example, each of said cycloalkyl, heterocycloalkyl, phenyl, or 5- to 6-membered heteroaryl is optionally substituted with one or more of OH, halo, cyano, oxo, OP(O)$R_{47}R_{48}$ (e.g., OP(O)(OH)$_2$ or OP(O)(F)(OH)), $C_1$-$C_6$ alkyl, or $C_1$-$C_6$ haloalkyl.

For example, $Y_2$ is —CH$_2$—CH($R_{41}$)-$Q_0$-CH($R_{43}$)—CH$_2$—. For example, each of $R_{41}$ and $R_{43}$ is H. For example, each of $R_{41}$ and $R_{43}$ is OP(O)$R_{47}R_{48}$, e.g., OP(O)(OH)$_2$. For example, $R_{41}$ and $R_{43}$, together with the carbon atoms to which they are attached and $Q_0$, form $C_5$-$C_8$ cycloalkyl (e.g., cyclopentyl, cyclohexyl, and the like). For example, $R_{41}$ and $R_{43}$, together with the carbon atoms to which they are attached and $Q_0$, form 5- to 8-membered heterocycloalkyl (e.g., pyrrolidinyl, imidazolidinyl, pyrazolidinyl, oxazolidinyl, isoxazolidinyl, triazolidinyl, tetrahyrofuranyl, piperidinyl, 1,2,3,6-tetrahydropyridinyl, piperazinyl, tetrahydro-2H-pyranyl, 3,6-dihydro-2H-pyranyl, and morpholinyl, and the like). For example, $R_{41}$ and $R_{43}$, together with the carbon atoms to which they are attached and $Q_0$, form phenyl. For example, $R_{41}$ and $R_{43}$, together with the carbon atoms to which they are attached and $Q_0$, form 5- to 6-membered heteroaryl (e.g., pyrrolyl, pyrazolyl, imidazolyl, pyridyl, pyrimidinyl, pyrazinyl, pyridazinyl, triazolyl, tetrazolyl, oxazolyl, isoxazolyl, thiazolyl, isothiazolyl, and the like). For example, each of said cycloalkyl, heterocycloalkyl, phenyl, or 5- to 6-membered heteroaryl is optionally substituted with one or more of OH, halo, cyano, oxo, OP(O)$R_{47}R_{48}$ (e.g., OP(O)(OH)$_2$ or OP(O)(F)(OH)), $C_1$-$C_6$ alkyl, or $C_1$-$C_6$ haloalkyl.

For example, $R_{41}$ and $R_{43}$, together with the carbon atoms to which they are attached and $Q_0$, form 1,3-cyclohexyl, 2,6-tetrahydropyranyl, 2,6-tetrahydropyranyl, or 2,5-thiazolyl, each of which is optionally substituted with one or more OH.

For example, $R_{44}$ is $C_1$-$C_6$ alkyl.

For example, $R_{44}$ is H.

For example, $R_{44}$ is an amine protecting group (e.g., t-butyloxylcarbonyl).

For example, each of $R_{45}$ and $R_{46}$ is H.

For example, at least one of $R_{45}$ and $R_{46}$ is OP(O)$R_{47}R_{48}$, or $C_1$-$C_6$ alkyl optionally substituted with one or more OP(O)$R_{47}R_{48}$.

For example, at least one of $R_{47}$ and $R_{48}$ is halo, e.g., F, Cl, Br or I.

For example, at least one of $R_{47}$ and $R_{48}$ is OH.

For example, one of $R_{45}$ and $R_{46}$ is H and the other is OP(O)(OH)$_2$.

For example, one of $R_{45}$ and $R_{46}$ is H and the other is OP(O)(F)(OH).

For example, one of $R_{45}$ and $R_{46}$ is H and the other is $C_1$-$C_6$ alkyl optionally substituted with one or more OP(O)$R_{47}R_{48}$, e.g., OP(O)(OH)$_2$.

For example, each of $R_{45}$ and $R_{46}$ independently is $C_1$-$C_6$ alkyl optionally substituted with one or more OP(O)$R_{47}R_{48}$.

For example, each of $R_{45}$ and $R_{46}$ independently is $C_1$-$C_6$ alkyl optionally substituted with one or more OP(O)(OH)$_2$, e.g., —CH$_2$—OP(O)(OH)$_2$.

For example, each of $R_{45}$ and $R_{46}$ independently is $C_1$-$C_6$ alkyl optionally substituted with one or more OP(O)(F)(OH), e.g., —CH$_2$—OP(O)(F)(OH).

In embodiments, the variables in formulae (Ia), (Ib) and (IIa)-(IIf) are as defined herein for formula (I), where applicable.

In embodiments, the compounds of any of formulae (I), (Ia), (Ib) and (IIa)-(IIf) are cap analogs. In embodiments, the compounds of any of formulae (I), (Ia), (Ib) and (IIa)-(IIf) are anti-reverse cap analogs (ARCAs). In embodiments, a compound of any of formulae (I), (Ia), (Ib) and (IIa)-(IIf) is incorporated in an RNA molecule (e.g., mRNA) at the 5' end.

In yet another aspect, the present disclosure also provides a compound (e.g., a cap analog) or a polynucleotide containing the cap analog having an improved eIF4E binding affinity, enhanced resistance to degradation, or both, as compared to, e.g., natural mRNA caps and natural mRNAs. As used herein, $k_{off}$ is the off-rate, calculated from the dissociation phase, $k_{on}$ is the on-rate, calculated from the association phase; $K_d$ or $K_D$ is the binding affinity, which is the ratio of $k_{off}/k_{on}$, and the residence time, $\tau$, is the inverse of $k_{off}$.

In embodiments, the compound with an improved eIF4E binding affinity has a residence time, t, of about 2 seconds or longer when binding with the eukaryotic initiation factor 4E (eIF4E) characterized by surface plasmon resonance (SPR). For example, t of the compound is 5 seconds, 10 seconds, 15 seconds, 20 seconds, 25 seconds, 30 seconds, 50 seconds, 75 seconds, 80 seconds, 90 seconds, 100 seconds, or longer. For example, the compound has an eIF4E $k_{off}$ of no more than 1 s$^{-1}$ (e.g., no more than 0.9, 0.8, 0.7, 0.6, 0.5, 0.4, 0.3, 0.2, 0.1, 0.08, 0.06, 0.04, 0.02, or 0.01 s$^{-1}$). For example, the compound having t of about 2 seconds or longer (e.g., 5 seconds, 10 seconds, 15 seconds, 20 seconds, 25 seconds, 30 seconds, 50 seconds, 75 seconds, 80 seconds, 90 seconds, 100 seconds, or longer) is a compound of any of formulae (I), (Ia), (Ib) and (IIa)-(IIf) or a derivative or analog thereof. For example, the compound having t of about 2 seconds or longer (e.g., 5 seconds, 10 seconds, 15 seconds, 20 seconds, 25 seconds, 30 seconds, 50 seconds, 75 seconds, 80 seconds, 90 seconds, 100 seconds, or longer) is selected from any of those included in Tables 1-2, and stereoisomers, tautomers and salts thereof.

In embodiments, the compound with an improved eIF4E binding affinity has a residence time, t, of at least 2 times of that of a natural cap when binding with eIF4E characterized by surface plasmon resonance (SPR). For example, t of the compound is at least 3, 4, 5, 6, 7, 10, 15, 20, 25, 30, 40, 50, 60, 70, 80, 90, or 100 times of that of a natural cap. For example, the compound having t of at least 2 times (e.g., at least 3, 4, 5, 6, 7, 10, 15, 20, 25, 30, 40, 50, 60, 70, 80, 90, or 100 times) of that of a natural cap is a compound of any of formulae (I), (Ia), (Ib) and (IIa)-(IIf) or a derivative or analog thereof. For example, the compound having t of at least 2 times (e.g., at least 3, 4, 5, 6, 7, 10, 15, 20, 25, 30, 40, 50, 60, 70, 80, 90, or 100 times) of that of a natural cap is selected from any of those included in Tables 1-2, and stereoisomers, tautomers and salts thereof.

In embodiments, the compound with an improved eIF4E binding affinity has a $K_d$ or $K_D$ of no more than 10 μM, e.g., using SPR. For example, $K_d$ of the compound is no more than 9, 8, 7, 6, 5, 4, 3, 2, 1, 0.9, 0.7, 0.5, 0.3, or 0.1 μM. For example, the compound has an eIF4E $K_d$ of no more than 10 μM (e.g., no more than 9, 8, 7, 6, 5, 4, 3, 2, 1, 0.9, 0.7, 0.5, 0.3, or 0.1 μM) and a t of about 2 seconds or longer (e.g., 5 seconds, 10 seconds, 15 seconds, 20 seconds, 25 seconds, 30 seconds, 50 seconds, 75 seconds, 80 seconds, 90 seconds, 100 seconds, or longer). For example, the compound having $K_d$ of no more than 10 μM (e.g., no more than 9, 8, 7, 6, 5, 4, 3, 2, 1, 0.9, 0.7, 0.5, 0.3, or 0.1 μM) is a compound of any of formulae (I), (Ia), (Ib) and (IIa)-(IIf) or a derivative or analog thereof. For example, the compound having $K_d$ of no more than 10 μM (e.g., no more than 9, 8, 7, 6, 5, 4, 3, 2, 1, 0.9, 0.7, 0.5, 0.3, or 0.1 μM) is selected from any of those included in Tables 1-2, and stereoisomers, tautomers and salts thereof.

In embodiments, the RNA molecule carrying the compound (e.g., a cap analog) disclosed herein has enhanced resistance to degradation. For example, the modified RNA molecule has a half-life that is at least 1.2 times of that of a corresponding natural RNA molecule in a cellular environment. For example, the half-life of the modified RNA molecule is at least 1.5, 2, 3, 4, 5, 6, 7, 10, 15, 20, 25, 30, 40, 50, 60, 70, 80, 90, or 100 times of that of a corresponding natural RNA molecule in a cellular environment. For example, the modified RNA molecule carries a compound of any of formulae (I), (Ia), (Ib) and (IIa)-(IIf) or a derivative or analog thereof. For example, the modified RNA molecule carries a compound selected from any of those included in Tables 1-2, and stereoisomers, tautomers and salts thereof.

Representative compounds of the present disclosure include compounds listed in Tables 1 and 2 and stereoisomer, tautomer, and salts thereof.

TABLE 1

| Cpd No. | $Y_2$ | $X_1$ |
|---|---|---|
| 1 | —CH$_2$CH$_2$— | N$^+$(CH$_3$) |
| 2 | —CH$_2$CH$_2$—O—CH$_2$CH$_2$— | N$^+$(CH$_3$) |
| 3 | —CH$_2$CH$_2$—S—CH$_2$CH$_2$— | N$^+$(CH$_3$) |
| 4 | —CH$_2$CH$_2$—S(O)—CH$_2$CH$_2$— | N$^+$(CH$_3$) |
| 5 | —CH$_2$CH$_2$—S(O)$_2$—CH$_2$CH$_2$— | N$^+$(CH$_3$) |
| 6 | —CH$_2$CH$_2$—NH—CH$_2$CH$_2$— | N$^+$(CH$_3$) |
| 7 | [structure: CH with OP(=O)(OH)$_2$ substituent] | N$^+$(CH$_3$) |
| 8 | [cyclohexane-1,3-diyl] | N$^+$(CH$_3$) |
| 9 | [5-hydroxycyclohexane-1,3-diyl] | N$^+$(CH$_3$) |
| 10 | [tetrahydropyran-2,6-diyl] | N$^+$(CH$_3$) |
| 11 | [tetrahydropyran-3,5-diyl] | N$^+$(CH$_3$) |
| 12 | [thiazole-2,5-diyl-bis(ethylene)] | N$^+$(CH$_3$) |

TABLE 1-continued

[Structure shown: 7-methylguanosine connected via 5'-O-P(OH)(=O)-O-Y₂-O-P(OH)(=O)-O-5' to a second nucleoside with base containing X₁]

| Cpd No. | Y₂ | X₁ |
|---|---|---|
| 13 | —CH₂CH₂— | N |
| 14 | —CH₂CH₂—O—CH₂CH₂— | N |
| 15 | —CH₂CH₂—S—CH₂CH₂— | N |
| 16 | —CH₂CH₂—S(O)—CH₂CH₂— | N |
| 17 | —CH₂CH₂—S(O)₂—CH₂CH₂— | N |
| 18 | —CH₂CH₂—NH—CH₂CH₂— | N |
| 19 | -CH₂-CH(OP(O)(OH)₂)-CH₂- | N |
| 20 | 1,3-cyclohexylene | N |
| 21 | 5-hydroxy-1,3-cyclohexylene | N |
| 22 | 2,6-tetrahydropyranyl-dimethylene | N |
| 23 | 3,5-tetrahydropyranylene | N |
| 24 | 2,5-thiazolyl-dimethylene | N |
| 25 | N-Boc-bis(propylene)amine | N⁺(CH₃) |

TABLE 1-continued
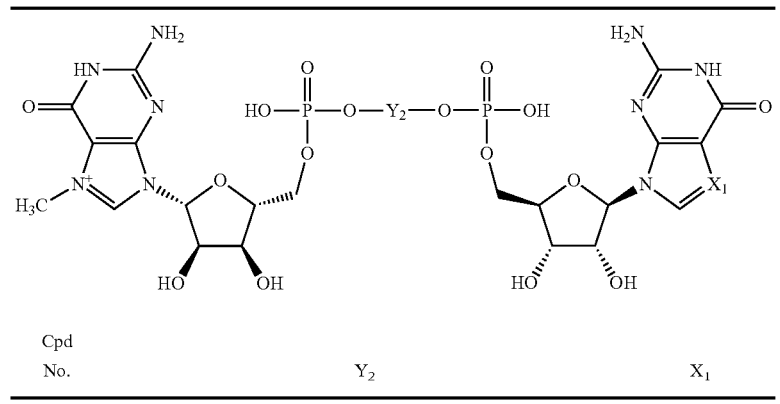
| Cpd No. | Y$_2$ | X$_1$ |
|---|---|---|
| 26 | 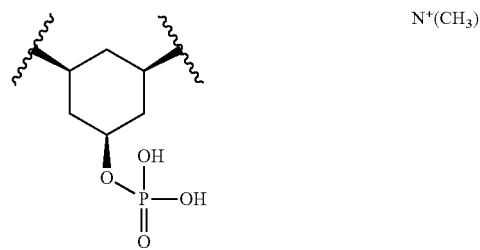 | N$^+$(CH$_3$) |
| 27 | 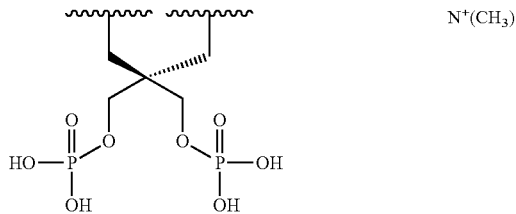 | N$^+$(CH$_3$) |
| 28 | 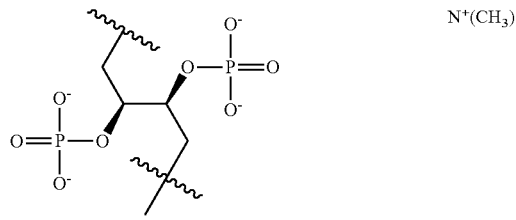 | N$^+$(CH$_3$) |
| 29 | 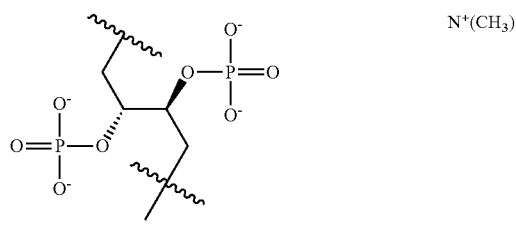 | N$^+$(CH$_3$) |
| 30 | 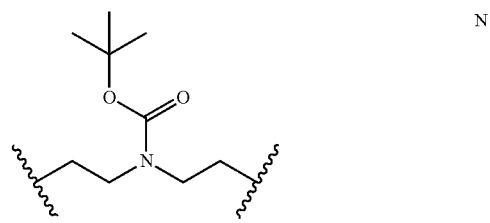 | N |

TABLE 1-continued
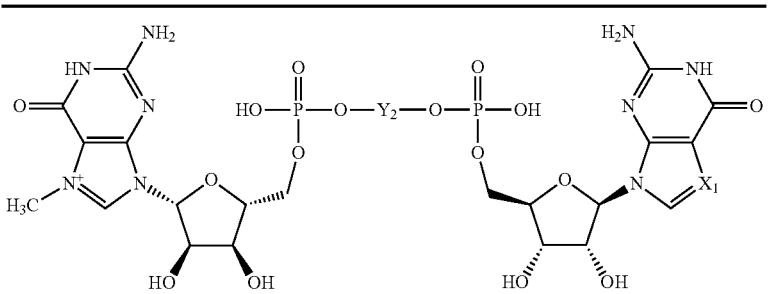
| Cpd No. | $Y_2$ | $X_1$ |
|---|---|---|
| 31 | 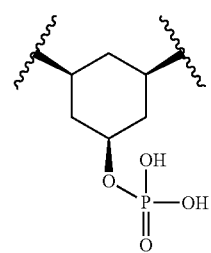 | N |
| 32 | 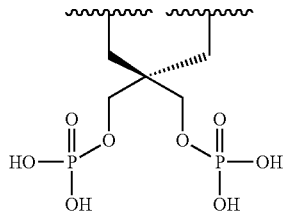 | N |
| 33 | 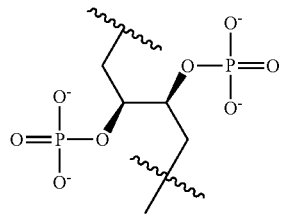 [SMILES: *C[C@H](OP(=O)([O-])[O-])[C@H](C*)OP(=O)([O-])[O-]] | N |
| 34 | 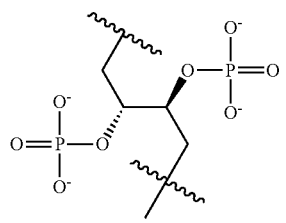 [SMILES: *C[C@H](OP(=O)([O-])[O-])[C@@H](C*)OP(=O)([O-])[O-]] | N |

TABLE 2

| Cpd No. | Structure |
|---|---|
| 35 | 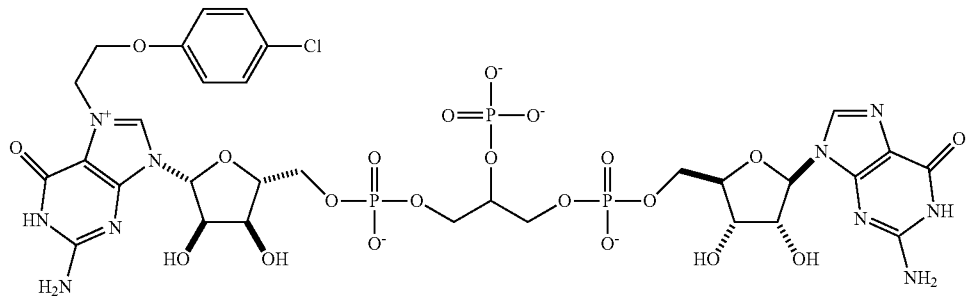 |
| 36 | 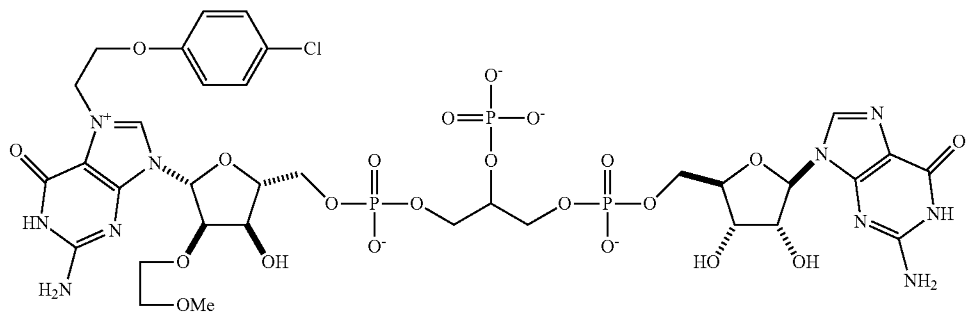 |
| 37 | 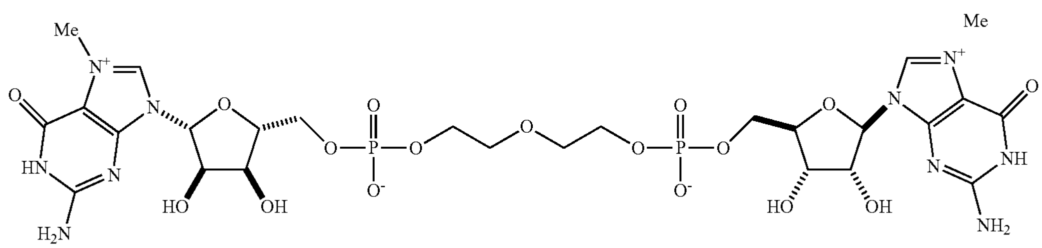 |
| 38 | 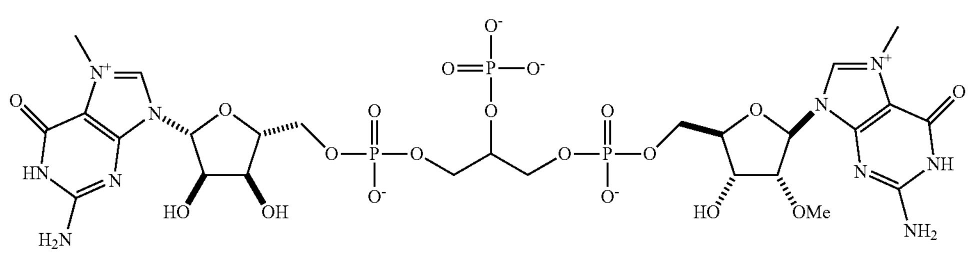 |
| 39 | 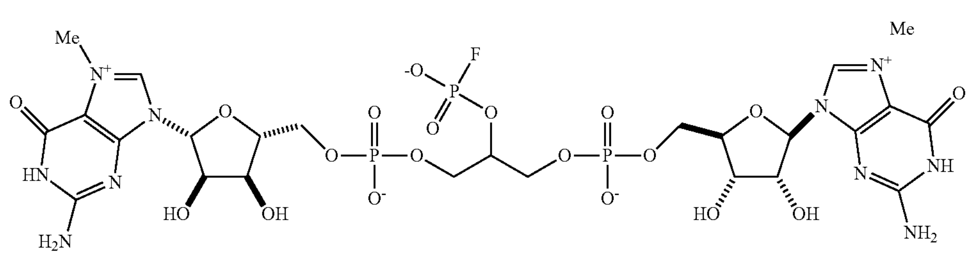 |

TABLE 2-continued

| Cpd No. | Structure |
|---|---|
| 40 | 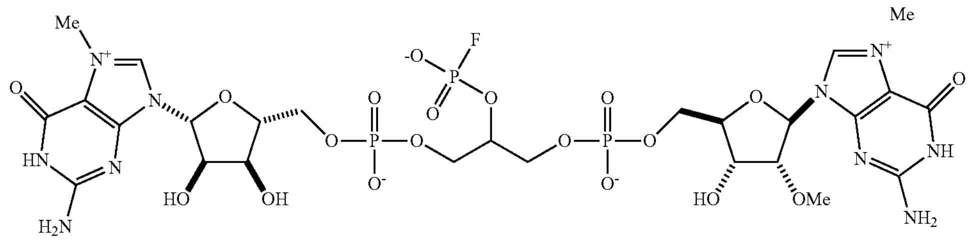 |
| 41 | 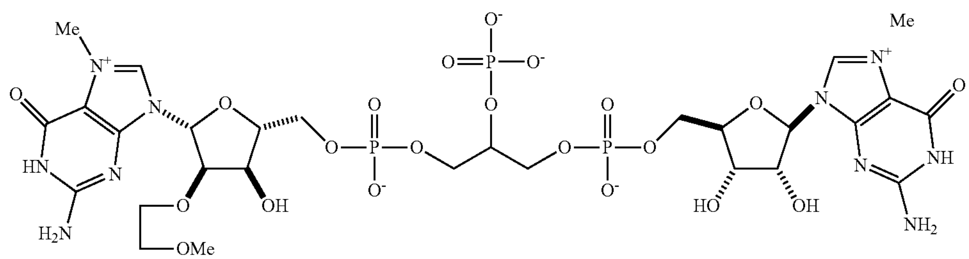 |
| 42 | 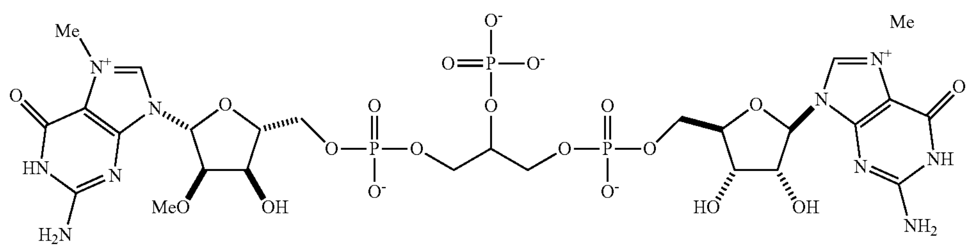 |
| 43 | 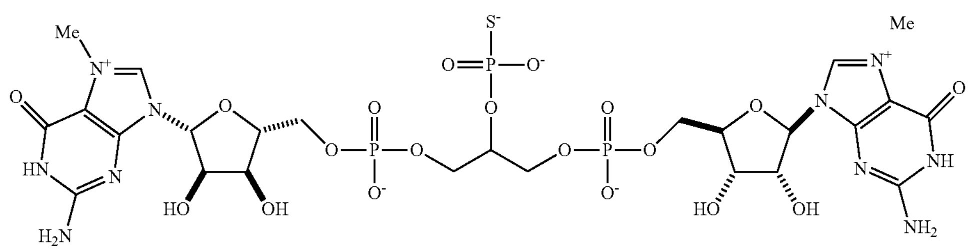 |

For example, the compounds listed in Tables 1 and 2 can or may have $B_1$ ring being replaced with any of those as defined in formula (I), e.g., those with $R_1$ being 4-chlorophenoxylethyl, 4-bromophenoxylethyl, or 4-cyanophenoxylethyl. Alternatively or additionally, the compounds listed in Tables 1-2 can or may have $B_2$ ring being replaced with any of those as defined in formula (I), e.g., unmodified or modified cytosine or uracil. As another example, the compounds listed in Tables 1-2 can or may have $R_2$ (e.g., OH) being replaced with any of those as defined in formula (I), e.g., $OCH_3$, $OCH(OCH_2CH_2OH)_2$ or $OCH(OCH_2CH_2OCOCH_3)_2$.

As used herein, the term "LNA" or "locked nucleic acid" refers to a methylene bridge between the 2'O and 4'C of the nucleotide monomer and it also refers to a sugar analog, a nucleoside, a nucleotide monomer, or a nucleic acid, each of which contains such bridge. For example, LNA has the following structure

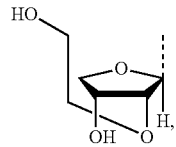

or those described in WO 99/14226 and Kore et al., *J. AM CHEM. SOC.* 2009, 131, 6364-6365, the contents of each of which are incorporated herein by reference in their entireties.

As used herein, the term "nucleobase" refers to a nitrogen-containing heterocyclic moiety, which is the parts of the nucleic acids that are involved in the hydrogen-bonding that binds one nucleic acid strand to another complementary strand in a sequence specific manner. The most common naturally-occurring nucleobases are: adenine (A), cytosine (C), guanine (G), thymine (T), and uracil (U).

The term "modified nucleobase" refers to a moiety that can replace a nucleobase. The modified nucleobase mimics the spatial arrangement, electronic properties, or some other physicochemical property of the nucleobase and retains the property of hydrogen-bonding that binds one nucleic acid strand to another in a sequence specific manner. A modified nucleobase can pair with at least one of the five naturally occurring bases (uracil, thymine, adenine, cytosine, or guanine) without substantially affecting the melting behavior, recognition by intracellular enzymes, or activity of the oligonucleotide duplex. The term "modified nucleoside" or "modified nucleotide" refers to a nucleoside or nucleotide that contains a modified nucleobase and/or other chemical modification disclosed herein, such as modified sugar, modified phosphorus atom bridges or modified internucleoside linkage.

Non-limiting examples of suitable nucleobases include, but are not limited to, uracil, thymine, adenine, cytosine, and guanine optionally having their respective amino groups protected by, e.g., acyl protecting groups, 5-propynyl-uracil, 2-thio-5-propynyl-uracil, 5-methylcytosine, 2-fluorouracil, 2-fluorocytosine, 5-bromouracil, 5-iodouracil, 2,6-diaminopurine, azacytosine, 2-thiouracil, 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine), N8-(8-aza-7-deazaadenine), pyrimidine analogs such as pseudoisocytosine and pseudouracil and other modified nucleobases such as 8-substituted purines, xanthine, or hypoxanthine (the latter two being the natural degradation products). Exemplary modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313.

Compounds represented by the following general formulae are also contemplated as nucleobases:

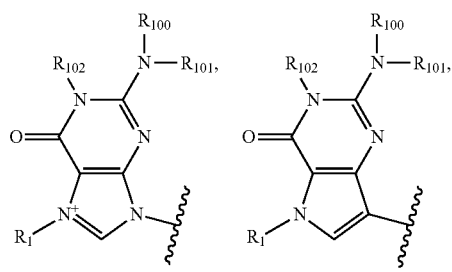

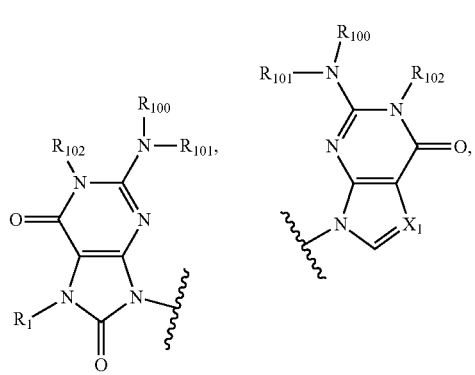

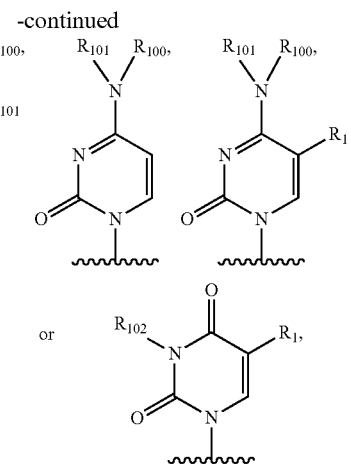

in which $R_1$ and $X_1$ are as defined herein, each of $R_{100}$ and $R_{101}$ independently is H, $C_1$-$C_6$ alkyl, or an amine protecting group (such as —C(O)R' in which R' is an optionally substituted, linear or branched group selected from aliphatic, aryl, aralkyl, aryloxylalkyl, carbocyclyl, heterocyclyl or heteroaryl group having 1 to 15 carbon atoms, including, by way of example only, a methyl, isopropyl, phenyl, benzyl, or phenoxymethyl group), or $R_{100}$ and $R_{101}$ together with the N atom to which they are attached form —N=CH—NR'R" in which each of R' and R" is independently an optionally substituted aliphatic, carbocyclyl, aryl, heterocyclyl or heteroaryl; or $R_{100}$ and $R_{101}$ together with the N atom to which they are attached form a 4 to 12-membered heterocycloalkyl (e.g., phthalimidyl optionally substituted with one or more substituents selected from OH and halo), —N=CH—$R_{103}$, or —N=N—$R_{103}$, wherein $R_{103}$ is phenyl, and each of the 4 to 12-membered heterocycloalkyl and $R_{103}$ is optionally substituted with one or more substituents selected from OH, oxo, halo, $C_1$-$C_6$ alkyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; and each $R_{102}$ independently is H, $NH_2$, or $C_1$-$C_6$ alkyl; or $R_{102}$ and one of $R_{100}$ and $R_{101}$, together with the two nitrogen atoms to which they attach and the carbon atom connecting the two nitrogen atoms form a 5- or 6-membered heterocycle which is optionally substituted with one or more of OH, halo, $C_1$-$C_6$ alkyl, $C_2$-$C_6$ alkenyl, and $C_2$-$C_6$ alkynyl, or a stereoisomer, tautomer or salt thereof. For example, the other of $R_{100}$ and $R_{101}$ that does not form the heterocycle is absent, H, or $C_1$-$C_6$ alkyl.

Modified nucleobases also include expanded-size nucleobases in which one or more aryl rings, such as phenyl rings, have been added. Some examples of these expanded-size nucleobases are shown below:

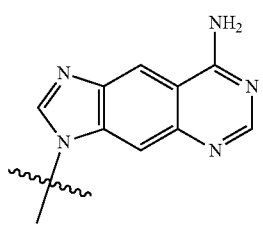

-continued

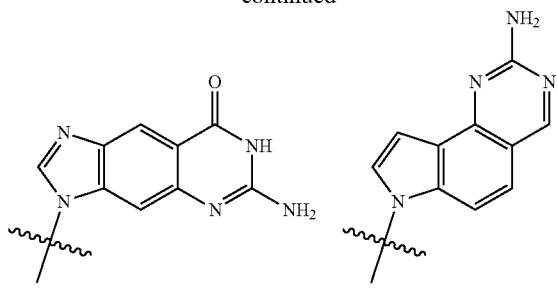

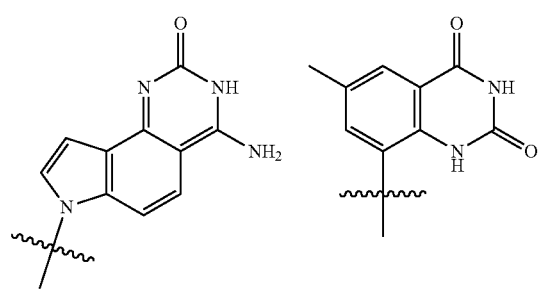

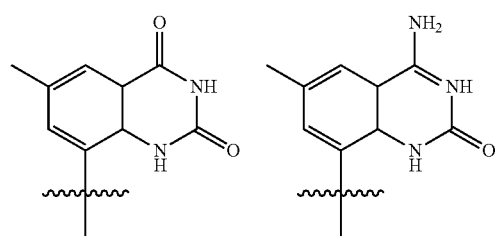

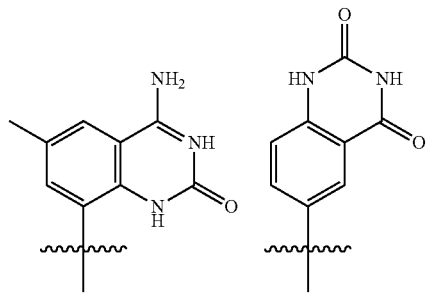

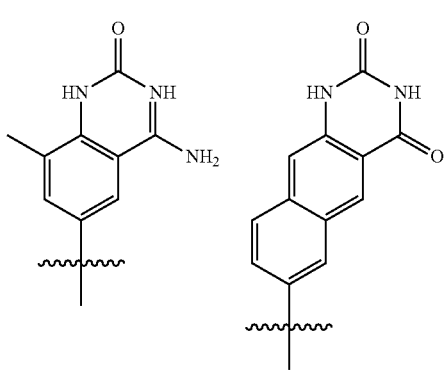

-continued

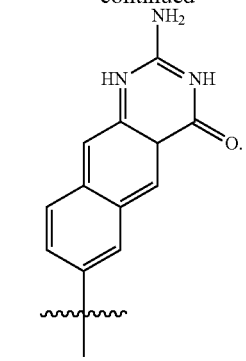

The term "modified sugar" or "sugar analog" refers to a moiety that can replace a sugar. The modified sugar mimics the spatial arrangement, electronic properties, or some other physicochemical property of a sugar.

As used herein, the terms "polynucleotide", "oligonucleotide" and "nucleic acid' are used interchangeably and refer to single stranded and double stranded polymers or oligomers of nucleotide monomers, including ribonucleotides (RNA) and 2'-deoxyribonucleotides (DNA) linked by internucleotide phosphodiester bond linkages. A polynucleotide may be composed entirely of deoxyribonucleotides, entirely of ribonucleotides or chimeric mixtures thereof.

As used herein, the term "messenger RNA" (mRNA) refers to any polynucleotide which encodes at least one peptide or polypeptide of interest and which is capable of being translated to produce the encoded peptide polypeptide of interest in vitro, in vivo, in situ or ex vivo. An mRNA has been transcribed from a DNA sequence by an RNA polymerase enzyme, and interacts with a ribosome to synthesize genetic information encoded by DNA. Generally, mRNA are classified into two sub-classes: pre-mRNA and mature mRNA. Precursor mRNA (pre-mRNA) is mRNA that has been transcribed by RNA polymerase but has not undergone any post-transcriptional processing (e.g., 5'capping, splicing, editing, and polyadenylation). Mature mRNA has been modified via post-transcriptional processing (e.g., spliced to remove introns and polyadenylated) and is capable of interacting with ribosomes to perform protein synthesis. mRNA can be isolated from tissues or cells by a variety of methods. For example, a total RNA extraction can be performed on cells or a cell lysate and the resulting extracted total RNA can be purified (e.g., on a column comprising oligo-dT beads) to obtain extracted mRNA.

Alternatively, mRNA can be synthesized in a cell-free environment, for example by in vitro transcription (IVT). An "in vitro transcription template" as used herein, refers to deoxyribonucleic acid (DNA) suitable for use in an IVT reaction for the production of messenger RNA (mRNA). In some embodiments, an IVT template encodes a 5' untranslated region, contains an open reading frame, and encodes a 3' untranslated region and a polyA tail.

The particular nucleotide sequence composition and length of an IVT template will depend on the mRNA of interest encoded by the template.

A "5' untranslated region (UTR)" refers to a region of an mRNA that is directly upstream (i.e., 5') from the start codon (i.e., the first codon of an mRNA transcript translated by a ribosome) that does not encode a protein or peptide.

A "3' untranslated region (UTR)" refers to a region of an mRNA that is directly downstream (i.e., 3') from the stop codon (i.e., the codon of an mRNA transcript that signals a termination of translation) that does not encode a protein or peptide.

An "open reading frame" is a continuous stretch of DNA beginning with a start codon (e.g., methionine (ATG)), and ending with a stop codon (e.g., TAA, TAG or TGA) and encodes a protein or peptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo, etc.) the poly(A) tail functions to protect mRNA from enzymatic degradation, e.g., in the cytoplasm, and aids in transcription termination, export of the mRNA from the nucleus, and translation.

Thus, the polynucleotide may in some embodiments comprise (a) a first region of linked nucleosides encoding a polypeptide of interest; (b) a first terminal region located 5' relative to said first region comprising a 5' untranslated region (UTR); (c) a second terminal region located 3' relative to said first region; and (d) a tailing region. The terms polynucleotide and nucleic acid are used interchangeably herein.

In some embodiments, the polynucleotide includes from about 200 to about 3,000 nucleotides (e.g., from 200 to 500, from 200 to 1,000, from 200 to 1,500, from 200 to 3,000, from 500 to 1,000, from 500 to 1,500, from 500 to 2,000, from 500 to 3,000, from 1,000 to 1,500, from 1,000 to 2,000, from 1,000 to 3,000, from 1,500 to 3,000, or from 2,000 to 3,000 nucleotides).

IVT mRNA disclosed herein may function as mRNA but are distinguished from wild-type mRNA in their functional and/or structural design features which serve to overcome existing problems of effective polypeptide production using nucleic-acid based therapeutics. For example, IVT mRNA may be structurally modified or chemically modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCG". Here, the dinucleotide "CC" has been inserted, resulting in a structural modification to the polynucleotide.

cDNA encoding the polynucleotides described herein may be transcribed using an in vitro transcription (IVT) system. The system typically comprises a transcription buffer, nucleotide triphosphates (NTPs), an RNase inhibitor and a polymerase. The NTPs may be manufactured in house, may be selected from a supplier, or may be synthesized as described herein. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate polynucleotides (e.g., modified nucleic acids). TP as used herein stands for triphosphate.

In embodiments, polynucleotides of the disclosure may include at least one chemical modification. The polynucleotides described herein can include various substitutions and/or insertions from native or naturally occurring polynucleotides, e.g., in addition to the modification on the 5' terminal mRNA cap moieties disclosed herein. As used herein, when referring to a polynucleotide, the terms "chemical modification" or, as appropriate, "chemically modified" refer to modification with respect to adenosine (A), guanosine (G), uridine (U), thymidine (T) or cytidine (C) ribo- or deoxyribnucleosides and the internucleoside linkages in one or more of their position, pattern, percent or population. Generally, herein, these terms are not intended to refer to the ribonucleotide modifications in naturally occurring 5'-terminal mRNA cap moieties.

The modifications may be various distinct modifications. In some embodiments, the regions may contain one, two, or more (optionally different) nucleoside or nucleotide modifications. In some embodiments, a modified polynucleotide introduced to a cell may exhibit reduced degradation in the cell as compared to an unmodified polynucleotide.

Modifications of the polynucleotides of the disclosure include, but are not limited to those listed in detail below. The polynucleotide may comprise modifications which are naturally occurring, non-naturally occurring or the polynucleotide can comprise both naturally and non-naturally occurring modifications.

The polynucleotides of the disclosure can include any modification, such as to the sugar, the nucleobase, or the internucleoside linkage (e.g., to a linking phosphate/to a phosphodiester linkage/to the phosphodiester backbone). One or more atoms of a pyrimidine or purine nucleobase may be replaced or substituted with optionally substituted amino, optionally substituted thiol, optionally substituted alkyl (e.g., methyl or ethyl), or halo (e.g., chloro or fluoro).

In certain embodiments, modifications (e.g., one or more modifications) are present in each of the sugar and the internucleoside linkage. Modifications according to the present disclosure may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

Non-natural modified nucleotides may be introduced to polynucleotides during synthesis or post-synthesis of the chains to achieve desired functions or properties. The modifications may be on internucleotide lineage, the purine or pyrimidine bases, or sugar. The modification may be introduced at the terminal of a chain or anywhere else in the chain; with chemical synthesis or with a polymerase enzyme. Any of the regions of the polynucleotides may be chemically modified.

The present disclosure provides for polynucleotides comprised of unmodified or modified nucleosides and nucleotides and combinations thereof. As described herein "nucleoside" is defined as a compound containing a sugar molecule (e.g., a pentose or ribose) or a derivative thereof in combination with an organic base (e.g., a purine or pyrimidine) or a derivative thereof (also referred to herein as "nucleobase"). As described herein, "nucleotide" is defined as a nucleoside including a phosphate group. The modified nucleotides may by synthesized by any useful method, as described herein (e.g., chemically, enzymatically, or recombinantly to include one or more modified or non-natural nucleosides). The polynucleotides may comprise a region or regions of linked nucleosides. Such regions may have variable backbone linkages. The linkages may be standard phosphodiester linkages, in which case the polynucleotides would comprise regions of nucleotides. Any combination of base/sugar or linker may be incorporated into the polynucleotides of the disclosure.

Modifications of polynucleotides (e.g., RNA polynucleotides, such as mRNA polynucleotides), including but not limited to chemical modification, that are useful in the compositions, methods and synthetic processes of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N$_6$ isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo)adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromoadenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine;

8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deaza-guanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio) pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl)pseudo-UTP; 1-Methyl-pseudo-UTP; 1-Ethyl-pseudo-UTP; 2 (thio) pseudouracil; 2' deoxy uridine; 2' fluorouridine; 2-(thio) uracil; 2,4-(dithio)psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio)uracil; 5 (propynyl)uracil; 5 (trifluoromethyl)uracil; 5-(2-aminopropyl)uracil; 5-(alkyl)-2-(thio) pseudouracil; 5-(alkyl)-2,4 (dithio)pseudouracil; 5-(alkyl)-4 (thio)pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; P seudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (+)$_1$-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3, 4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-

Amino-4-carboxybutyl)pseudo-UTP; 1-(4-Amino-benzyl) pseudo-UTP; 1-(4-Amino-butyl)pseudo-UTP; 1-(4-Aminophenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)- phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl; 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ₀), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl) pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropyl-wyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamyl-queuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQIbase, and two or more combinations thereof. In some embodiments, the at least one chemically modified nucleoside is selected from the group consisting of pseudouridine, 1-methyl-pseudouridine, 1-ethyl-pseudouridine, 5-methylcytosine, 5-methoxyuridine, and a combination thereof. In some embodiments, the polyribonucleotide (e.g., RNA polyribonucleotide, such as mRNA polyribonucleotide) includes a combination of at least two (e.g., 2, 3, 4 or more) of the aforementioned modified nucleobases. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine (m1ψ), 1-ethyl-pseudouridine (e1ψ), 5-methoxy-uridine (mo5U), 5-methyl-cytidine (m5C), pseudouridine (ψ), α-thio-guanosine and α-thio-adenosine. In some embodiments, the polyribonucleotide includes a combination of at least two (e.g., 2, 3, 4 or more) of the aforementioned modified nucleobases, including but not limited to chemical modifications.

In some embodiments, polynucleotides (e.g., RNA polynucleotides, such as mRNA polynucleotides) comprise pseudouridine (ψ) and 5-methyl-cytidine (m5C). In some embodiments, the polyribonucleotides (e.g., RNA, such as mRNA) comprise 1-methyl-pseudouridine (m1ψ). In some embodiments, the polyribonucleotides (e.g., RNA, such as mRNA) comprise 1-ethyl-pseudouridine (e1ψ). In some embodiments, the polyribonucleotides (e.g., RNA, such as mRNA) comprise 1-methyl-pseudouridine (m1ψ) and 5-methyl-cytidine (m5C). In some embodiments, the polyribonucleotides (e.g., RNA, such as mRNA) comprise 1-ethyl-pseudouridine (e1ψ) and 5-methyl-cytidine (m5C). In some embodiments, the polyribonucleotides (e.g., RNA, such as mRNA) comprise 2-thiouridine (s2U). In some embodiments, the polyribonucleotides (e.g., RNA, such as mRNA) comprise 2-thiouridine and 5-methyl-cytidine (m5C). In some embodiments, the polyribonucleotides (e.g., RNA, such as mRNA) comprise methoxy-uridine (mo5U). In some embodiments, the polyribonucleotides (e.g., RNA, such as mRNA) comprise 5-methoxy-uridine (mo5U) and 5-methyl-cytidine (m5C). In some embodiments, the polyribonucleotides (e.g., RNA, such as mRNA) comprise 2'-O-methyl uridine. In some embodiments, the polyribonucleotides (e.g., RNA, such as mRNA) comprise 2'-O-methyl uridine and 5-methyl-cytidine (m5C). In some embodiments, the polyribonucleotides (e.g., RNA, such as mRNA) comprise N6-methyl-adenosine (m6A). In some embodiments, the polyribonucleotides (e.g., RNA, such as mRNA) comprise N6-methyl-adenosine (m6A) and 5-methyl-cytidine (m5C).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 1-methyl-pseudouridine, meaning that all uridine residues in the mRNA sequence are replaced with 1-methyl-pseudouridine. Similarly, a polynucleotide can be uniformly modified for any type of nucleoside residue present in the sequence by replacement with a modified residue such as those set forth above.

Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and nucleosides having a modified uridine include 1-methyl-pseudouridine (m1ψ), 1-ethyl-pseudouridine (e1ψ), 5-methoxy uridine, 2-thio uridine, 5-cyano uridine, 2'-O-methyl uridine and 4'-thio uridine.

In some embodiments, a modified nucleobase is a modified adenine. Exemplary nucleobases and nucleosides having a modified adenine include 7-deaza-adenine, 1-methyl-adenosine (m1A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ$_0$), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

Thus, in some embodiments, the RNA molecules of the invention comprise a 5'UTR element, an optionally codon optimized open reading frame, and a 3'UTR element, a poly(A) sequence and/or a polyadenylation signal wherein the RNA is not chemically modified.

In some embodiments, the modified nucleobase is a modified uracil. Exemplary nucleobases and nucleosides having a modified uracil include pseudouridine (x), pyridin-4-one ribonucleoside, 5-aza-uridine, 6-aza-uridine, 2-thio-5-aza-uridine, 2-thio-uridine (s$^2$U), 4-thio-uridine (s$^4$U), 4-thio-pseudouridine, 2-thio-pseudouridine, 5-hydroxy-uridine (ho$^5$U), 5-aminoallyl-uridine, 5-halo-uridine (e.g., 5-iodo-uridineor 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s$^2$U), 5-aminomethyl-2-thio-uridine (nm$^5$s$^2$U), 5-methylaminomethyl-uridine (mnm$^5$U), 5-methylaminomethyl-2-thio-uridine (mnm$^5$s$^2$U), 5-methylaminomethyl-2-seleno-uridine (mnm$^5$se$^2$U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s$^2$U), 5-propynyl-uridine, 1-propynyl-pseudouridine, 5-taurinomethyl-uridine (τm$^5$U), 1-taurinomethyl-pseudouridine, 5-taurinomethyl-2-thio-uridine(τm$^5$s$^2$U), 1-taurinomethyl-4-thio-pseudouridine, 5-methyl-uridine (m$^5$U, i.e., having the nucleobase deoxythymine), 1-methyl-pseudouridine (m$^1$ψ), 1-ethyl-pseudouridine (e1ψ), 5-methyl-2-thio-uridine (m$^5$s$^2$U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m⁵D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp³U), 1-methyl-3-(3-amino-3-carboxypropyl)pseudouridine (acp³ψ), 5-(isopentenylaminomethyl)uridine (inm⁵U), 5-(isopentenylaminomethyl)-2-thio-uridine (inm⁵s²U), α-thio-uridine, 2'-O-methyl-uridine (Um), 5,2'-O-dimethyl-uridine (m⁵Um), 2'-O-methyl-pseudouridine (ψm), 2-thio-2'-O-methyl-uridine (s²Um), 5-methoxycarbonylmethyl-2'-O-methyl-uridine (mcm⁵Um), 5-carbamoylmethyl-2'-O-methyl-uridine (ncm⁵Um), 5-carboxymethylaminomethyl-2'-O-methyl-uridine (cmnm⁵Um), 3,2'-O-dimethyl-uridine (m³Um), and 5-(isopentenylaminomethyl)-2'-O-methyl-uridine (inm⁵Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m³C), N4-acetyl-cytidine (ac⁴C), 5-formyl-cytidine (f⁵C), N4-methyl-cytidine (m⁴C), 5-methyl-cytidine (m⁵C), 5-halo-cytidine (e.g., 5-iodo-cytidine), 5-hydroxymethyl-cytidine (hm⁵C), 1-methyl-pseudoisocytidine, pyrrolo-cytidine, pyrrolo-pseudoisocytidine, 2-thio-cytidine (s²C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethyl-cytidine (m⁵Cm), N4-acetyl-2'-O-methyl-cytidine (ac⁴Cm), N4,2'-O-dimethyl-cytidine (m⁴Cm), 5-formyl-2'-O-methyl-cytidine (f⁵Cm), N4,N4,2'-O-trimethyl-cytidine (m⁴₂Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-di-aminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m¹A), 2-methyl-adenine (m²A), N6-methyl-adenosine (m⁶A), 2-methylthio-N6-methyl-adenosine (ms²m⁶A), N6-isopentenyl-adenosine (i⁶A), 2-methylthio-N6-isopentenyl-adenosine (ms²i⁶A), N6-(cis-hydroxyisopentenyl)adenosine (io⁶A), 2-methylthio-N6-(cis-hydroxyisopentenyl) adenosine (ms²io⁶A), N6-glycinylcarbamoyl-adenosine (g⁶A), N6-threonylcarbamoyl-adenosine (t⁶A), N6-methyl-N6-threonylcarbamoyl-adenosine (m⁶t⁶A), 2-methylthio-N6-threonylcarbamoyl-adenosine (ms²g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms²hn⁶A), N6-acetyl-adenosine (ac⁶A), 7-methyl-adenine, 2-methylthio-adenine, 2-methoxy-adenine, α-thio-adenosine, 2'-O-methyl-adenosine (Am), N6,2'-O-dimethyl-adenosine (m⁶Am), N6,N6,2'-O-trimethyl-adenosine (m⁶₂Am), 1,2'-O-dimethyl-adenosine (m¹Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine (m¹I), wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ₀), 7-aminomethyl-7-deaza-guanosine (preQ₁), archaeosine (G⁺), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methyl-guanosine (m¹G), N2-methyl-guanosine (m²G), N2,N2-dimethyl-guanosine (m²₂G), N2,7-dimethyl-guanosine (m²,⁷G), N2, N2,7-dimethyl-guanosine (m²,²,⁷G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m²Gm), N2,N2-dimethyl-2'-O-methyl-guanosine (m²₂Gm), 1-methyl-2'-O-methyl-guanosine (m¹Gm), N2,7-dimethyl-2'-O-methyl-guanosine (m²,⁷Gm), 2'-O-methyl-inosine (Im), 1,2'-O-dimethyl-inosine (m¹Im), 2'-O-ribosylguanosine (phosphate) (Gr(p)), 1-thio-guanosine, 06-methyl-guanosine, 2'-F-ara-guanosine, and 2'-F-guanosine.

In one embodiment, the polynucleotides of the present disclosure, such as IVT polynucleotides, may have a uniform chemical modification of all or any of the same nucleoside type or a population of modifications produced by mere downward titration of the same starting modification in all or any of the same nucleoside type, or a measured percent of a chemical modification of any of the same nucleoside type but with random incorporation, such as where all uridines are replaced by a uridine analog, e.g., pseudouridine. In another embodiment, the polynucleotides may have a uniform chemical modification of two, three, or four of the nucleoside types throughout the entire polynucleotide (such as both all uridines and all cytosines, etc. are modified in the same way). When the polynucleotides of the present disclosure are chemically and/or structurally modified, the polynucleotides may be referred to as "modified polynucleotides."

As used herein, the term "approximately" or "about," as applied to one or more values of interest, refers to a value that is similar to a stated reference value, as well as a collection or range of values that are included. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value.

In another embodiment, the term "about" refers to a range of values which are 1% more or less than the specified value.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl (benzyl)). An "alkylaryl" moiety is an aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ or $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups.

In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl such as benzo[d][1,3]dioxole-5-yl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, and [4.4.0] bicyclodecane and [2.2.2] bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl (e.g., benzo[d][1,3]dioxole-5-yl), morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula.

Combinations of substituents and/or variables are permissible, but only if such combinations result in stable compounds.

When any variable (e.g., $R_{29}$) occurs more than one time in any constituent or formula for a compound, its definition at each occurrence is independent of its definition at every other occurrence. Thus, for example, if a group is shown to contain 0-2 $R_{29}$ moieties, then the group may contain up to two $R_{29}$ moieties and $R_{29}$ at each occurrence is selected independently from the definition of $R_{29}$. Also, combinations of substituents and/or variables are permissible, but only if such combinations result in stable compounds.

The term "hydroxy" or "hydroxyl" includes groups with an —OH or —O—.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups.

The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to —NH$_2$. "Alkylamino" includes groups of compounds wherein the nitrogen of —NH$_2$ is bound to at least one alkyl group. Examples of alkylamino groups include benzylamino, methylamino, ethylamino, phenethylamino, etc. "Dialkylamino" includes groups wherein the nitrogen of —NH$_2$ is bound to two alkyl groups.

Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

The term "amine protecting group" refers to a protecting group for amines. Examples of amine protecting groups include but are not limited to fluorenylmethyloxycarbonyl ("Fmoc"), carboxybenzyl ("Cbz"), tert-butyloxycarbonyl ("BOC"), dimethoxybenzyl ("DMB"), acetyl ("Ac"), trifluoroacetyl, phthalimide, benzyl ("Bn"), Trityl (triphenylmethyl, Tr), benzylideneamine, Tosyl (Ts). See also Chem. Rev. 2009, 109, 2455-2504 for additional amine protecting groups, the contents of which are incoporated herein by reference in its entirety.

Compounds of the present disclosure that contain nitrogens can be converted to N-oxides by treatment with an oxidizing agent (e.g., 3-chloroperoxybenzoic acid (mCPBA) and/or hydrogen peroxides) to afford other compounds of the present disclosure. Thus, all shown and claimed nitrogen-containing compounds are considered, when allowed by valency and structure, to include both the compound as shown and its N-oxide derivative (which can be designated as N→O or N$^+$—O$^-$). Furthermore, in other instances, the nitrogens in the compounds of the present disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C$_1$-C$_6$ alkyl, C$_1$-C$_6$ alkenyl, C$_1$-C$_6$ alkynyl, 3-14-membered carbocycle or 3-14-membered heterocycle) derivatives.

In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present disclosure.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present disclosure may be depicted as different chiral isomers or geometric isomers. It should also be understood that when compounds have chiral isomeric or geometric isomeric forms, all isomeric forms are intended to be included in the scope of the present disclosure, and the naming of the compounds does not exclude any isomeric forms, it being understood that not all isomers may have the same level of activity.

Furthermore, the structures and other compounds discussed in this disclosure include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds.

Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. Examples of lactam-lactim tautomerism are as shown below.

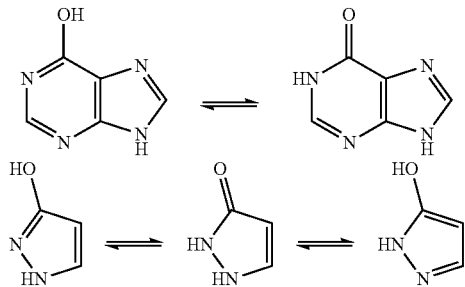

It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility.

Recrystallization solvent, rate of crystallization, storage temperature, and other factors may cause one crystal form to dominate. Crystal polymorphs of the compounds can be prepared by crystallization under different conditions.

The compounds of any formula described herein include the compounds themselves, as well as their salts, and their solvates, if applicable.

A salt, for example, can be formed between an anion and a positively charged group (e.g., amino) on a compound or a polynucleotide (e.g., mRNA) disclosed herein. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). Suitable anions include pharmaceutically acceptable anions. The term "pharmaceutically acceptable anion" refers to an anion suitable for forming a pharmaceutically acceptable salt. Likewise, a salt can also be formed between a cation and a negatively charged group (e.g., carboxylate) on a compound or a polynucleotide (e.g., mRNA) disclosed herein.

Suitable cations include sodium ion, potassium ion, magnesium ion, calcium ion, and an ammonium cation such as tetramethylammonium ion. The compounds and polynucleotides (e.g., mRNA) disclosed herein may also include those salts containing quaternary nitrogen atoms.

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate.

Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by formula (I) are modified mRNA caps with the ribose group replaced with a 6-membered cyclic structure, and have formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, Chem. Rev. 96, 3147-3176, 1996.

The present disclosure is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

For example, when a certain variable (e.g., any of $R_{20}$-$R_{23}$) in formula (I) is H or hydrogen, it can be either hydrogen or deuterium.

The use of the articles "a", "an", and "the" in both the following description and claims are to be construed to cover both the singular and the plural, unless otherwise indicated herein or clearly contradicted by context. The terms "comprising", "having", "being of" as in "being of a chemical formula", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

As used herein, the expressions "one or more of A, B, or C," "one or more A, B, or C," "one or more of A, B, and C," "one or more A, B, and C" and the like are used interchangeably and all refer to a selection from a group consisting of A, B, and/or C, i.e., one or more As, one or more Bs, one or more Cs, or any combination thereof.

The present disclosure provides methods for the synthesis of the compounds of any of the formulae described herein. The present disclosure also provides detailed methods for the synthesis of various disclosed compounds according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the disclosure can tolerate a wide variety of functional groups, therefore various substituted starting materials can be used. The processes generally provide the desired final compound at or near the end of the overall process, although it may be desirable in certain instances to further convert the compound to a pharmaceutically acceptable salt thereof.

Compounds of the present disclosure can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure,* 5$^{th}$ edition, John Wiley & Sons: New York, 2001; Greene, T. W., Wuts, P. G. M., *Protective Groups in Organic Synthesis,* 3$^{rd}$ edition, John Wiley & Sons: New York, 1999; R. Larock, *Comprehensive Organic Transformations,* VCH Publishers (1989); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present disclosure.

The compounds of this disclosure having any of the formulae described herein may be prepared according to the procedures illustrated in Schemes 1-3 below, from commercially available starting materials or starting materials which can be prepared using literature procedures. The variables (e.g., $Y_2$) in the scheme are as defined herein for formula (I) unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P. G. M., *Protective Groups in Organic Synthesis,* 3$^{rd}$ edition, John Wiley & Sons: New York, 1999.

Preferred protecting groups include, but are not limited to:

For a hydroxyl moiety: TBS, benzyl, THP, Ac

For carboxylic acids: benzyl ester, methyl ester, ethyl ester, allyl ester

For amines: Fmoc, Cbz, BOC, DMB, Ac, Bn, Tr, Ts, trifluoroacetyl, phthalimide, benzylideneamine For diols: Ac (×2) TBS (×2), or when taken together acetonides For thiols: Ac For benzimidazoles: SEM, benzyl, PMB, DMB For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

Scheme 1
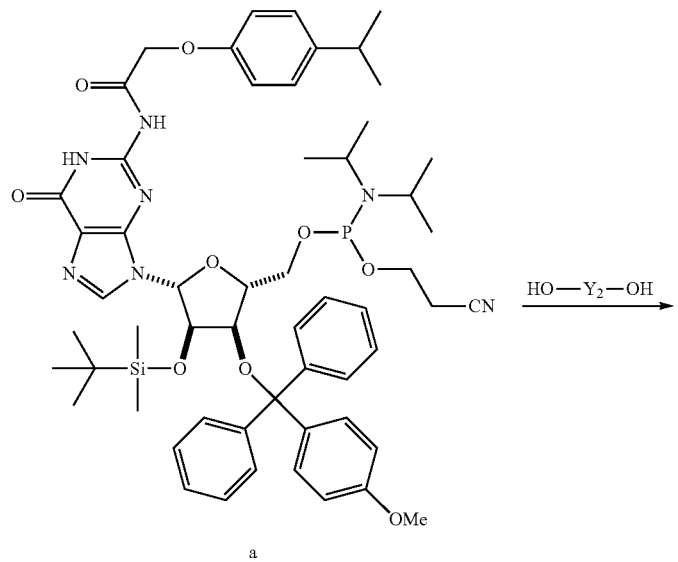
a
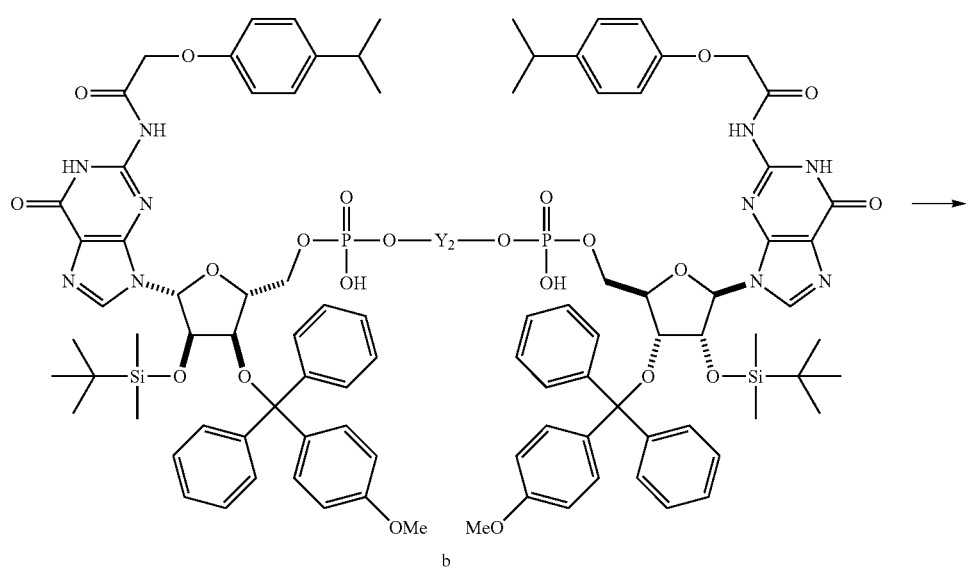
b
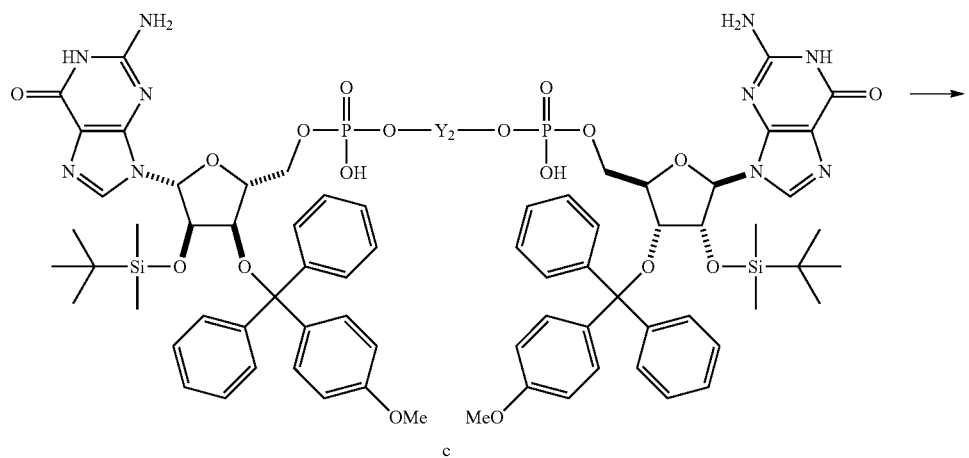
c

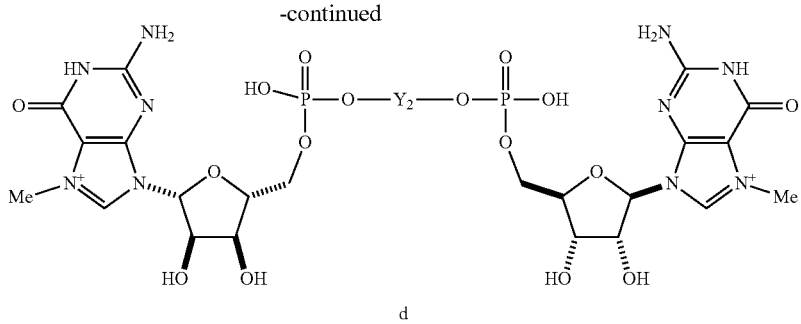

d

As illustrated in Scheme 1 above, commercially available phosphoramidite (a) is condensed under acidic conditions with the appropriate diol HO—$Y_2$—OH (e.g., ethylene glycol). The initial ratio of phosphoramidite-to-diol is equimolar, and the formation of the mono-substituted P(III) ester is monitored by LCMS. As the addition is found to be complete, additional 1 molar equivalent of phosphoramidite (a) is added. The resulting bis-P(III)-phosphodiester is oxidized with tert-butyl hydroperoxide. Treatment with base, such as diethylamine, induces a β-elimination of the cyanoethyl groups to yield the bis-phosphate ester (b). Treatment with a nucleophilic base, such as methylamine, induces removal of the amide protecting groups to yield (c) and this is followed by fluoride-mediated 2'-O-de-silylation. Acid treatment (TFA) completes the global deprotection and the final bis-N-7-methylation afforded the final compound (d).

Scheme 2

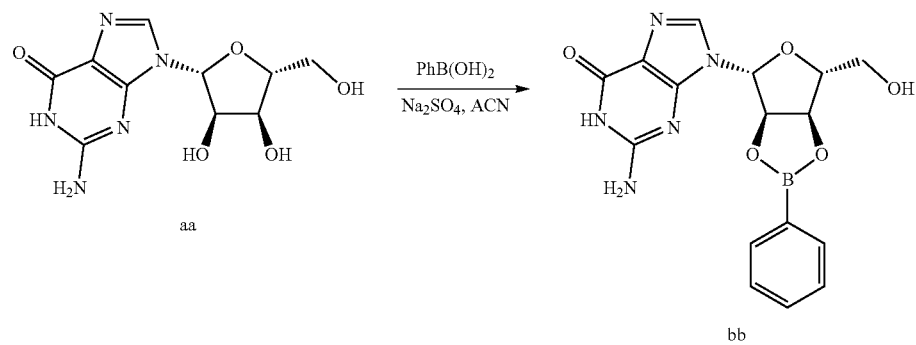

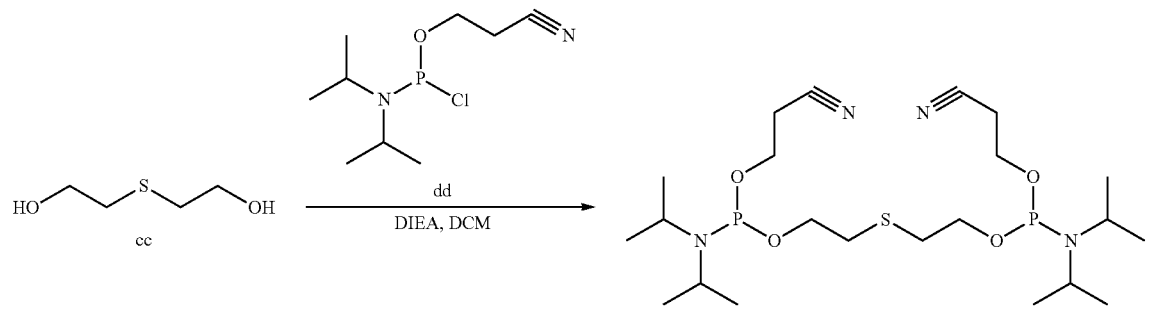

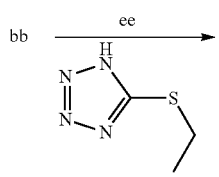

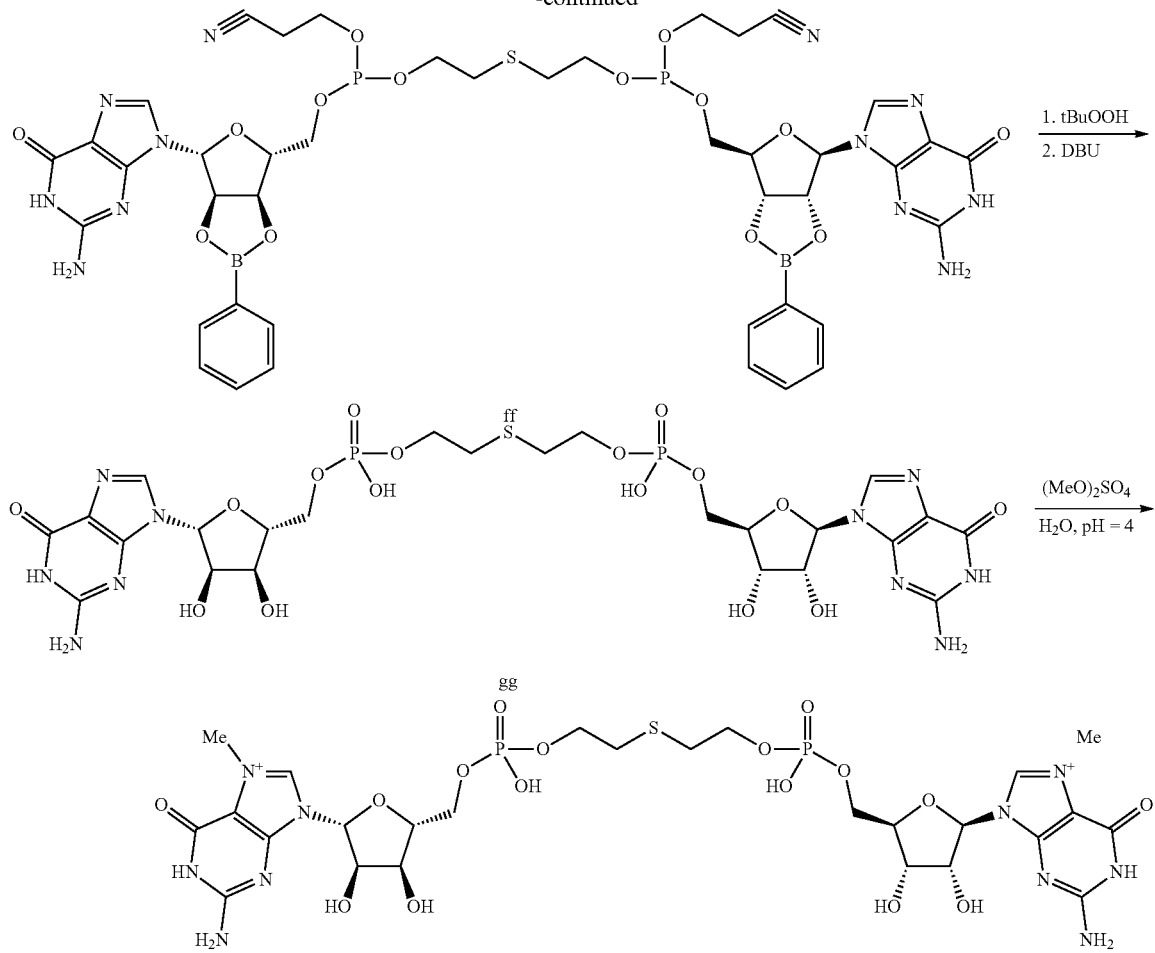

Scheme 2 above illustrates an alternative approach to synthesizing the compounds described herein. According to this, guanosine (aa) is converted to the labile 2'-3'-phenyl-boronate (bb), which is condensed with the bis-phosphoramidite (ee). The primary adduct (ff) is oxidized to the respective phosphotriester (gg), and the protecting groups are sequentially removed. The compound can be purified by ion-exchange chromatography and a symmetrical N7-methylation produces Compound 3.

Scheme 3

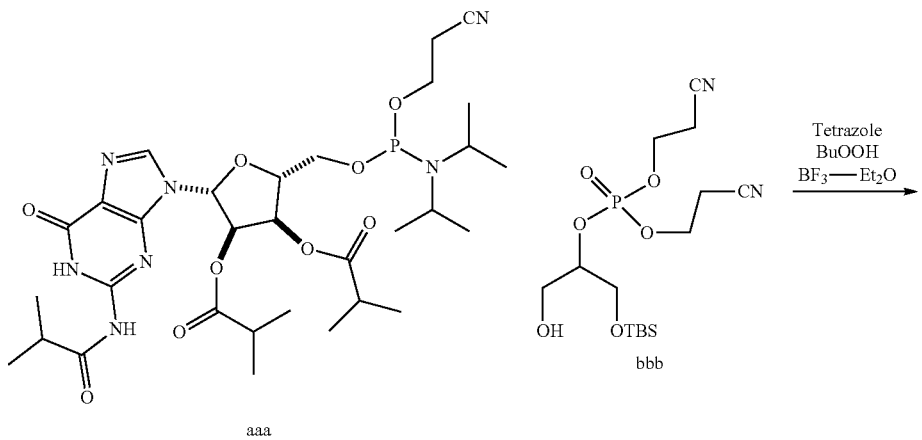

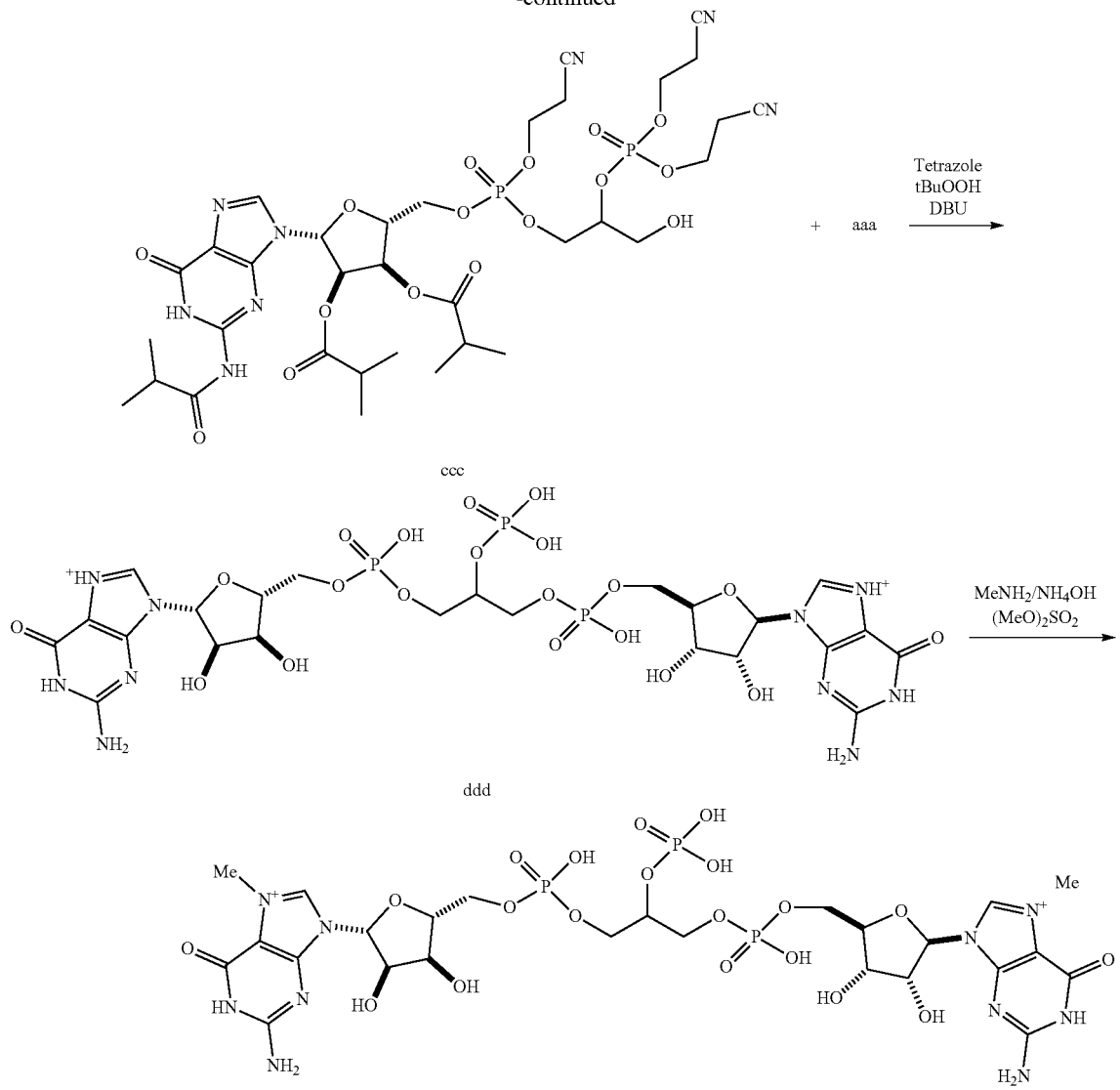

Scheme 3 above illustrates an approach to synthesizing the compounds described herein. Phosphoramidite (aaa) and bis(2-cyanoethyl) phosphate (bbb) are coupled to form (bis (2-cyanoethoxy)phosphoryl)oxy)-hydroxypropyl(cyanoethyl)phosphate (ccc), which is then coupled with another 1 molar equivalent of phosphoramidite (aaa) to yield the primary adduct (ddd). A symmetrical N7-methylation of ddd produces Compound 7. The compound can be purified by reverse phase chromatography.

A person of ordinary skill in the art will recognize that in the above schemes the order of certain steps may be interchangeable.

Cap analogs described herein are used for the synthesis of 5' capped RNA molecules in in vitro transcription reactions. Substitution of cap analog for a portion of the GTP in a transcription reaction results in the incorporation of the cap structure into a corresponding fraction of the transcripts. Capped mRNAs are generally translated more efficiently in reticulocyte lysate and wheat germ in vitro translation systems. It is important that in vitro transcripts be capped for microinjection experiments because uncapped mRNAs are rapidly degraded. Cap analogs are also used as a highly specific inhibitor of the initiation step of protein synthesis.

Accordingly, in another aspect, the present disclosure provides methods of synthesizing an RNA molecule in vitro. The method can include reacting unmodified or modified ATP, unmodified or modified CTP, unmodified or modified UTP, unmodified or modified GTP, a compound of formula (I) or a stereoisomer, tautomer or salt thereof, and a polynucleotide template; in the presence an RNA polymerase; under a condition conducive to transcription by the RNA polymerase of the polynucleotide template into one or more RNA copies; whereby at least some of the RNA copies incorporate the compound of formula (I) or a stereoisomer, tautomer or salt thereof to make an RNA molecule.

Also provided herein is a kit for capping an RNA transcript. The kit includes a compound of formula (I) and an RNA polymerase. The kit may also include one or more of nucleotides, ribonuclease inhibitor, an enzyme buffer, and an nucleotide buffer.

In another aspect, the RNA molecule may be capped post-transcriptionally. For example, recombinant vaccinia virus capping enzyme and recombinant 2'-O-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-O-methyl.

In yet another aspect, the present disclosure provides an RNA molecule (e.g., mRNA) whose 5' end comprises a compound (e.g., a cap analog) disclosed herein. For example, the 5' end of the RNA molecule comprises a compound of formula (III), (IIIa) or (IIIb):

structure as that of a natural RNA or mRNA molecule. In other embodiments, the RNA and mRNA of the disclosure, in addition to the modifications on the 5' end cap disclosed herein, may include at least one chemical modification as described herein.

Generally, the length of the IVT polynucleotide (e.g., IVT mRNA) encoding a polypeptide of interest is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000,

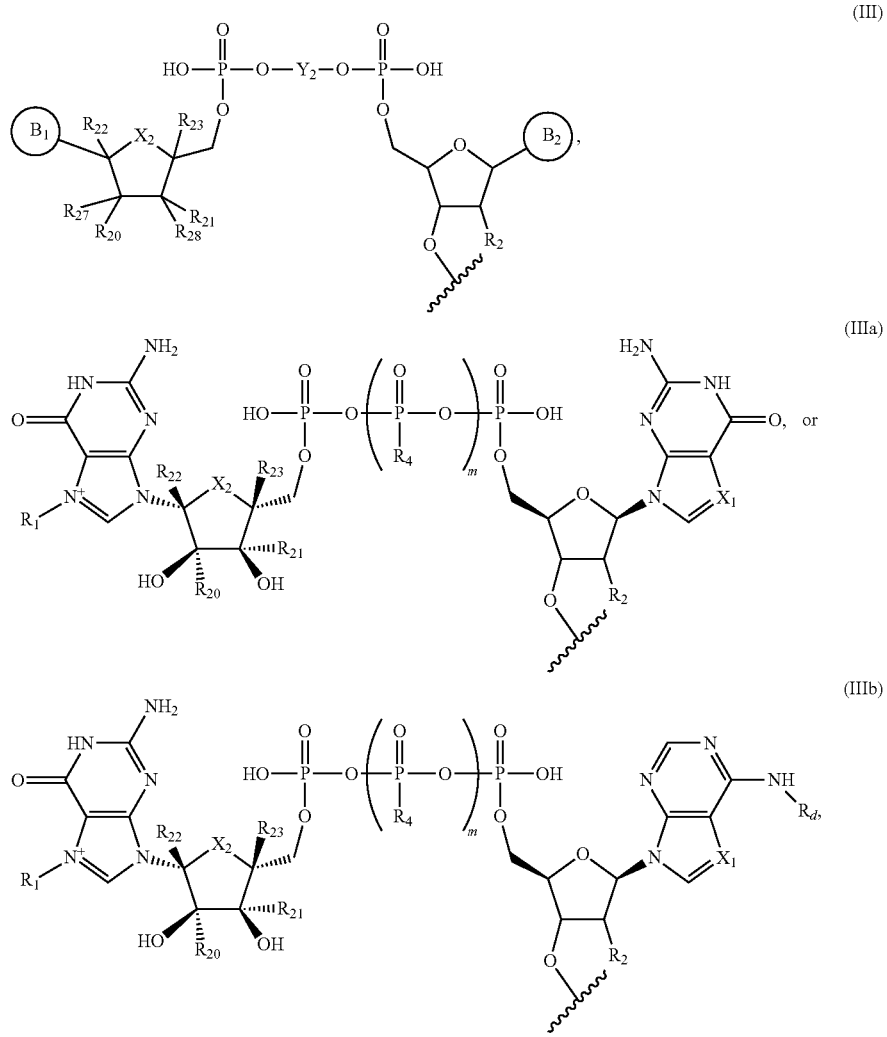

wherein the wavy line indicates the attachment point to the rest of the RNA molecule.

In embodiments, the variables in formulae (III), (IIIa) and (IIIb) are as defined herein for formula (I), where applicable.

In embodiments, the RNA molecule is an mRNA molecule.

In embodiments, the RNA molecule is an in vitro transcribed mRNA molecule (IVT mRNA).

In some embodiments, the RNA and mRNA of the disclosure, except for the 5' end cap thereof, is an unmodified RNA or mRNA molecule which has the same sequence and 7,000, 8,000, 9,000, 10,000, 20,000, 30,000, 40,000, 50,000, 60,000, 70,000, 80,000, 90,000 or up to and including 100,000 nucleotides).

In some embodiments, the IVT polynucleotide (e.g., IVT mRNA) includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, or from 2,000 to 100,000 nucleotides).

In some embodiments, a nucleic acid as described herein is a chimeric polynucleotide. Chimeric polynucleotides, or RNA constructs, maintain a modular organization similar to IVT polynucleotides, but the chimeric polynucleotides comprise one or more structural and/or chemical modifications or alterations which impart useful properties to the polynucleotide. As such, the chimeric polynucleotides which are modified mRNA molecules of the present disclosure are termed "chimeric modified mRNA" or "chimeric mRNA." Chimeric polynucleotides have portions or regions which differ in size and/or chemical modification pattern, chemical modification position, chemical modification percent or chemical modification population and combinations of the foregoing.

In embodiments, the RNA and mRNA of the disclosure is a component of a multimeric mRNA complex.

In another aspect, the disclosure also provides a method of producing a multimeric mRNA complex. In some embodiments, a multimeric mRNA complex is formed by a heating and stepwise cooling protocol. For example, a mixture of 5 μM of each mRNA desired to be incorporated into the multimeric complex can be placed in a buffer containing 50 mM 2-Amino-2-hydroxymethyl-propane-1,3-diol (Tris) pH 7.5, 150 mM sodium chloride (NaCl), and 1 mM ethylene-diamine-tetra-acetic acid (EDTA). The mixture can be heated to 65° C. for 5 minutes, 60° C. for 5 minutes, 40° C. for 2 minutes, and then cooled to 4° C. for 10 minutes, resulting in the formation of a multimeric complex.

In embodiments, the RNA and mRNA of the disclosure are substantially non-toxic and non-mutagenic.

In some embodiments, the RNA and mRNA of the disclosure, when introduced to a cell, may exhibit reduced degradation in the cell, as compared to a natural polynucleotide.

As described herein, the polynucleotides (e.g., mRNA) of the disclosure preferably do not substantially induce an innate immune response of a cell into which the polynucleotide (e.g., mRNA) is introduced. Features of an induced innate immune response include 1) increased expression of pro-inflammatory cytokines, 2) activation of intracellular PRRs (RIG-I, MDA5, etc., and/or 3) termination or reduction in protein translation.

In some embodiments, nucleic acids disclosed herein include a first region of linked nucleosides encoding a polypeptide of interest (e.g., a coding region), a first flanking region located at the 5'-terminus of the first region (e.g., a 5'-UTR), a second flanking region located at the 3'-terminus of the first region (e.g., a 3'-UTR), at least one 5'-cap region, and a 3'-stabilizing region. In some embodiments, a nucleic acid or polynucleotide further includes a poly-A region or a Kozak sequence (e.g., in the 5'-UTR). In some cases, polynucleotides may contain one or more intronic nucleotide sequences capable of being excised from the polynucleotide. In some embodiments, a polynucleotide or nucleic acid (e.g., an mRNA) may include a 5' cap structure, a chain terminating nucleotide, a stem loop, a polyA sequence, and/or a polyadenylation signal. In some embodiments, any one of the regions of the polynucleotides of the disclosure includes at least one alternative nucleoside. For example, the 3'-stabilizing region may contain an alternative nucleoside such as an L-nucleoside, an inverted thymidine, or a 2'-O-methyl nucleoside and/or the coding region, 5'-UTR, 3'-UTR, or cap region may include an alternative nucleoside such as a 5-substituted uridine (e.g., 5-methoxyuridine), a 1-substituted pseudouridine (e.g., 1-methyl-pseudouridine), and/or a 5-substituted cytidine (e.g., 5-methyl-cytidine).

Generally, the shortest length of a polynucleotide can be the length of the polynucleotide sequence that is sufficient to encode for a dipeptide. In another embodiment, the length of the polynucleotide sequence is sufficient to encode for a tripeptide. In another embodiment, the length of the polynucleotide sequence is sufficient to encode for a tetrapeptide. In another embodiment, the length of the polynucleotide sequence is sufficient to encode for a pentapeptide. In another embodiment, the length of the polynucleotide sequence is sufficient to encode for a hexapeptide. In another embodiment, the length of the polynucleotide sequence is sufficient to encode for a heptapeptide. In another embodiment, the length of the polynucleotide sequence is sufficient to encode for an octapeptide. In another embodiment, the length of the polynucleotide sequence is sufficient to encode for a nonapeptide. In another embodiment, the length of the polynucleotide sequence is sufficient to encode for a decapeptide.

Examples of dipeptides that the alternative polynucleotide sequences can encode for include, but are not limited to, carnosine and anserine.

In some cases, a polynucleotide is greater than 30 nucleotides in length. In another embodiment, the polynucleotide molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 50 nucleotides. In another embodiment, the length is at least 60 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

Nucleic acids and polynucleotides disclosed herein may include one or more naturally occurring components, including any of the canonical nucleotides A (adenosine), G (guanosine), C (cytosine), U (uridine), or T (thymidine). In one embodiment, all or substantially of the nucleotides comprising (a) the 5'-UTR, (b) the open reading frame (ORF), (c) the 3'-UTR, (d) the poly A tail, and any combination of (a, b, c or d above) comprise naturally occurring canonical nucleotides A (adenosine), G (guanosine), C (cytosine), U (uridine), or T (thymidine).

Nucleic acids and polynucleotides disclosed herein may include one or more alternative components (e.g., in a 3'-stabilizing region), as described herein, which impart useful properties including increased stability and/or the lack of a substantial induction of the innate immune response of a cell into which the polynucleotide is introduced. For example, a modified (e.g., altered or alternative) polynucleotide or nucleic acid exhibits reduced degradation in a cell into which the polynucleotide or nucleic acid is introduced, relative to a corresponding unaltered polynucleotide or nucleic acid. These alternative species may enhance the efficiency of protein production, intracellular retention of the polynucleotides, and/or viability of contacted cells, as well as possess reduced immunogenicity.

Polynucleotides and nucleic acids may be naturally or non-naturally occurring. Polynucleotides and nucleic acids may include one or more modified (e.g., altered or alternative) nucleobases, nucleosides, nucleotides, or combinations thereof. The nucleic acids and polynucleotides disclosed herein can include any suitable modification or alteration, such as to the nucleobase, the sugar, or the internucleoside linkage (e.g., to a linking phosphate/to a phosphodiester linkage/to the phosphodiester backbone). In certain embodiments, alterations (e.g., one or more alterations) are present in each of the nucleobase, the sugar, and the internucleoside linkage. Alterations according to the present disclosure may be alterations of ribonucleic acids (RNAs) to deoxyribonucleic acids (DNAs), e.g., the substitution of the 2'-OH of the ribofuranosyl ring to 2'-H, threose nucleic acids (TNAs), glycol nucleic acids (GNAs), peptide nucleic acids (PNAs), locked nucleic acids (LNAs), or hybrids thereof. Additional alterations are described herein.

Polynucleotides and nucleic acids may or may not be uniformly altered along the entire length of the molecule. For example, one or more or all types of nucleotide (e.g., purine or pyrimidine, or any one or more or all of A, G, U, C) may or may not be uniformly altered in a polynucleotide or nucleic acid, or in a given predetermined sequence region thereof. In some instances, all nucleotides X in a polynucleotide of the disclosure (or in a given sequence region thereof) are altered, wherein X may any one of nucleotides A, G, U, C, or any one of the combinations A+G, A+U, A+C, G+U, G+C, U+C, A+G+U, A+G+C, G+U+C or A+G+C.

Different sugar alterations and/or internucleoside linkages (e.g., backbone structures) may exist at various positions in the polynucleotide. One of ordinary skill in the art will appreciate that the nucleotide analogs or other alteration(s) may be located at any position(s) of a polynucleotide such that the function of the polynucleotide is not substantially decreased. An alteration may also be a 5'- or 3'-terminal alteration. In some embodiments, the polynucleotide includes an alteration at the 3'-terminus. The polynucleotide may contain from about 1% to about 100% alternative nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of A, G, U, or C.

The polynucleotides may contain at a minimum one and at maximum 100% alternative nucleotides, or any intervening percentage, such as at least 5% alternative nucleotides, at least 10% alternative nucleotides, at least 25% alternative nucleotides, at least 50% alternative nucleotides, at least 80% alternative nucleotides, or at least 90% alternative nucleotides. For example, the polynucleotides may contain an alternative pyrimidine such as an alternative uracil or cytosine. In some embodiments, at least 5%, at least 10%, at least 25%, at least 50%, at least 80%, at least 90% or 100% of the uracil in the polynucleotide is replaced with an alternative uracil (e.g., a 5-substituted uracil). The alternative uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with an alternative cytosine (e.g., a 5-substituted cytosine). The alternative cytosine can be replaced by a compound having a single unique structure, or can be replaced by a plurality of compounds having different structures (e.g., 2, 3, 4 or more unique structures).

In certain embodiments, it may be desirable for an RNA molecule (e.g., mRNA) introduced into the cell to be degraded intracellularly. For example, degradation of an RNA molecule may be preferable if precise timing of protein production is desired. Thus, in some embodiments, the disclosure provides an RNA molecule containing a degradation domain, which is capable of being acted on in a directed manner within a cell.

The term "polynucleotide," in its broadest sense, includes any compound and/or substance that is or can be incorporated into an oligonucleotide chain. Exemplary polynucleotides for use in accordance with the present disclosure include, but are not limited to, one or more of DNA, RNA including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein. In some embodiments, the polynucleotides may include one or more messenger RNAs (mRNAs) having one or more modified nucleoside or nucleotides (i.e., unnatural mRNA molecules).

In some embodiments, a nucleic acid (e.g. mRNA) molecule, formula, composition or method associated therewith comprises one or more polynucleotides comprising features as described in WO2002/098443, WO2003/051401, WO2008/052770, WO2009127230, WO2006122828, WO2008/083949, WO2010088927, WO2010/037539, WO2004/004743, WO2005/016376, WO2006/024518, WO2007/095976, WO2008/014979, WO2008/077592, WO2009/030481, WO2009/095226, WO2011069586, WO2011026641, WO2011/144358, WO2012019780, WO2012013326, WO2012089338, WO2012113513, WO2012116811, WO2012116810, WO2013113502, WO2013113501, WO2013113736, WO2013143698, WO2013143699, WO2013143700, WO2013/120626, WO2013120627, WO2013120628, WO2013120629, WO2013174409, WO2014127917, WO2015/024669, WO2015/024668, WO2015/024667, WO2015/024665, WO2015/024666, WO2015/024664, WO2015101415, WO2015101414, WO2015024667, WO2015062738, WO2015101416, the contents of each of which are incorporated by reference herein.

Nucleobase Alternatives

The alternative nucleosides and nucleotides can include an alternative nucleobase. A nucleobase of a nucleic acid is an organic base such as a purine or pyrimidine or a derivative thereof. A nucleobase may be a canonical base (e.g., adenine, guanine, uracil, thymine, and cytosine). These nucleobases can be altered or wholly replaced to provide polynucleotide molecules having enhanced properties, e.g., increased stability such as resistance to nucleases. Non-canonical or modified bases may include, for example, one or more substitutions or modifications including but not limited to alkyl, aryl, halo, oxo, hydroxyl, alkyloxy, and/or thio substitutions; one or more fused or open rings; oxidation; and/or reduction.

Alternative nucleotide base pairing encompasses not only the standard adenine-thymine, adenine-uracil, or guanine-cytosine base pairs, but also base pairs formed between nucleotides and/or alternative nucleotides including non-standard or alternative bases, wherein the arrangement of hydrogen bond donors and hydrogen bond acceptors permits hydrogen bonding between a non-standard base and a standard base or between two complementary non-standard base structures. One example of such non-standard base pairing is the base pairing between the alternative nucleotide inosine and adenine, cytosine, or uracil.

In some embodiments, the nucleobase is an alternative uracil. Exemplary nucleobases and nucleosides having an alternative uracil include pseudouridine (ψ), pyridin-4-one ribonucleoside, 5-aza-uracil, 6-aza-uracil, 2-thio-5-aza-uracil, 2-thio-uracil ($s^2U$), 4-thio-uracil ($s^4U$), 4-thio-pseudouridine, 2-thio-pseudouridine, 5-hydroxy-uracil ($ho^5U$), 5-aminoallyl-uracil, 5-halo-uracil (e.g., 5-iodo-uracil or 5-bromo-uracil), 3-methyl-uracil ($m^3U$), 5-methoxy-uracil ($mo^5U$), uracil 5-oxyacetic acid ($cmo^5U$), uracil 5-oxyacetic acid methyl ester ($mcmo^5U$), 5-carboxymethyl-uracil ($cm^5U$), 1-carboxymethyl-pseudouridine, 5-carboxyhydroxymethyl-uracil ($chm^5U$), 5-carboxyhydroxymethyl-uracil methyl ester ($mchm^5U$), 5-methoxycarbonylmethyl-uracil ($mcm^5U$), 5-methoxycarbonylmethyl-2-thio-uracil ($mcm^5s^2U$), 5-aminomethyl-2-thio-uracil ($nm^5s^2U$), 5-methylaminomethyl-uracil ($mnm^5U$), 5-methylaminomethyl-2-thio-uracil ($mnm^5s^2U$), 5-methylaminomethyl-2-seleno-uracil ($mnm^5se^2U$), 5-carbamoylmethyl-uracil ($ncm^5U$), 5-carboxymethylaminomethyl-uracil ($cmnm^5U$), 5-carboxymethylaminomethyl-2-thio-uracil ($cmnm^5s^2U$), 5-propynyl-uracil, 1-propynyl-pseudouracil, 5-taurinomethyl-uracil ($τm^5U$), 1-taurinomethyl-pseudouridine, 5-taurinomethyl-2-thio-uracil($τm^5s^2U$), 1-taurinomethyl-4-thio-pseudouridine, 5-methyl-uracil ($m^5U$, i.e., having the nucleobase deoxythymine), 1-methyl-pseudouridine ($m^1ψ$), 5-methyl-2-thio-uracil ($m^5s^2U$), 1-methyl-4-thio-pseudouridine ($m^1s^4ψ$), 4-thio-1-methyl-pseudouridine, 3-methyl-pseudouridine ($m^3ψ$), 2-thio-1-methyl-pseudouridine, 1-methyl-1-deaza-pseudouridine, 2-thio-1-methyl-1-deaza-pseudouridine, dihydrouracil (D), dihydropseudouridine, 5,6-dihydrouracil, 5-methyl-dihydrouracil ($m^5D$), 2-thio-dihydrouracil, 2-thio-dihydropseudouridine, 2-methoxy-uracil, 2-methoxy-4-thio-uracil, 4-methoxy-pseudouridine, 4-methoxy-2-thio-pseudouridine, N1-methyl-pseudouridine, 3-(3-amino-3-carboxypropyl)uracil ($acp^3U$), 1-methyl-3-(3-amino-3-carboxypropyl)pseudouridine ($acp^3ψ$), 5-(isopentenylaminomethyl)uracil ($inm^5U$), 5-(isopentenylaminomethyl)-2-thio-uracil ($inm^5s^2U$), 5,2'-O-dimethyl-uridine ($m^5Um$), 2-thio-2'-O_methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), and 5-(isopentenylaminomethyl)-2'-O-methyl-uridine ($inm^5Um$), 1-thio-uracil, deoxythymidine, 5-(2-carbomethoxyvinyl)-uracil, 5-(carbamoylhydroxymethyl)-uracil, 5-carbamoylmethyl-2-thio-uracil, 5-carboxymethyl-2-thio-uracil, 5-cyanomethyl-uracil, 5-methoxy-2-thio-uracil, and 5-[3-(1-E-propenylamino)]uracil.

In some embodiments, the nucleobase is an alternative cytosine. Exemplary nucleobases and nucleosides having an alternative cytosine include 5-aza-cytosine, 6-aza-cytosine, pseudoisocytidine, 3-methyl-cytosine (m3C), N4-acetyl-cytosine (ac4C), 5-formyl-cytosine (f5C), N4-methyl-cytosine (m4C), 5-methyl-cytosine (m5C), 5-halo-cytosine (e.g., 5-iodo-cytosine), 5-hydroxymethyl-cytosine (hm5C), 1-methyl-pseudoisocytidine, pyrrolo-cytosine, pyrrolo-pseudoisocytidine, 2-thio-cytosine (s2C), 2-thio-5-methyl-cytosine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytosine, 2-methoxy-5-methyl-cytosine, 4-methoxy-pseudoisocytidine, 4-methoxy-1-methyl-pseudoisocytidine, lysidine (k2C), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytosine, 5-hydroxy-cytosine, 5-(3-azidopropyl)-cytosine, and 5-(2-azidoethyl)-cytosine.

In some embodiments, the nucleobase is an alternative adenine. Exemplary nucleobases and nucleosides having an alternative adenine include 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenine (m1A), 2-methyl-adenine (m2A), N6-methyl-adenine (m6A), 2-methylthio-N6-methyl-adenine (ms2m6A), N6-isopentenyl-adenine (i6A), 2-methylthio-N6-isopentenyl-adenine (ms2i6A), N6-(cis-hydroxyisopentenyl)adenine (io6A), 2-methylthio-N6-

(cis-hydroxyisopentenyl)adenine (ms2io6A), N6-glycinyl-carbamoyl-adenine (g6A), N6-threonylcarbamoyl-adenine (t6A), N6-methyl-N6-threonylcarbamoyl-adenine (m6t6A), 2-methylthio-N6-threonylcarbamoyl-adenine (ms2g6A), N6,N6-dimethyl-adenine (m62A), N6-hydroxynorvalylcar-bamoyl-adenine (hn6A), 2-methylthio-N6-hydroxynorva-lylcarbamoyl-adenine (ms2hn6A), N6-acetyl-adenine (ac6A), 7-methyl-adenine, 2-methylthio-adenine, 2-methoxy-adenine, N6,2'-O-dimethyl-adenosine (m6Am), N6,N6,2'-O-trimethyl-adenosine (m62Am), 1,2'-O-dim-ethyl-adenosine (m1Am), 2-amino-N6-methyl-purine, 1-thio-adenine, 8-azido-adenine, N6-(19-amino-pentaox-anonadecyl)-adenine, 2,8-dimethyl-adenine, N6-formyl-ad-enine, and N6-hydroxymethyl-adenine.

In some embodiments, the nucleobase is an alternative guanine. Exemplary nucleobases and nucleosides having an alternative guanine include inosine (I), 1-methyl-inosine (m1I), wyosine (imG), methylwyosine (mimG), 4-dem-ethyl-wyosine (imG-14), isowyosine (imG2), wybutosine (yW), peroxywybutosine (o2yW), hydroxywybutosine (OHyW), undermodified hydroxywybutosine (OHyW*), 7-deaza-guanine, queuosine (Q), epoxyqueuosine (oQ), galactosyl-queuosine (galQ), mannosyl-queuosine (manQ), 7-cyano-7-deaza-guanine (preQ$_0$), 7-aminomethyl-7-deaza-guanine (preQ1), archaeosine (G+), 7-deaza-8-aza-guanine, 6-thio-guanine, 6-thio-7-deaza-guanine, 6-thio-7-deaza-8-aza-guanine, 7-methyl-guanine (m7G), 6-thio-7-methyl-guanine, 7-methyl-inosine, 6-methoxy-guanine, 1-methyl-guanine (m1G), N2-methyl-guanine (m2G), N2,N2-dimethyl-guanine (m22G), N2,7-dimethyl-guanine (m2,7G), N2, N2,7-dimethyl-guanine (m2,2,7G), 8-oxo-guanine, 7-methyl-8-oxo-guanine, 1-methyl-6-thio-guanine, N2-methyl-6-thio-guanine, N2,N2-dimethyl-6-thio-gua-nine, N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 1-thio-guanine, and O-6-methyl-guanine.

The alternative nucleobase of a nucleotide can be inde-pendently a purine, a pyrimidine, a purine or pyrimidine analog. For example, the nucleobase can be an alternative to adenine, cytosine, guanine, uracil, or hypoxanthine. In another embodiment, the nucleobase can also include, for example, naturally-occurring and synthetic derivatives of a base, including pyrazolo[3,4-d]pyrimidines, 5-methylcyto-sine (5-me-C), 5-hydroxymethyl cytosine, xanthine, hypox-anthine, 2-aminoadenine, 6-methyl and other alkyl deriva-tives of adenine and guanine, 2-propyl and other alkyl derivatives of adenine and guanine, 2-thiouracil, 2-thiothy-mine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thio-alkyl, 8-hydroxy and other 8-substituted adenines and gua-nines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaade-nine, 7-deazaadenine, 3-deazaadenine, pyrazolo[3,4-d]py-rimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; or 1,3,5 triazine. When the nucleotides are depicted using the shorthand A, G, C, T or U, each letter refers to the representative base and/or derivatives thereof, e.g., A includes adenine or adenine analogs, e.g., 7-deaza adenine).

Alterations on the Sugar

Nucleosides include a sugar molecule (e.g., a 5-carbon or 6-carbon sugar, such as pentose, ribose, arabinose, xylose, glucose, galactose, or a deoxy derivative thereof) in com-bination with a nucleobase, while nucleotides are nucleo-sides containing a nucleoside and a phosphate group or alternative group (e.g., boranophosphate, thiophosphate, selenophosphate, phosphonate, alkyl group, amidate, and glycerol). A nucleoside or nucleotide may be a canonical species, e.g., a nucleoside or nucleotide including a canoni-cal nucleobase, sugar, and, in the case of nucleotides, a phosphate group, or may be an alternative nucleoside or nucleotide including one or more alternative components. For example, alternative nucleosides and nucleotides can be altered on the sugar of the nucleoside or nucleotide. In some embodiments, the alternative nucleosides or nucleotides include the structure:

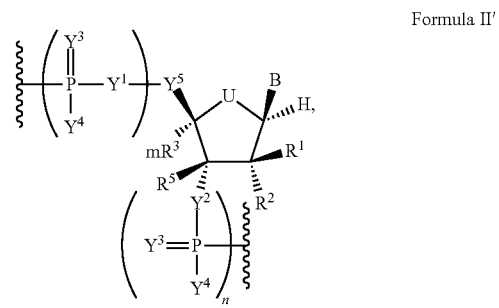

Formula II'

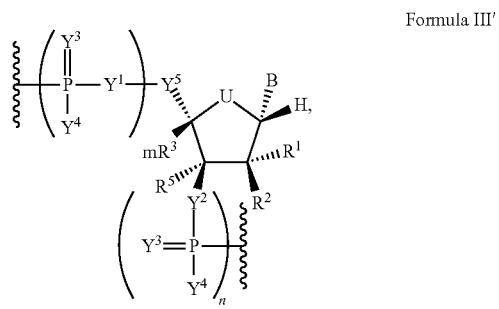

Formula III'

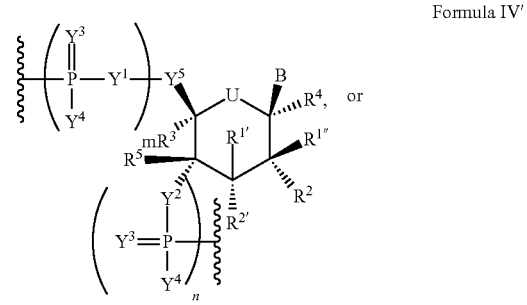

Formula IV'

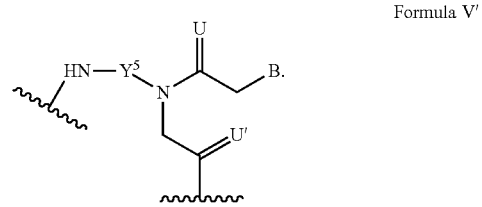

Formula V'

In each of the Formulae II', III', IV' and V',
each of m and n is independently, an integer from 0 to 5,
each of U and U' independently, is O, S, N(R$^U$)$_{nu}$, or C(R$^U$)$_{nu}$, wherein nu is an integer from 0 to 2 and each R$^U$ is, independently, H, halo, or optionally substituted alkyl;

each of $R^{1'}$, $R^{2'}$, $R^{1''}$, $R^{2''}$, $R^1$, $R^2$, $R^3$, $R^4$, and $R^5$ is, independently, if present, H, halo, hydroxy, thiol, optionally substituted alkyl, optionally substituted alkoxy, optionally substituted alkenyloxy, optionally substituted alkynyloxy, optionally substituted aminoalkoxy, optionally substituted alkoxyalkoxy, optionally substituted hydroxyalkoxy, optionally substituted amino, azido, optionally substituted aryl, optionally substituted aminoalkyl, optionally substituted aminoalkenyl, optionally substituted aminoalkynyl, or absent; wherein the combination of $R^3$ with one or more of $R^{1'}$, $R^{1''}$, $R^{2'}$, $R^{2''}$, or $R^5$ (e.g., the combination of $R^{1'}$ and $R^3$, the combination of $R^{1''}$ and $R^3$, the combination of $R^{2'}$ and $R^3$, the combination of $R^{2''}$ and $R^3$, or the combination of $R^5$ and $R^3$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); wherein the combination of $R^5$ with one or more of $R^{1'}$, $R^{1''}$, $R^{2'}$, or $R^{2''}$ (e.g., the combination of $R^{1'}$ and $R^5$, the combination of $R^{1''}$ and $R^5$, the combination of $R^{2'}$ and $R^5$, or the combination of $R^{2''}$ and $R^5$) can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); and wherein the combination of $R^4$ and one or more of $R^{1'}$, $R^{1''}$, $R^{2'}$, $R^{2''}$, $R^3$, or $R^5$ can join together to form optionally substituted alkylene or optionally substituted heteroalkylene and, taken together with the carbons to which they are attached, provide an optionally substituted heterocyclyl (e.g., a bicyclic, tricyclic, or tetracyclic heterocyclyl); each of m' and m" is, independently, an integer from 0 to 3 (e.g., from 0 to 2, from 0 to 1, from 1 to 3, or from 1 to 2);

each of $Y^1$, $Y^2$, and $Y^3$, is, independently, O, S, Se, —$NR^{N1}$—, optionally substituted alkylene, or optionally substituted heteroalkylene, wherein $R^{N1}$ is H, optionally substituted alkyl, optionally substituted alkenyl, optionally substituted alkynyl, optionally substituted aryl, or absent; each $Y^4$ is, independently, H, hydroxy, thiol, boranyl, optionally substituted alkyl, optionally substituted alkenyl, optionally substituted alkynyl, optionally substituted alkoxy, optionally substituted alkenyloxy, optionally substituted alkynyloxy, optionally substituted thioalkoxy, optionally substituted alkoxyalkoxy, or optionally substituted amino;

each $Y^5$ is, independently, O, S, Se, optionally substituted alkylene (e.g., methylene), or optionally substituted heteroalkylene; and B is a nucleobase, either modified or unmodified. In some embodiments, the 2'-hydroxy group (OH) can be modified or replaced with a number of different substituents. Exemplary substitutions at the 2'-position include, but are not limited to, H, azido, halo (e.g., fluoro), optionally substituted $C_1$-6 alkyl (e.g., methyl); optionally substituted $C_1$-6 alkoxy (e.g., methoxy or ethoxy); optionally substituted $C_6$-10 aryloxy; optionally substituted $C_3$-8 cycloalkyl; optionally substituted $C_6$-10 aryl-$C_1$-6 alkoxy, optionally substituted $C_1$-12 (heterocyclyl)oxy; a sugar (e.g., ribose, pentose, or any described herein); a polyethyleneglycol (PEG), —O(CH$_2$CH$_2$O)$_n$CH$_2$CH$_2$OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxy is connected by a $C_1$-6 alkylene or $C_1$-6 heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein.

Generally, RNA includes the sugar group ribose, which is a 5-membered ring having an oxygen. Exemplary, non-limiting alternative nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino (that also has a phosphoramidate backbone)); multicyclic forms (e.g., tricyclo and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone).

In some embodiments, the sugar group contains one or more carbons that possess the opposite stereochemical configuration of the corresponding carbon in ribose. Thus, a polynucleotide molecule can include nucleotides containing, e.g., arabinose or L-ribose, as the sugar.

In some embodiments, the polynucleotide of the disclosure includes at least one nucleoside wherein the sugar is L-ribose, 2'-O-methyl-ribose, 2'-fluoro-ribose, arabinose, hexitol, an LNA, or a PNA.

Alterations on the Internucleoside Linkage

Alternative nucleotides can be altered on the internucleoside linkage (e.g., phosphate backbone). Herein, in the context of the polynucleotide backbone, the phrases "phosphate" and "phosphodiester" are used interchangeably. Backbone phosphate groups can be altered by replacing one or more of the oxygen atoms with a different substituent.

The alternative nucleotides can include the wholesale replacement of an unaltered phosphate moiety with another internucleoside linkage as described herein. Examples of alternative phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be altered by the replacement of a linking oxygen with nitrogen (bridged phosphoramidates), sulfur (bridged phosphorothioates), and carbon (bridged methylene-phosphonates).

The alternative nucleosides and nucleotides can include the replacement of one or more of the non-bridging oxygens with a borane moiety (BH$_3$), sulfur (thio), methyl, ethyl, and/or methoxy. As a non-limiting example, two non-bridging oxygens at the same position (e.g., the alpha (α), beta (β) or gamma (γ) position) can be replaced with a sulfur (thio) and a methoxy.

The replacement of one or more of the oxygen atoms at the α position of the phosphate moiety (e.g., α-thio phosphate) is provided to confer stability (such as against exonucleases and endonucleases) to RNA and DNA through the unnatural phosphorothioate backbone linkages. Phosphorothioate DNA and RNA have increased nuclease resistance and subsequently a longer half-life in a cellular environment.

Other internucleoside linkages that may be employed according to the present disclosure, including internucleoside linkages which do not contain a phosphorous atom, are described herein.

Internal Ribosome Entry Sites

Polynucleotides may contain an internal ribosome entry site (IRES). An IRES may act as the sole ribosome binding site, or may serve as one of multiple ribosome binding sites of an mRNA. A polynucleotide containing more than one functional ribosome binding site may encode several peptides or polypeptides that are translated independently by the ribosomes (e.g., multicistronic mRNA). When polynucleotides are provided with an IRES, further optionally provided is a second translatable region. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

5'-UTRs

A 5'-UTR may be provided as a flanking region to polynucleotides (e.g., mRNAs). A 5'-UTR may be homologous or heterologous to the coding region found in a polynucleotide. Multiple 5'-UTRs may be included in the flanking region and may be the same or of different sequences. Any portion of the flanking regions, including none, may be codon optimized and any may independently contain one or more different structural or chemical alterations, before and/or after codon optimization.

Shown in Table 21 in U.S. Provisional Application No. 61/775,509, and in Table 21 and in Table 22 in U.S. Provisional Application No. 61/829,372, of which are incorporated herein by reference, is a listing of the start and stop site of alternative polynucleotides (e.g., mRNA) of the disclosure. In Table 21 each 5'-UTR (5'-UTR-005 to 5'-UTR 68511) is identified by its start and stop site relative to its native or wild type (homologous) transcript (ENST; the identifier used in the ENSEMBL database).

To alter one or more properties of a polynucleotide (e.g., mRNA), 5'-UTRs which are heterologous to the coding region of an alternative polynucleotide (e.g., mRNA) may be engineered. The polynucleotides (e.g., mRNA) may then be administered to cells, tissue or organisms and outcomes such as protein level, localization, and/or half-life may be measured to evaluate the beneficial effects the heterologous 5'-UTR may have on the alternative polynucleotides (mRNA). Variants of the 5'-UTRs may be utilized wherein one or more nucleotides are added or removed to the termini, including A, T, C or G. 5'-UTRs may also be codon-optimized, or altered in any manner described herein.

5'-UTRs, 3'-UTRs, and Translation Enhancer Elements (TEEs)

The 5'-UTR of a polynucleotides (e.g., mRNA) may include at least one translation enhancer element. The term "translational enhancer element" refers to sequences that increase the amount of polypeptide or protein produced from a polynucleotide. As a non-limiting example, the TEE may be located between the transcription promoter and the start codon. The polynucleotides (e.g., mRNA) with at least one TEE in the 5'-UTR may include a cap at the 5'-UTR. Further, at least one TEE may be located in the 5'-UTR of polynucleotides (e.g., mRNA) undergoing cap-dependent or cap-independent translation.

In one aspect, TEEs are conserved elements in the UTR which can promote translational activity of a polynucleotide such as, but not limited to, cap-dependent or cap-independent translation. The conservation of these sequences has been previously shown by Panek et al. (Nucleic Acids Research, 2013, 1-10) across 14 species including humans.

In one non-limiting example, the TEEs known may be in the 5'-leader of the Gtx homeodomain protein (Chappell et al., Proc. Natl. Acad. Sci. USA 101:9590-9594, 2004, the TEEs of which are incorporated herein by reference).

In another non-limiting example, TEEs are disclosed as SEQ ID NOs: 1-35 in US Patent Publication No. 2009/0226470, SEQ ID NOs: 1-35 in US Patent Publication No. 2013/0177581, SEQ ID NOs: 1-35 in International Patent Publication No. WO2009/075886, SEQ ID NOs: 1-5, and 7-645 in International Patent Publication No. WO2012/009644, SEQ ID NO: 1 in International Patent Publication No. WO1999/024595, SEQ ID NO: 1 in U.S. Pat. No. 6,310,197, and SEQ ID NO: 1 in U.S. Pat. No. 6,849,405, the TEE sequences of each of which are incorporated herein by reference.

In yet another non-limiting example, the TEE may be an internal ribosome entry site (IRES), HCV-IRES or an IRES element such as, but not limited to, those described in U.S. Pat. No. 7,468,275, US Patent Publication Nos. 2007/0048776 and 2011/0124100 and International Patent Publication Nos. WO2007/025008 and WO2001/055369, the IRES sequences of each of which are incorporated herein by reference. The IRES elements may include, but are not limited to, the Gtx sequences (e.g., Gtx9-nt, Gtx8-nt, Gtx7-nt) described by Chappell et al. (Proc. Natl. Acad. Sci. USA 101:9590-9594, 2004) and Zhou et al. (PNAS 102:6273-6278, 2005) and in US Patent Publication Nos. 2007/0048776 and 2011/0124100 and International Patent Publication No. WO2007/025008, the IRES sequences of each of which are incorporated herein by reference.

"Translational enhancer polynucleotides" are polynucleotides which include one or more of the specific TEE exemplified herein and/or disclosed in the art (see e.g., U.S. Pat. Nos. 6,310,197, 6,849,405, 7,456,273, 7,183,395, U.S. Patent Publication Nos. 20090/226470, 2007/0048776, 2011/0124100, 2009/0093049, 2013/0177581, International Patent Publication Nos. WO2009/075886, WO2007/025008, WO2012/009644, WO2001/055371 WO1999/024595, and European Patent Nos. 2610341 and 2610340; the TEE sequences of each of which are incorporated herein by reference) or their variants, homologs or functional derivatives. One or multiple copies of a specific TEE can be present in a polynucleotide (e.g., mRNA). The TEEs in the translational enhancer polynucleotides can be organized in one or more sequence segments. A sequence segment can harbor one or more of the specific TEEs exemplified herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the specific TEEs exemplified herein, identical or different number of copies of each of the specific TEEs, and/or identical or different organization of the TEEs within each sequence segment.

A polynucleotide (e.g., mRNA) may include at least one TEE that is described in International Patent Publication Nos. WO1999/024595, WO2012/009644, WO2009/075886, WO2007/025008, WO1999/024595, European Patent Publication Nos. 2610341 and 2610340, U.S. Pat. Nos. 6,310,197, 6,849,405, 7,456,273, 7,183,395, and US Patent Publication Nos. 2009/0226470, 2011/0124100, 2007/0048776, 2009/0093049, and 2013/0177581 the TEE sequences of each of which are incorporated herein by reference. The TEE may be located in the 5'-UTR of the polynucleotides (e.g., mRNA).

A polynucleotide (e.g., mRNA) may include at least one TEE that has at least 50%, at least 55%, at least 60%, at least 65%, at least 70%, at least 75%, at least 80%, at least 85%, at least 90%, at least 95% or at least 99% identity with the TEEs described in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, U.S. Pat. Nos. 6,310,197, 6,849,405, 7,456,273, 7,183,395, the TEE sequences of each of which are incorporated herein by reference.

The 5'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 5'-UTR of a polynucleotide (e.g., mRNA) may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In some cases, the 5'-UTR may include a spacer to separate two TEE sequences. As a non-limiting example, the spacer may be a 15 nucleotide spacer and/or other spacers known in the art. As another non-limiting example, the 5'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 5'-UTR.

In other instances, the spacer separating two TEE sequences may include other sequences known in the art which may regulate the translation of the polynucleotides (e.g., mRNA) of the present disclosure, such as, but not limited to, miR sequences (e.g., miR binding sites and miR seeds). As a non-limiting example, each spacer used to separate two TEE sequences may include a different miR sequence or component of a miR sequence (e.g., miR seed sequence).

In some instances, the TEE in the 5'-UTR of a polynucleotide (e.g., mRNA) may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395 the TEE sequences of each of which are incorporated herein by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in US Patent Publication Nos. 2009/0226470, 2007/0048776, 2013/0177581 and 2011/0124100, International Patent Publication Nos. WO1999/024595, WO2012/009644, WO2009/075886 and WO2007/025008, European Patent Publication Nos. 2610341 and 2610340, and U.S. Pat. Nos. 6,310,197, 6,849,405, 7,456,273, and 7,183,395; the TEE sequences of each of which are incorporated herein by reference.

In certain cases, the TEE in the 5'-UTR of the polynucleotides (e.g., mRNA) of the present disclosure may include at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more than 99% of the TEE sequences disclosed in Chappell et al. (Proc. Natl. Acad. Sci. USA 101:9590-9594, 2004) and Zhou et al. (PNAS 102: 6273-6278, 2005), in Supplemental Table 1 and in Supplemental Table 2 disclosed by Wellensiek et al (Genome-wide profiling of human cap-independent translation-enhancing elements, Nature Methods, 2013; DOI: 10.1038/NMETH.2522); the TEE sequences of each of which are herein incorporated by reference. In another embodiment, the TEE in the 5'-UTR of the polynucleotides (e.g., mRNA) of the present disclosure may include a 5-30 nucleotide fragment, a 5-25 nucleotide fragment, a 5-20 nucleotide fragment, a 5-15 nucleotide fragment, a 5-10 nucleotide fragment of the TEE sequences disclosed in Chappell et al. (Proc. Natl. Acad. Sci. USA 101:9590-9594, 2004) and Zhou et al. (PNAS 102:6273-6278, 2005), in Supplemental Table 1 and in Supplemental Table 2 disclosed by Wellensiek et al (Genome-wide profiling of human cap-independent translation-enhancing elements, Nature Methods, 2013; DOI: 10.1038/NMETH.2522); the TEE sequences of each of which is incorporated herein by reference.

In some cases, the TEE used in the 5'-UTR of a polynucleotide (e.g., mRNA) is an IRES sequence such as, but not limited to, those described in U.S. Pat. No. 7,468,275 and International Patent Publication No. WO2001/055369, the TEE sequences of each of which are incorporated herein by reference.

In some instances, the TEEs used in the 5'-UTR of a polynucleotide (e.g., mRNA) may be identified by the methods described in US Patent Publication Nos. 2007/0048776 and 2011/0124100 and International Patent Publication Nos. WO2007/025008 and WO2012/009644, the methods of each of which are incorporated herein by reference.

In some cases, the TEEs used in the 5'-UTR of a polynucleotide (e.g., mRNA) of the present disclosure may be a transcription regulatory element described in U.S. Pat. Nos. 7,456,273 and 7,183,395, US Patent Publication No. 2009/0093049, and International Publication No. WO2001/055371, the TEE sequences of each of which are incorporated herein by reference. The transcription regulatory elements may be identified by methods known in the art, such as, but not limited to, the methods described in U.S. Pat. Nos. 7,456,273 and 7,183,395, US Patent Publication No. 2009/0093049, and International Publication No. WO2001/055371, the methods of each of which are incorporated herein by reference.

In yet other instances, the TEE used in the 5'-UTR of a polynucleotide (e.g., mRNA) is a polynucleotide or portion thereof as described in U.S. Pat. Nos. 7,456,273 and 7,183,395, US Patent Publication No. 2009/0093049, and International Publication No. WO2001/055371, the TEE sequences of each of which are incorporated herein by reference.

The 5'-UTR including at least one TEE described herein may be incorporated in a monocistronic sequence such as, but not limited to, a vector system or a polynucleotide vector. As a non-limiting example, the vector systems and polynucleotide vectors may include those described in U.S. Pat. Nos. 7,456,273 and 7,183,395, US Patent Publication Nos. 2007/0048776, 2009/0093049 and 2011/0124100, and International Patent Publication Nos. WO2007/025008 and WO2001/055371, the TEE sequences of each of which are incorporated herein by reference.

The TEEs described herein may be located in the 5'-UTR and/or the 3'-UTR of the polynucleotides (e.g., mRNA). The TEEs located in the 3'-UTR may be the same and/or different than the TEEs located in and/or described for incorporation in the 5'-UTR.

In some cases, the 3'-UTR of a polynucleotide (e.g., mRNA) may include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. The TEE sequences in the 3'-UTR of the polynucleotides (e.g., mRNA) of the present disclosure may be the same or different TEE sequences. The TEE sequences may be in a pattern such as ABABAB, AABBAABBAABB, or ABCABCABC, or variants thereof, repeated once, twice, or more than three times. In these patterns, each letter, A, B, or C represent a different TEE sequence at the nucleotide level.

In one instance, the 3'-UTR may include a spacer to separate two TEE sequences. As a non-limiting example, the spacer may be a 15 nucleotide spacer and/or other spacers known in the art. As another non-limiting example, the 3'-UTR may include a TEE sequence-spacer module repeated at least once, at least twice, at least 3 times, at least 4 times, at least 5 times, at least 6 times, at least 7 times, at least 8 times, at least 9 times, or more than 9 times in the 3'-UTR.

In other cases, the spacer separating two TEE sequences may include other sequences known in the art which may regulate the translation of the polynucleotides (e.g., mRNA) of the present disclosure such as, but not limited to, miR sequences described herein (e.g., miR binding sites and miR seeds). As a non-limiting example, each spacer used to separate two TEE sequences may include a different miR sequence or component of a miR sequence (e.g., miR seed sequence).

In yet other cases, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010).

Stem Loops

Polynucleotides (e.g., mRNAs) may include a stem loop such as, but not limited to, a histone stem loop. The stem loop may be a nucleotide sequence that is about 25 or about 26 nucleotides in length such as, but not limited to, SEQ ID NOs: 7-17 as described in International Patent Publication No. WO2013/103659, of which SEQ ID NOs: 7-17 are incorporated herein by reference. The histone stem loop may be located 3'-relative to the coding region (e.g., at the 3'-terminus of the coding region). As a non-limiting example, the stem loop may be located at the 3'-end of a polynucleotide described herein. In some cases, a polynucleotide (e.g., an mRNA) includes more than one stem loop (e.g., two stem loops). Examples of stem loop sequences are described in International Patent Publication Nos. WO2012/019780 and WO201502667, the stem loop sequences of which are herein incorporated by reference. In some instances, a polynucleotide includes the stem loop sequence CAAAGGCTCTTTTCAGAGCCACCA (SEQ ID NO: 1). In others, a polynucleotide includes the stem loop sequence CAAAGGCUCUUUUCAGAGCCACCA (SEQ ID NO: 2).

A stem loop may be located in a second terminal region of a polynucleotide. As a non-limiting example, the stem loop may be located within an untranslated region (e.g., 3'-UTR) in a second terminal region.

In some cases, a polynucleotide such as, but not limited to mRNA, which includes the histone stem loop may be stabilized by the addition of a 3'-stabilizing region (e.g., a 3'-stabilizing region including at least one chain terminating nucleoside). Not wishing to be bound by theory, the addition of at least one chain terminating nucleoside may slow the degradation of a polynucleotide and thus can increase the half-life of the polynucleotide.

In other cases, a polynucleotide such as, but not limited to mRNA, which includes the histone stem loop may be stabilized by an alteration to the 3'-region of the polynucleotide that can prevent and/or inhibit the addition of oligo(U) (see e.g., International Patent Publication No. WO2013/103659).

In yet other cases, a polynucleotide such as, but not limited to mRNA, which includes the histone stem loop may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

In some instances, the polynucleotides of the present disclosure may include a histone stem loop, a poly-A region, and/or a 5'-cap structure. The histone stem loop may be before and/or after the poly-A region. The polynucleotides including the histone stem loop and a poly-A region sequence may include a chain terminating nucleoside described herein.

In other instances, the polynucleotides of the present disclosure may include a histone stem loop and a 5'-cap structure. The 5'-cap structure may include, but is not limited to, those described herein and/or known in the art.

In some cases, the conserved stem loop region may include a miR sequence described herein. As a non-limiting example, the stem loop region may include the seed sequence of a miR sequence described herein. In another non-limiting example, the stem loop region may include a miR-122 seed sequence.

In certain instances, the conserved stem loop region may include a miR sequence described herein and may also include a TEE sequence.

In some cases, the incorporation of a miR sequence and/or a TEE sequence changes the shape of the stem loop region which may increase and/or decrease translation. (see e.g, Kedde et al. A Pumilio-induced RNA structure switch in p27-3'UTR controls miR-221 and miR-22 accessibility. Nature Cell Biology. 2010, herein incorporated by reference in its entirety).

Polynucleotides may include at least one histone stem-loop and a poly-A region or polyadenylation signal. Nonlimiting examples of polynucleotide sequences encoding for at least one histone stem-loop and a poly-A region or a polyadenylation signal are described in International Patent Publication No. WO2013/120497, WO2013/120629, WO2013/120500, WO2013/120627, WO2013/120498, WO2013/120626, WO2013/120499 and WO2013/120628, the sequences of each of which are incorporated herein by reference. In certain cases, the polynucleotide encoding for a histone stem loop and a poly-A region or a polyadenylation signal may code for a pathogen antigen or fragment thereof such as the polynucleotide sequences described in International Patent Publication No WO2013/120499 and WO2013/120628, the sequences of both of which are incorporated herein by reference. In other cases, the polynucleotide encoding for a histone stem loop and a poly-A region or a polyadenylation signal may code for a therapeutic protein such as the polynucleotide sequences described in International Patent Publication No WO2013/120497 and WO2013/120629, the sequences of both of which are incorporated herein by reference. In some cases, the polynucleotide encoding for a histone stem loop and a poly-A region or a polyadenylation signal may code for a tumor antigen or fragment thereof such as the polynucleotide sequences described in International Patent Publication No WO2013/120500 and WO2013/120627, the sequences of both of which are incorporated herein by reference. In other cases, the polynucleotide encoding for a histone stem loop and a poly-A region or a polyadenylation signal may code for a allergenic antigen or an autoimmune self-antigen such as the polynucleotide sequences described in International Patent Publication No WO2013/120498 and WO2013/120626, the sequences of both of which are incorporated herein by reference.

Poly-A Regions

A polynucleotide or nucleic acid (e.g., an mRNA) may include a polyA sequence and/or polyadenylation signal. A polyA sequence may be comprised entirely or mostly of adenine nucleotides or analogs or derivatives thereof. A polyA sequence may be a tail located adjacent to a 3' untranslated region of a nucleic acid.

During RNA processing, a long chain of adenosine nucleotides (poly-A region) is normally added to messenger RNA (mRNA) molecules to increase the stability of the molecule. Immediately after transcription, the 3'-end of the transcript is cleaved to free a 3'-hydroxy. Then poly-A polymerase adds a chain of adenosine nucleotides to the RNA. The process, called polyadenylation, adds a poly-A region that is between 100 and 250 residues long.

Unique poly-A region lengths may provide certain advantages to the alternative polynucleotides of the present disclosure.

Generally, the length of a poly-A region of the present disclosure is at least 30 nucleotides in length. In another embodiment, the poly-A region is at least 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 70 nucleotides. In another embodiment, the length is at least 80 nucleotides. In another embodiment, the length is at least 90 nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1700 nucleotides. In another embodiment, the length is at least 1800 nucleotides. In another embodiment, the length is at least 1900 nucleotides. In another embodiment, the length is at least 2000 nucleotides. In another embodiment, the length is at least 2500 nucleotides. In another embodiment, the length is at least 3000 nucleotides.

In some instances, the poly-A region may be 80 nucleotides, 120 nucleotides, 160 nucleotides in length on an alternative polynucleotide molecule described herein.

In other instances, the poly-A region may be 20, 40, 80, 100, 120, 140 or 160 nucleotides in length on an alternative polynucleotide molecule described herein.

In some cases, the poly-A region is designed relative to the length of the overall alternative polynucleotide. This design may be based on the length of the coding region of the alternative polynucleotide, the length of a particular feature or region of the alternative polynucleotide (such as mRNA), or based on the length of the ultimate product expressed from the alternative polynucleotide. When relative to any feature of the alternative polynucleotide (e.g., other than the mRNA portion which includes the poly-A region) the poly-A region may be 10, 20, 30, 40, 50, 60, 70, 80, 90 or 100% greater in length than the additional feature. The poly-A region may also be designed as a fraction of the alternative polynucleotide to which it belongs. In this context, the poly-A region may be 10, 20, 30, 40, 50, 60, 70, 80, or 90% or more of the total length of the construct or the total length of the construct minus the poly-A region.

In certain cases, engineered binding sites and/or the conjugation of polynucleotides (e.g., mRNA) for poly-A binding protein may be used to enhance expression. The engineered binding sites may be sensor sequences which can operate as binding sites for ligands of the local microenvironment of the polynucleotides (e.g., mRNA). As a non-limiting example, the polynucleotides (e.g., mRNA) may include at least one engineered binding site to alter the binding affinity of poly-A binding protein (PABP) and analogs thereof. The incorporation of at least one engineered binding site may increase the binding affinity of the PABP and analogs thereof.

Additionally, multiple distinct polynucleotides (e.g., mRNA) may be linked together to the PABP (poly-A binding protein) through the 3'-end using alternative nucleotides at the 3'-terminus of the poly-A region. Transfection experiments can be conducted in relevant cell lines at and protein production can be assayed by ELISA at 12 hours, 24 hours, 48 hours, 72 hours, and day 7 post-transfection. As a non-limiting example, the transfection experiments may be used to evaluate the effect on PABP or analogs thereof binding affinity as a result of the addition of at least one engineered binding site.

In certain cases, a poly-A region may be used to modulate translation initiation. While not wishing to be bound by theory, the poly-A region recruits PABP which in turn can interact with translation initiation complex and thus may be essential for protein synthesis.

In some cases, a poly-A region may also be used in the present disclosure to protect against 3'-5'-exonuclease digestion.

In some instances, a polynucleotide (e.g., mRNA) may include a polyA-G Quartet. The G-quartet is a cyclic hydrogen bonded array of four guanosine nucleotides that can be formed by G-rich sequences in both DNA and RNA. In this embodiment, the G-quartet is incorporated at the end of the poly-A region. The resultant polynucleotides (e.g., mRNA) may be assayed for stability, protein production and other parameters including half-life at various time points. It has been discovered that the polyA-G quartet results in protein production equivalent to at least 75% of that seen using a poly-A region of 120 nucleotides alone.

In some cases, a polynucleotide (e.g., mRNA) may include a poly-A region and may be stabilized by the addition of a 3'-stabilizing region. The polynucleotides (e.g., mRNA) with a poly-A region may further include a 5'-cap structure.

In other cases, a polynucleotide (e.g., mRNA) may include a poly-A-G Quartet. The polynucleotides (e.g., mRNA) with a poly-A-G Quartet may further include a 5'-cap structure.

In some cases, the 3'-stabilizing region which may be used to stabilize a polynucleotide (e.g., mRNA) including a poly-A region or poly-A-G Quartet may be, but is not limited to, those described in International Patent Publication No. WO2013/103659, the poly-A regions and poly-A-G Quartets of which are incorporated herein by reference. In other cases, the 3'-stabilizing region which may be used with the present disclosure include a chain termination nucleoside such as 3'-deoxyadenosine (cordycepin), 3'-deoxyuridine, 3'-deoxycytosine, 3'-deoxyguanosine, 3'-deoxythymine, 2',3'-dideoxynucleosides, such as 2',3'-dideoxyadenosine, 2',3'-dideoxyuridine, 2',3'-dideoxycytosine, 2',3'-dideoxyguanosine, 2',3'-dideoxythymine, a 2'-deoxynucleoside, or an O-methylnucleoside.

In other cases, a polynucleotide such as, but not limited to mRNA, which includes a polyA region or a poly-A-G Quartet may be stabilized by an alteration to the 3'-region of the polynucleotide that can prevent and/or inhibit the addition of oligo(U) (see e.g., International Patent Publication No. WO2013/103659).

In yet other instances, a polynucleotide such as, but not limited to mRNA, which includes a poly-A region or a poly-A-G Quartet may be stabilized by the addition of an oligonucleotide that terminates in a 3'-deoxynucleoside, 2',3'-dideoxynucleoside 3'-O-methylnucleosides, 3'-O-ethylnucleosides, 3'-arabinosides, and other alternative nucleosides known in the art and/or described herein.

Chain Terminating Nucleosides

A nucleic acid may include a chain terminating nucleoside. For example, a chain terminating nucleoside may include those nucleosides deoxygenated at the 2' and/or 3' positions of their sugar group. Such species may include 3'-deoxyadenosine (cordycepin), 3'-deoxyuridine, 3'-deoxycytosine, 3'-deoxyguanosine, 3'-deoxythymine, and 2',3'-dideoxynucleosides, such as 2',3'-dideoxyadenosine, 2',3'-dideoxyuridine, 2',3'-dideoxycytosine, 2',3'-dideoxyguanosine, and 2',3'-dideoxythymine.

The RNAs and multimeric nucleic acid complexes described herein can be used as therapeutic agents or are therapeutic mRNAs. As used herein, the term "therapeutic mRNA" refers to an mRNA that encodes a therapeutic protein. Therapeutic proteins mediate a variety of effects in a host cell or a subject in order to treat a disease or ameliorate the signs and symptoms of a disease. For example, an RNA or a multimeric structure described herein can be administered to an animal or human subject, wherein the RNA is translated in vivo to produce a therapeutic peptide in the subject in need thereof. Accordingly, provided herein are compositions, methods, kits, and reagents for treatment or prevention of disease or conditions in humans and other mammals. The active therapeutic agents of the present disclosure include RNAs (e.g., mRNAs) disclosed herein, cells containing the mRNAs or polypeptides translated from the mRNAs, polypeptides translated from mRNAs, cells contacted with cells containing mRNAs or polypeptides translated therefrom, tissues containing cells containing the mRNAs described herein and organs containing tissues containing cells containing the mRNAs described herein.

In another aspect, the disclosure provides methods and compositions useful for protecting RNAs disclosed herein (e.g., RNA transcripts) from degradation (e.g., exonuclease mediated degradation), such as methods and compositions described in US20150050738A1 and WO2015023975A1, the contents of each of which are herein incorporated by reference in their entireties.

In some embodiments, the protected RNAs are present outside of cells. In some embodiments, the protected RNAs are present in cells. In some embodiments, methods and compositions are provided that are useful for post-transcriptionally altering protein and/or RNA levels in a targeted manner. In some embodiments, methods disclosed herein involve reducing or preventing degradation or processing of targeted RNAs thereby elevating steady state levels of the targeted RNAs. In some embodiments, methods disclosed herein may also or alternatively involve increasing translation or increasing transcription of targeted RNAs, thereby elevating levels of RNA and/or protein levels in a targeted manner.

It is recognized that certain RNA degradation is mediated by exonucleases. In some embodiments, exonucleases may destroy RNA from its 3' end and/or 5' end. Without wishing to be bound by theory, in some embodiments, it is believed that one or both ends of RNA can be protected from exonuclease enzyme activity by contacting the RNA with oligonucleotides (oligos) that hybridize with the RNA at or near one or both ends, thereby increasing stability and/or levels of the RNA. The ability to increase stability and/or levels of a RNA by targeting the RNA at or near one or both ends, as disclosed herein, is surprising in part because of the presence of endonucleases (e.g., in cells) capable of destroying the RNA through internal cleavage. Moreover, in some embodiments, it is surprising that a 5' targeting oligonucleotide is effective alone (e.g., not in combination with a 3' targeting oligonucleotide or in the context of a pseudocircularization oligonucleotide) at stabilizing RNAs or increasing RNA levels because in cells, for example, 3' end processing exonucleases may be dominant (e.g., compared with 5' end processing exonucleases). However, in some embodiments, 3' targeting oligonucleotides are used in combination with 5' targeting oligonucleotides, or alone, to stabilize a target RNA.

In some embodiments, methods provided herein involve use of oligonucleotides that stabilize an RNA by hybridizing at a 5' and/or 3' region of the RNA. In some embodiments, oligonucleotides that prevent or inhibit degradation of an RNA by hybridizing with the RNA may be referred to herein as "stabilizing oligonucleotides." In some examples, such oligonucleotides hybridize with an RNA and prevent or inhibit exonuclease mediated degradation. Inhibition of exonuclease mediated degradation includes, but is not limited to, reducing the extent of degradation of a particular RNA by exonucleases. For example, an exonuclease that processes only single stranded RNA may cleave a portion of the RNA up to a region where an oligonucleotide is hybridized with the RNA because the exonuclease cannot effectively process (e.g., pass through) the duplex region. Thus, in some embodiments, using an oligonucleotide that targets a particular region of an RNA makes it possible to control the extent of degradation of the RNA by exonucleases up to that region.

For example, use of an oligonucleotide (oligo) that hybridizes at an end of an RNA may reduce or eliminate degradation by an exonuclease that processes only single stranded RNAs from that end. For example, use of an oligonucleotide that hybridizes at the 5' end of an RNA may reduce or eliminate degradation by an exonuclease that processes single stranded RNAs in a 5' to 3' direction. Similarly, use of an oligonucleotide that hybridizes at the 3' end of an RNA may reduce or eliminate degradation by an exonuclease that processes single stranded RNAs in a 3' to 5' direction. In some embodiments, lower concentrations of an oligo may be used when the oligo hybridizes at both the 5' and 3' regions of the RNA. In some embodiments, an oligo that hybridizes at both the 5' and 3' regions of the RNA protects the 5' and 3' regions of the RNA from degradation (e.g., by an exonuclease). In some embodiments, an oligo that hybridizes at both the 5' and 3' regions of the RNA creates a pseudo-circular RNA (e.g., a circularized RNA with a region of the polyA tail that protrudes from the circle). In some embodiments, a pseudo-circular RNA is translated at a higher efficiency than a non-pseudo-circular RNA.

In some aspects, methods are provided for stabilizing a synthetic RNA disclosed herein (e.g., a synthetic RNA that is to be delivered to a cell). In some embodiments, the methods involve contacting a synthetic RNA with one or more oligonucleotides that bind to a 5' region of the synthetic RNA and a 3' region of the synthetic RNA and that when bound to the synthetic RNA form a circularized product with the synthetic RNA. In some embodiments, the synthetic RNA is contacted with the one or more oligonucleotides outside of a cell. In some embodiments, the methods further involve delivering the circularized product to a cell.

In some aspects of the invention, methods are provided for increasing expression of a protein in a cell that involve delivering to a cell a circularized synthetic RNA that encodes the protein, in which synthesis of the protein in the cell is increased following delivery of the circularized RNA to the cell. In some embodiments, the circularized synthetic RNA comprises one or more modified nucleotides. In some embodiments, methods are provided that involve delivering to a cell a circularized synthetic RNA that encodes a protein, in which synthesis of the protein in the cell is increased following delivery of the circularized synthetic RNA to the cell. In some embodiments, a circularized synthetic RNA is a single-stranded covalently closed circular RNA. In some embodiments, a single-stranded covalently closed circular RNA comprises one or more modified nucleotides. In some embodiments, the circularized synthetic RNA is formed by synthesizing an RNA that has a 5' end and a 3' and ligating together the 5' and 3' ends. In some embodiments, the circularized synthetic RNA is formed by producing a synthetic RNA (e.g., through in vitro transcription or artificial (non-natural) chemical synthesis) and contacting the synthetic RNA with one or more oligonucleotides that bind to a 5' region of the synthetic RNA and a 3' region of the synthetic RNA, and that when bound to the synthetic RNA form a circularized product with the synthetic RNA.

In some aspects of the invention, an oligonucleotide is provided that comprises a region of complementarity that is complementary with at least 5 contiguous nucleotides of an RNA transcript, in which the nucleotide at the 3'-end of the region of complementary is complementary with a nucleotide within 10 nucleotides of the transcription start site of the RNA transcript. In some embodiments, the oligonucleotide comprises nucleotides linked by at least one modified internucleoside linkage or at least one bridged nucleotide. In some embodiments, the oligonucleotide is 8 to 80, 8 to 50, 9 to 50, 10 to 50, 8 to 30, 9 to 30, 10 to 30, 15 to 30, 9 to 20, 8 to 20, 8 to 15, or 9 to 15 nucleotides in length. In some embodiments, the oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80 or more nucleotides in length.

In some aspects of the invention, an oligonucleotide is provided that comprises two regions of complementarity each of which is complementary with at least 5 contiguous nucleotides of an RNA transcript, in which the nucleotide at the 3'-end of the first region of complementary is complementary with a nucleotide within 100 nucleotides of the transcription start site of the RNA transcript and in which the second region of complementarity is complementary with a region of the RNA transcript that ends within 300 nucleotides of the 3'-end of the RNA transcript.

Several exemplary oligonucleotide design schemes are contemplated herein for increasing stability of the RNA (e.g., mRNA) molecules disclosed herein. With regard to oligonucleotides targeting the 3' end of an RNA, at least two exemplary design schemes are contemplated. As a first scheme, an oligonucleotide is designed to be complementary to the 3' end of an RNA, before the polyA tail. As a second scheme, an oligonucleotide is designed to be complementary to the 3' end of RNA and the oligonucleotide has a 5' poly-T region that hybridizes to the polyA tail of the RNA.

With regard to oligonucleotides targeting the 5' end of an RNA, at least three exemplary design schemes are contemplated. For scheme one, an oligonucleotide is designed to be complementary to the 5' end of RNA. For scheme two, an oligonucleotide is designed to be complementary to the 5' end of RNA and has a 3'overhang to create a RNA-oligo duplex with a recessed end. In this scheme, the overhang is one or more C nucleotides, e.g., two Cs, which can potentially interact with a 5' methylguanosine cap and stabilize the cap further. The overhang could also potentially be another type of nucleotide, and is not limited to C. For scheme three, an oligonucleotide is designed to include a loop region to stabilize a 5' RNA cap. The example shows oligos with loops to stabilize a 5' RNA cap or oligos. In yet another embodiment, an oligonucleotide is designed to bind to both 5' and 3' ends of an RNA to create a pseudo-circularized RNA. For example, an LNA mixmer oligo binding to the 5' and 3' regions of an RNA can achieve an oligo-mediated RNA pseudo circularization.

An oligonucleotide designed as described above may be tested for its ability to upregulate RNA by increasing mRNA stability using the methods outlined in US20150050738A1 and WO2015023975A1, the contents of each of which are herein incorporated by reference in their entireties.

Provided are methods of inducing translation of a synthetic polynucleotide (e.g., a modified mRNA as disclosed herein) to produce a polypeptide in a cell population using the mRNAs described herein. Such translation can be in vivo, ex vivo, in culture, or in vitro. The cell population is contacted with an effective amount of a composition containing a polynucleotide that incorporates the cap analog of the disclosure, and a translatable region encoding the polypeptide. The population is contacted under conditions such that the polynucleotide is localized into one or more cells of the cell population and the polypeptide is translated in the cell from the polynucleotide.

An effective amount of the composition of a polynucleotide disclosed herein is provided based, at least in part, on the target tissue, target cell type, means of administration, physical characteristics of the polynucleotide (e.g., size, and extent of modified nucleosides), and other determinants. In general, an effective amount of the composition provides efficient protein production in the cell, preferably more efficient than a composition containing a corresponding natural polynucleotide. Increased efficiency may be demonstrated by increased cell transfection (i.e., the percentage of cells transfected with the polynucleotide), increased protein translation from the polynucleotide, decreased polynucleotide degradation (as demonstrated, e.g., by increased duration of protein translation from an RNA molecule), or reduced innate immune response of the host cell or improve therapeutic utility.

Aspects of the present disclosure are directed to methods of inducing in vivo translation of a polypeptide in a mammalian subject in need thereof. Therein, an effective amount of a composition containing a polynucleotide of the disclosure that has the cap analog of the disclosure and a translatable region encoding the polypeptide is administered to the subject using the delivery methods described herein. The polynucleotide may also contain at least one modified nucleoside. The polynucleotide is provided in an amount and under other conditions such that the polynucleotide is localized into a cell or cells of the subject and the polypeptide of interest is translated in the cell from the polynucleotide. The cell in which the polynucleotide is localized, or the tissue in which the cell is present, may be targeted with one or more than one rounds of polynucleotide administration.

Other aspects of the present disclosure relate to transplantation of cells containing RNA molecules of the disclosure to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier. Compositions containing RNA molecules of the disclosure are formulated for administration intramuscularly, transarterially, intraperitoneally, intravenously, intranasally, subcutaneously, endoscopically, transdermally, or intrathecally. In some embodiments, the composition is formulated for extended release.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered RNA molecule of the disclosure directs production of one or more polypeptides that provide a functional activity which is substantially absent in the cell in which the polypeptide is translated. For example, the missing functional activity may be enzymatic, structural, or gene regulatory in nature.

In other embodiments, the administered RNA molecule of the disclosure directs production of one or more polypeptides that replace a polypeptide (or multiple polypeptides) that is substantially absent in the cell in which the one or more polypeptides are translated. Such absence may be due to genetic mutation of the encoding gene or regulatory pathway thereof. In other embodiments, the administered RNA molecule of the disclosure directs production of one or more polypeptides to supplement the amount of polypeptide (or multiple polypeptides) that is present in the cell in which the one or more polypeptides are translated. Alternatively, the translated polypeptide functions to antagonize the activity of an endogenous protein present in, on the surface of, or secreted from the cell. Usually, the activity of the endogenous protein is deleterious to the subject, for example, due to mutation of the endogenous protein resulting in altered activity or localization. Additionally, the translated polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a polynucleotide, a carbohydrate, or a small molecule toxin.

The translated proteins described herein are engineered for localization within the cell, potentially within a specific compartment such as the nucleus, or are engineered for secretion from the cell or translocation to the plasma membrane of the cell.

As described herein, a useful feature of the RNA molecules of the disclosure of the present disclosure is the capacity to reduce, evade, avoid or eliminate the innate immune response of a cell to an exogenous RNA. Provided are methods for performing the titration, reduction or elimination of the immune response in a cell or a population of cells. In some embodiments, the cell is contacted with a first composition that contains a first dose of a first exogenous RNA including a translatable region, the cap analog of the disclosure, and optionally at least one modified nucleoside, and the level of the innate immune response of the cell to the first exogenous polynucleotide is determined. Subsequently, the cell is contacted with a second composition, which includes a second dose of the first exogenous polynucleotide, the second dose containing a lesser amount of the first exogenous polynucleotide as compared to the first dose. Alternatively, the cell is contacted with a first dose of a second exogenous polynucleotide. The second exogenous polynucleotide may contain the cap analog of the disclosure, which may be the same or different from the first exogenous polynucleotide or, alternatively, the second exogenous polynucleotide may not contain the cap analog of the disclosure. The steps of contacting the cell with the first composition and/or the second composition may be repeated one or more times. Additionally, efficiency of protein production (e.g., protein translation) in the cell is optionally determined, and the cell may be re-transfected with the first and/or second composition repeatedly until a target protein production efficiency is achieved.

Also provided herein are methods for treating or preventing a symptom of diseases characterized by missing or aberrant protein activity, by replacing the missing protein activity or overcoming the aberrant protein activity. Because of the rapid initiation of protein production following introduction of unnatural mRNAs, as compared to viral DNA vectors, the compounds and RNAs of the present disclosure are particularly advantageous in treating acute diseases such as sepsis, stroke, and myocardial infarction. Moreover, the lack of transcriptional regulation of the unnatural mRNAs of the present disclosure is advantageous in that accurate titration of protein production is achievable. Multiple diseases are characterized by missing (or substantially diminished such that proper protein function does not occur) protein activity. Such proteins may not be present, are present in very low quantities or are essentially non-functional. The present disclosure provides a method for treating such conditions or diseases in a subject by introducing polynucleotide or cell-based therapeutics containing the RNA molecules of the disclosure provided herein, wherein the RNA molecules of the disclosure encode for a protein that replaces the protein activity missing from the target cells of the subject.

Diseases characterized by dysfunctional or aberrant protein activity include, but are not limited to, cancer and proliferative diseases, genetic diseases (e.g., cystic fibrosis), autoimmune diseases, diabetes, neurodegenerative diseases, cardiovascular diseases, and metabolic diseases.

The present disclosure provides a method for treating such conditions or diseases in a subject by introducing the RNA molecules of the disclosure or cell-based therapeutics containing the RNA molecules provided herein, wherein the RNA molecules of the disclosure encode for a protein that antagonizes or otherwise overcomes the aberrant protein activity present in the cell of the subject.

Specific examples of a dysfunctional protein are the missense or nonsense mutation variants of the cystic fibrosis transmembrane conductance regulator (CFTR) gene, which produce a dysfunctional or nonfunctional, respectively, protein variant of CFTR protein, which causes cystic fibrosis.

Thus, provided are methods of treating cystic fibrosis in a mammalian subject by contacting a cell of the subject with an RNA molecule of the disclosure having a translatable region that encodes a functional CFTR polypeptide, under conditions such that an effective amount of the CTFR polypeptide is present in the cell. Preferred target cells are epithelial cells, such as the lung, and methods of administration are determined in view of the target tissue; i.e., for lung delivery, the RNA molecules are formulated for administration by inhalation.

In another embodiment, the present disclosure provides a method for treating hyperlipidemia in a subject, by introducing into a cell population of the subject with an unnatural mRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. Nature 2010; 466: 714-721).

Methods of the present disclosure may enhance polynucleotide delivery into a cell population, in vivo, ex vivo, or in culture. For example, a cell culture containing a plurality of host cells (e.g., eukaryotic cells such as yeast or mammalian cells) is contacted with a composition that contains an RNA molecule disclosed herein. The composition also generally contains a transfection reagent or other compound that increases the efficiency of RNA uptake into the host cells. The RNAs of the disclosure may exhibit enhanced retention in the cell population, relative to a corresponding natural polynucleotide. For example, the retention of the RNA of the disclosure is greater than the retention of the corresponding polynucleotide. In some embodiments, it is at least about 50%, 75%, 90%, 95%, 100%, 150%, 200% or more than 200% greater than the retention of the natural polynucleotide. Such retention advantage may be achieved by one round of transfection with the RNA of the disclosure, or may be obtained following repeated rounds of transfection.

In some embodiments, the RNA of the disclosure is delivered to a target cell population with one or more additional polynucleotides. Such delivery may be at the same time, or the RNA of the disclosure is delivered prior to delivery of the one or more additional polynucleotides. The additional one or more polynucleotides may be RNA molecules of the disclosure or natural polynucleotides. It is understood that the initial presence of the RNA of the disclosure does not substantially induce an innate immune response of the cell population and, moreover, that the innate immune response will not be activated by the later presence of the natural polynucleotides. In this regard, the RNA of the disclosure may not itself contain a translatable region, if the protein desired to be present in the target cell population is translated from the natural polynucleotides.

The present disclosure also provides proteins generated from unnatural mRNAs.

The present disclosure provides pharmaceutical compositions of the RNA molecules or multimeric structures disclosed herein, optionally in combination with one or more pharmaceutically acceptable excipients. The present disclosure also provides pharmaceutical compositions of proteins generated from the RNA molecules or multimeric structures disclosed herein, optionally in combination with one or more pharmaceutically acceptable excipients. Pharmaceutical compositions may optionally comprise one or more additional active substances, e.g., therapeutically and/or prophylactically active substances. Pharmaceutical compositions of the present disclosure may be sterile and/or pyrogen-free. General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

Pharmaceutical compositions may optionally comprise one or more additional therapeutically active substances. In accordance with some embodiments, a method of administering pharmaceutical compositions comprising an RNA of the disclosure, encoding one or more proteins to be delivered to a subject in need thereof is provided. In some embodiments, compositions are administered to humans. For the purposes of the present disclosure, the phrase "active ingredient" generally refers to a polynucleotide (e.g., an mRNA encoding polynucleotide to be delivered), a multimeric structure, a protein, protein encoding or protein-containing complex as described herein and salts thereof.

Although the descriptions of pharmaceutical compositions provided herein are principally directed to pharmaceutical compositions which are suitable for administration to humans, it will be understood by the skilled artisan that such compositions are generally suitable for administration to animals of all sorts.

Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure will vary, depending upon the identity, size, and/or condition of the subject treated and further depending upon the route by which the composition is to be administered. By way of example, the composition may comprise between 0.1% and 100% (w/w), e.g., between 0.1% and 99%, between 0.5 and 50%, between 1-30%, between 5-80%, or at least 80% (w/w), active ingredient.

The polynucleotides and multimeric structures of the disclosure can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein in vivo. In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, lipidoids, liposomes, lipid nanoparticles, polymers, lipoplexes, core-shell nanoparticles, peptides, proteins, cells transfected with multimeric structures, hyaluronidase, nanoparticle mimics and combinations thereof.

In some embodiments, the nucleic acids (e.g., mRNAs, or IVT mRNAs) and multimeric nucleic acid molecules of the disclosure (e.g., multimeric mRNA molecules) can be formulated using one or more liposomes, lipoplexes, or lipid nanoparticles. In one embodiment, pharmaceutical compositions of the nucleic acids or multimeric nucleic acid molecules include lipid nanoparticles (LNPs). In some embodiments, lipid nanoparticles are MC3-based lipid nanoparticles.

The number of polynucleotides encapsulated by a lipid nanoparticle ranges from about 1 polynucleotide to about 100 polynucleotides. In some embodiments, he number of polynucleotides encapsulated by a lipid nanoparticle ranges from about 50 to about 500 polynucleotides. In some embodiments, the number of polynucleotides encapsulated by a lipid nanoparticle ranges from about 250 to about 1000 polynucleotides. In some embodiments, the number of polynucleotides encapsulated by a lipid nanoparticle is greater than 1000.

The number of multimeric molecules encapsulated by a lipid nanoparticle ranges from about 1 multimeric molecule to about 100 multimeric molecules. In some embodiments, he number of multimeric molecules encapsulated by a lipid nanoparticle ranges from about 50 multimeric molecules to about 500 multimeric molecules. In some embodiments, the number of multimeric molecules encapsulated by a lipid nanoparticle ranges from about 250 multimeric molecules to about 1000 multimeric molecules. In some embodiments, the number of multimeric molecules encapsulated by a lipid nanoparticle is greater than 1000 multimeric molecules.

In one embodiment, the polynucleotides or multimeric structures may be formulated in a lipid-polycation complex. The formation of the lipid-polycation complex may be accomplished by methods known in the art. As a non-limiting example, the polycation may include a cationic peptide or a polypeptide such as, but not limited to, polylysine, polyornithine and/or polyarginine. In another embodiment, the polynucleotides or multimeric structures may be formulated in a lipid-polycation complex which may further include a non-cationic lipid such as, but not limited to, cholesterol or dioleoylphosphatidylethanolamine (DOPE).

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation is composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes may be from about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, $C_{12}$-200 and DLin-KC2-DMA.

In one embodiment, the polynucleotides or multimeric structures disclosed herein are formulated in a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In one embodiment, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid.

In one embodiment, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In one embodiment, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In one embodiment, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In one embodiment, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In one embodiment, the PEG or PEG modified lipid comprises a PEG molecule of an average molecular weight of 2,000 Da. In other embodiments, the PEG or PEG modified lipid comprises a PEG molecule of an average molecular weight of less than 2,000 Da, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA.

In one embodiment, the formulations disclosed herein include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In one embodiment, the formulations disclosed herein include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In one embodiment, the formulations disclosed herein include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In one embodiment, the formulations disclosed herein include about 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In one embodiment, the formulations disclosed herein include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In one embodiment, the formulations disclosed herein include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In one embodiment, the formulations disclosed herein include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In one embodiment, the formulations disclosed herein include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In one embodiment, the formulations disclosed herein include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid: 5-25% neutral lipid: 25-55% cholesterol: 0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.11/34.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

In one embodiment, the lipid nanoparticle formulations described herein may comprise a cationic lipid, a PEG lipid and a structural lipid and optionally comprise a non-cationic lipid.

As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In one embodiment, the cationic lipid may be any cationic lipid described herein such as, but not limited to, DLin-KC2-DMA, DLin-MC3-DMA and L319.

In one embodiment, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In one embodiment, the polynucleotides or multimeric molecules (e.g., multimeric mRNA molecules) of the disclosure may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the lipid nanoparticles may have a diameter from about 10 to 500 nm. In one embodiment, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm. In some embodiments, the cationic lipid nanoparticle has a mean diameter of 50-150 nm. In some embodiments, the cationic lipid nanoparticle has a mean diameter of 80-100 nm.

In one embodiment, the compositions may comprise the polynucleotides or multimeric polynucleotides described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., multimeric polynucleotides), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and about 1.0 mL of water for injection.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, and lubricants, as suited to the particular dosage form desired. Remington's The Science and Practice of Pharmacy, 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Other Components

A nanoparticle composition may include one or more components in addition to those described in the preceding sections. For example, a nanoparticle composition may include one or more small hydrophobic molecules such as a vitamin (e.g., vitamin A or vitamin E) or a sterol.

Nanoparticle compositions may also include one or more permeability enhancer molecules, carbohydrates, polymers, surface altering agents, or other components. A permeability enhancer molecule may be a molecule described by U.S. patent application publication No. 2005/0222064, for example. Carbohydrates may include simple sugars (e.g., glucose) and polysaccharides (e.g., glycogen and derivatives and analogs thereof).

A polymer may be included in and/or used to encapsulate or partially encapsulate a nanoparticle composition. A polymer may be biodegradable and/or biocompatible. A polymer may be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. For example, a polymer may include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D, L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly (vinyl acetate), polyvinyl halides such as poly(vinyl chloride) (PVC), polyvinylpyrrolidone (PVP), polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl (meth)acrylate), poly(butyl(meth)acrylate), poly(isobutyl (meth)acrylate), poly(hexyl(meth)acrylate), poly(isodecyl (meth)acrylate), poly(lauryl(meth)acrylate), poly(phenyl (meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, polyoxamines, poly (ortho)esters, poly(butyric acid), poly(valeric acid), poly (lactide-co-caprolactone), trimethylene carbonate, poly(N- acryloylmorpholine) (PAcM), poly(2-methyl-2-oxazoline) (PMOX), poly(2-ethyl-2-oxazoline) (PEOZ), and polyglycerol.

Surface altering agents may include, but are not limited to, anionic proteins (e.g., bovine serum albumin), surfactants (e.g., cationic surfactants such as dimethyldioctadecyl-ammonium bromide), sugars or sugar derivatives (e.g., cyclodextrin), nucleic acids, polymers (e.g., heparin, polyethylene glycol, and poloxamer), mucolytic agents (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin 14, dornase alfa, neltenexine, and erdosteine), and DNases (e.g., rhDNase). A surface altering agent may be disposed within a nanoparticle and/or on the surface of a nanoparticle composition (e.g., by coating, adsorption, covalent linkage, or other process).

A nanoparticle composition may also comprise one or more functionalized lipids. For example, a lipid may be functionalized with an alkyne group that, when exposed to an azide under appropriate reaction conditions, may undergo a cycloaddition reaction. In particular, a lipid bilayer may be functionalized in this fashion with one or more groups useful in facilitating membrane permeation, cellular recognition, or imaging. The surface of a nanoparticle composition may also be conjugated with one or more useful antibodies. Functional groups and conjugates useful in targeted cell delivery, imaging, and membrane permeation are well known in the art.

In addition to these components, nanoparticle compositions of the disclosure may include any substance useful in pharmaceutical compositions. For example, the nanoparticle composition may include one or more pharmaceutically acceptable excipients or accessory ingredients such as, but not limited to, one or more solvents, dispersion media, diluents, dispersion aids, suspension aids, granulating aids, disintegrants, fillers, glidants, liquid vehicles, binders, surface active agents, isotonic agents, thickening or emulsifying agents, buffering agents, lubricating agents, oils, preservatives, and other species. Excipients such as waxes, butters, coloring agents, coating agents, flavorings, and perfuming agents may also be included. Pharmaceutically acceptable excipients are well known in the art (see for example Remington's *The Science and Practice of Pharmacy*, 21$^{st}$ Edition, A. R. Gennaro; Lippincott, Williams & Wilkins, Baltimore, Md., 2006).

Examples of diluents may include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and/or combinations thereof. Granulating and dispersing agents may be selected from the non-limiting list consisting of potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, and/or combinations thereof.

Surface active agents and/or emulsifiers may include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN®20], polyoxyethylene sorbitan [TWEEN® 60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinylpyrrolidone), diethylene glycol monolaurate, triethanolamine oleate, sodium oleate, potassium oleate, ethyl oleate, oleic acid, ethyl laurate, sodium lauryl sulfate, PLURONIC® F 68, POLOXAMER® 188, cetrimonium bromide, cetylpyridinium chloride, benzalkonium chloride, docusate sodium, and/or combinations thereof.

A binding agent may be starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan); alginates; polyethylene oxide; polyethylene glycol; inorganic calcium salts; silicic acid; polymethacrylates; waxes; water; alcohol; and combinations thereof, or any other suitable binding agent.

Examples of preservatives may include, but are not limited to, antioxidants, chelating agents, antimicrobial preservatives, antifungal preservatives, alcohol preservatives, acidic preservatives, and/or other preservatives. Examples of antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Examples of chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Examples of antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Examples of antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Examples of alcohol preservatives include, but are not limited to, ethanol, polyethylene glycol, benzyl alcohol, phenol, phenolic compounds, bisphenol, chlorobutanol, hydroxybenzoate, and/or phenylethyl alcohol. Examples of acidic preservatives include, but are not limited to, vitamin A, vitamin C, vitamin E, beta-carotene, citric acid, acetic acid, dehydroascorbic acid, ascorbic acid, sorbic acid, and/or phytic acid. Other preservatives include, but are not limited to, tocopherol, tocopherol acetate, deteroxime mesylate, cetrimide, butylated hydroxyanisole (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Examples of buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, calcium lactobionate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, amino-sulfonate buffers (e.g. HEPES), magnesium hydroxide, aluminum hydroxide, alginic acid, pyrogen-free water, isotonic saline, Ringer's solution, ethyl alcohol, and/or combinations thereof. Lubricating agents may selected from the non-limiting group consisting of magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and combinations thereof.

Examples of oils include, but are not limited to, almond, apricot kernel, avocado, babassu, bergamot, black current seed, borage, cade, camomile, canola, caraway, camauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils as well as butyl stearate, caprylic triglyceride, capric triglyceride, cyclomethicone, diethyl sebacate, dimethicone 360, simethicone, isopropyl myristate, mineral oil, octyldodecanol, oleyl alcohol, silicone oil, and/or combinations thereof.

Additional and Alternative Examples of Formulations

Nanoparticle compositions may include a lipid component and one or more additional components, such as a therapeutic agent. A nanoparticle composition may be designed for one or more specific applications or targets. The elements of a nanoparticle composition may be selected based on a particular application or target, and/or based on the efficacy, toxicity, expense, ease of use, availability, or other feature of one or more elements. Similarly, the particular formulation of a nanoparticle composition may be selected for a particular application or target according to, for example, the efficacy and toxicity of particular combinations of elements.

The lipid component of a nanoparticle composition of the disclosure may include, for example, a lipid according to formula (I), a phospholipid (such as an unsaturated lipid, e.g., DOPE or DSPC), a PEG lipid, and a structural lipid. The elements of the lipid component may be provided in specific fractions.

In some embodiments, the lipid component of a nanoparticle composition includes a lipid according to formula (I), a phospholipid, a PEG lipid, and a structural lipid. In certain embodiments, the lipid component of the nanoparticle composition includes about 30 mol % to about 60 mol % compound of formula (I), about 0 mol % to about 30 mol % phospholipid, about 18.5 mol % to about 48.5 mol % structural lipid, and about 0 mol % to about 10 mol % of PEG lipid, provided that the total mol % does not exceed 100%. In some embodiments, the lipid component of the nanoparticle composition includes about 35 mol % to about 55 mol % compound of formula (I), about 5 mol % to about 25 mol % phospholipid, about 30 mol % to about 40 mol % structural lipid, and about 0 mol % to about 10 mol % of PEG lipid. In a particular embodiment, the lipid component includes about 50 mol % said compound, about 10 mol % phospholipid, about 38.5 mol % structural lipid, and about 1.5 mol % of PEG lipid. In another particular embodiment, the lipid component includes about 40 mol % said compound, about 20 mol % phospholipid, about 38.5 mol % structural lipid, and about 1.5 mol % of PEG lipid. In some embodiments, the phospholipid may be DOPE or DSPC. In other embodiments, the PEG lipid may be PEG-DMG and/or the structural lipid may be cholesterol.

Nanoparticle compositions may be designed for one or more specific applications or targets. For example, a nanoparticle composition may be designed to deliver a therapeutic agent such as an RNA to a particular cell, tissue, organ, or system or group thereof in a mammal's body. Physiochemical properties of nanoparticle compositions may be altered in order to increase selectivity for particular bodily targets. For instance, particle sizes may be adjusted based on the fenestration sizes of different organs. The therapeutic agent included in a nanoparticle composition may also be selected based on the desired delivery target or targets. For example, a therapeutic agent may be selected for a particular indication, condition, disease, or disorder and/or for delivery to a particular cell, tissue, organ, or system or group thereof (e.g., localized or specific delivery). In certain embodiments, a nanoparticle composition may include an mRNA encoding a polypeptide of interest capable of being translated within a cell to produce the polypeptide of interest. Such a composition may be designed to be specifically delivered to a particular organ. In particular embodiments, a composition may be designed to be specifically delivered to a mammalian liver.

The amount of a therapeutic agent in a nanoparticle composition may depend on the size, composition, desired target and/or application, or other properties of the nanoparticle composition as well as on the properties of the therapeutic agent. For example, the amount of an RNA useful in a nanoparticle composition may depend on the size, sequence, and other characteristics of the RNA. The relative amounts of a therapeutic agent and other elements (e.g., lipids) in a nanoparticle composition may also vary. In some embodiments, the wt/wt ratio of the lipid component to a therapeutic agent in a nanoparticle composition may be from about 5:1 to about 60:1, such as 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1, and 60:1. For example, the wt/wt ratio of the lipid component to a therapeutic agent may be from about 10:1 to about 40:1. In preferred embodiments, the wt/wt ratio is about 20:1. The amount of a therapeutic agent in a nanoparticle composition may, for example, be measured using absorption spectroscopy (e.g., ultraviolet-visible spectroscopy).

In some embodiments, a nanoparticle composition includes one or more RNAs, and the one or more RNAs, lipids, and amounts thereof may be selected to provide a specific N:P ratio. The N:P ratio of the composition refers to the molar ratio of nitrogen atoms in one or more lipids to the number of phosphate groups in an RNA. In general, a lower N:P ratio is preferred. The one or more RNA, lipids, and amounts thereof may be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio may be from about 2:1 to about 8:1. In other embodiments, the N:P ratio is from about 5:1 to about 8:1. For example, the N:P ratio may be about 5.0:1, about 5.5:1, about 5.67:1, about 6.0:1, about 6.5:1, or about 7.0:1. For example, the N:P ratio may be about 5.67:1.

Physical Properties

The characteristics of a nanoparticle composition may depend on the components thereof. For example, a nanoparticle composition including cholesterol as a structural lipid may have different characteristics than a nanoparticle composition that includes a different structural lipid. Similarly, the characteristics of a nanoparticle composition may depend on the absolute or relative amounts of its components. For instance, a nanoparticle composition including a higher molar fraction of a phospholipid may have different characteristics than a nanoparticle composition including a lower molar fraction of a phospholipid. Characteristics may also vary depending on the method and conditions of preparation of the nanoparticle composition.

Nanoparticle compositions may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvem Instruments Ltd, Malvem, Worcestershire, UK) may also be used to measure multiple characteristics of a nanoparticle composition, such as particle size, polydispersity index, and zeta potential.

The mean size of a nanoparticle composition of the disclosure may be between 10s of nm and 100s of nm. For example, the mean size may be from about 40 nm to about 150 nm, such as about 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm. In some embodiments, the mean size of a nanoparticle composition may be from about 50 nm to about 100 nm, from about 50 nm to about 90 nm, from about 50 nm to about 80 nm, from about 50 nm to about 70 nm, from about 50 nm to about 60 nm, from about 60 nm to about 100 nm, from about 60 nm to about 90 nm, from about 60 nm to about 80 nm, from about 60 nm to about 70 nm, from about 70 nm to about 100 nm, from about 70 nm to about 90 nm, from about 70 nm to about 80 nm, from about 80 nm to about 100 nm, from about 80 nm to about 90 nm, or from about 90 nm to about 100 nm. In certain embodiments, the mean size of a nanoparticle composition may be from about 70 nm to about 100 nm. In a particular embodiment, the mean size may be about 80 nm. In other embodiments, the mean size may be about 100 nm.

A nanoparticle composition of the disclosure may be relatively homogenous. A polydispersity index may be used to indicate the homogeneity of a nanoparticle composition, e.g., the particle size distribution of the nanoparticle compositions. A small (e.g., less than 0.3) polydispersity index generally indicates a narrow particle size distribution. A nanoparticle composition of the disclosure may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition may be from about 0.10 to about 0.20.

The zeta potential of a nanoparticle composition may be used to indicate the electrokinetic potential of the composition. For example, the zeta potential may describe the surface charge of a nanoparticle composition. Nanoparticle compositions with relatively low charges, positive or negative, are generally desirable, as more highly charged species may interact undesirably with cells, tissues, and other elements in the body. In some embodiments, the zeta potential of a nanoparticle composition of the disclosure may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

The efficiency of encapsulation of a therapeutic agent describes the amount of therapeutic agent that is encapsulated or otherwise associated with a nanoparticle composition after preparation, relative to the initial amount provided. The encapsulation efficiency is desirably high (e.g., close to 100%). The encapsulation efficiency may be measured, for example, by comparing the amount of therapeutic agent in a solution containing the nanoparticle composition before and after breaking up the nanoparticle composition with one or more organic solvents or detergents. Fluorescence may be used to measure the amount of free therapeutic agent (e.g., RNA) in a solution. For the nanoparticle compositions of the disclosure, the encapsulation efficiency of a therapeutic agent may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

A nanoparticle composition disclosed herein may optionally comprise one or more coatings. For example, a nanoparticle composition may be formulated in a capsule, film, or tablet having a coating. A capsule, film, or tablet including a composition of the disclosure may have any useful size, tensile strength, hardness, or density.

As used herein, "treating" or "treat" describes the management and care of a patient for the purpose of combating a disease, condition, or disorder and includes the administration of an active ingredient of the present disclosure to alleviate the symptoms or complications of a disease, condition or disorder, or to eliminate the disease, condition or disorder. The term "treat" can also include treatment of a cell in vitro or an animal model.

An active ingredient of the present disclosure, can or may also be used to prevent a relevant disease, condition or disorder, or used to identify suitable candidates for such purposes.

As used herein, "preventing," "prevent," or "protecting against" describes reducing or eliminating the onset of the symptoms or complications of such disease, condition or disorder.

As used herein, "combination therapy" or "co-therapy" includes the administration of an active ingredient of the present disclosure, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents.

A "pharmaceutical composition" is a formulation containing the active ingredient of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of an active ingredient of the disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

An active ingredient of the present disclosure can be administered to a subject in many of the well-known methods currently used for chemotherapeutic treatment. For example, for treatment of cancers, an active ingredient of the present disclosure may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

An "effective amount" of the polynucleotides (e.g., RNA or mRNA) or multimeric structures disclosed herein is based, at least in part, on the target tissue, target cell type, means of administration, physical characteristics of the polynucleotide (e.g., size, and extent of modified nucleosides) and other components of the multimeric structures, and other determinants. In general, an effective amount of RNA or the multimeric structure provides an induced or boosted peptide production in the cell, preferably more efficient than a composition containing a corresponding unmodified polynucleotide encoding the same peptide or about the same or more efficient than separate mRNAs that are not part of a multimeric structure. Increased peptide production may be demonstrated by increased cell transfection (i.e., the percentage of cells transfected with the multimeric structures), increased protein translation from the polynucleotide, decreased nucleic acid degradation (as demonstrated, e.g., by increased duration of protein translation from a modified polynucleotide), or altered peptide production in the host cell.

The mRNA of the present disclosure may be designed to encode polypeptides of interest selected from any of several target categories including, but not limited to, biologics, antibodies, vaccines, therapeutic proteins or peptides, cell penetrating peptides, secreted proteins, plasma membrane proteins, cytoplasmic or cytoskeletal proteins, intracellular membrane bound proteins, nuclear proteins, proteins associated with human disease, targeting moieties or those proteins encoded by the human genome for which no therapeutic indication has been identified but which nonetheless have utility in areas of research and discovery. "Therapeutic protein" refers to a protein that, when administered to a cell has a therapeutic, diagnostic, and/or prophylactic effect and/or elicits a desired biological and/or pharmacological effect.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

In certain embodiments, compositions in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

The pharmaceutical compositions containing active ingredient of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the active ingredient of the present disclosure is delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

More examples of pharmaceutically acceptable excipients, dosage forms, kits, routes of administration, and methods of treatment can be found in WO 2015051173 and WO 2015051169, the contents of each of which are herein incorporated by reference in their entireties.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds (including cap analogs) and polynucleotides disclosed herein, or designed, selected and/or optimized by methods described above, once produced, can be characterized using a variety of assays known to those skilled in the art to determine whether the compounds have biological activity. For example, the molecules can be characterized by conventional assays, including but not limited to protein production assays (e.g., cell-free translation assays or cell based expression assays), degradation assays, cell culture assays (e.g., of neoplastic cells), animal models (e.g., rats, mice, rabbits, dogs, or pigs), and those assays described below, to determine whether they have a predicted activity, e.g., binding activity and/or binding specificity, and stability.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

Example 1: Syntheses of Compounds of the Disclosure
Synthesis of Compound 1
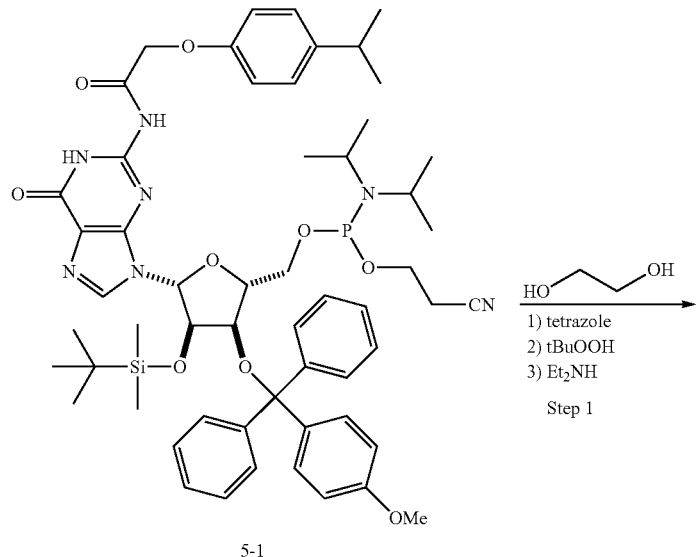
5-1
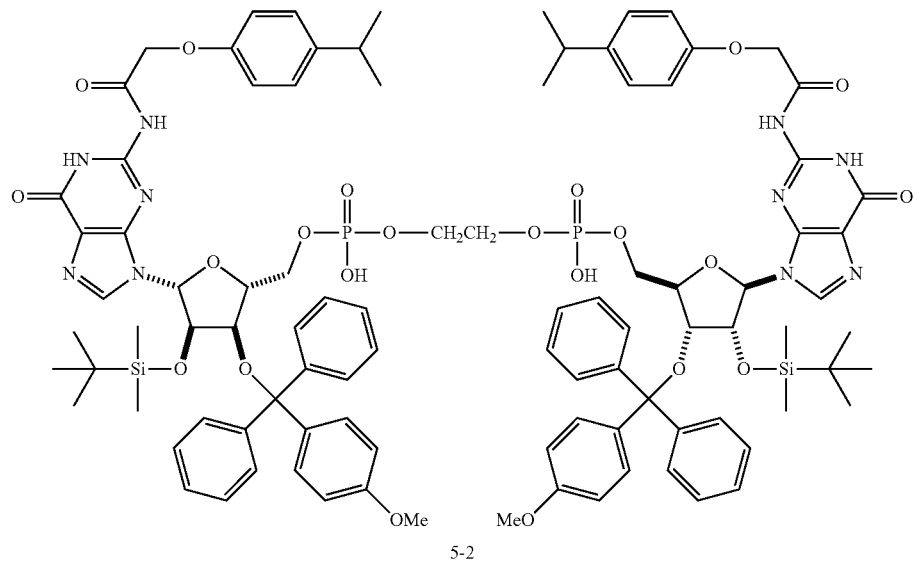
5-2
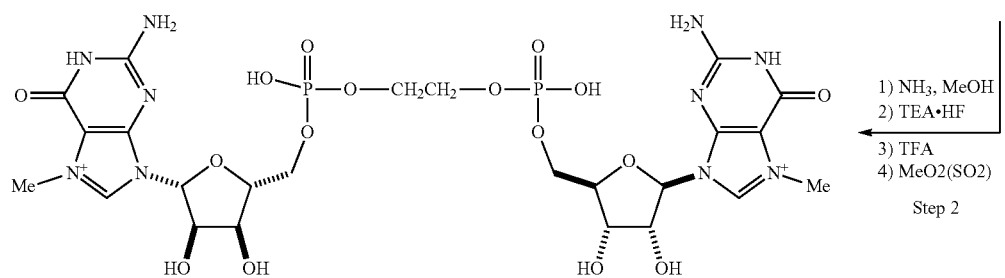
1

Step 1: Synthesis of Bis-Phosphate Ester (5-2)

To a solution of 5-1 (1.0 g, 0.94 mmol) and ethylene glycol (0.0263 mL, 0.47 mmol) in acetonitrile (20 mL) was added 1H-tetrazole in acetonitrile (0.45 M solution, 3.14 mL, 1.41 mmol) dropwise over 3 minutes. After stirring at 20° C. for 1.5 h, the reaction mixture was cooled to <−20° C. and treated with t-butylhydroperoxide in n-decane (5.5 M solution, 0.514 mL, 2.83 mmol) over 5 min. The reaction mixture was allowed to warm to 20° C. overnight. The reaction was quenched with H$_2$O (Milli Q grade, 60 mL) followed by dichloromethane (60 mL). The aqueous layer was separated from the organic layer and extracted with dichloromethane (60 mL×2). The combined organic layers were dried over sodium sulfate, filtered through a sintered glass funnel and concentrated in vacuo at 30° C. to give a pale yellow oil (1.8 g). The product was purified by column chromatography (25 g silica gel) eluting gradient with dichloromethane to 8% methanol in dichloromethane. The product-containing fractions were combined and concentrated in vacuo at 30° C. to give the title compound as an off-white solid (449 mg, 47% yield).

$^1$H NMR (400 MHz, DMSO-d6) −0.49 (s, 6H, 2 CH$_3$—Si), 0.03 (s, 6H, 2 CH$_3$—Si), 0.79 (s, 18H, 2 tBu-Si), 1.14 (s, 12H, 2Me$_2$CH), 2.71 (m, 2H, 2 CHMe$_2$), 2.81 (m, 4H, 2 CH$_2$CN), 3.17 (m, 2H, 2H-3'), 3.61 (m, 4H, 2H$_2$-5'), 3.70 & 3.73 (2s, 12H, 4 OCH$_3$), 3.91 (m, 2H, 2H-2'), 3.99 (m, 4H, 2OCH$_2$CH$_2$CN), 4.82 (s, 4H, 2OCH$_2$Ar), 4.85 (m, 2H, 2H-4'), 6.06 (d, 2H, 2H-1'), 6.87-8.21 (m, 34H, 8 Ar), 11.56 (br s, 2H, 2 NH-1), 11.81 (s, 2H, 2H-8); $^{31}$P NMR (161 MHz, D$_2$O) δ 1.01.

Step 2: Synthesis of Compound 1

A solution of 5-2 (0.31 g, 0.154 mmol) and methanolic ammonia (2 M solution, 5 mL, 10.0 mmol) was stirred at 20° C. for 4 h and concentrated in vacuo at 20° C. to give an oil. The oil was dissolved in acetonitrile (6 mL) and N,N-dimethylformamide (3 mL), and treated with triethylamine trihydrofluoride (0.064 mL, 0.391 mmol) at 20° C. After 3 h, triethylamine trihydrofluoride (0.192 mL, 1.173 mmol) was added to the reaction mixture at 20° C. and the mixture was stirred at 20° C. for 3 days. To the reaction mixture was added trifluoroacetic acid (0.015 mL, 0.195 mmol) and 1-dodecanethiol (0.103 mL, 0.409 mmol) at 20° C. over 8 minutes. The reaction mixture was stirred at 20° C. for 2 days. 1-dodecanethiol (0.052 mL) followed by trifluoroacetic acid (0.345 mL) was added to the reaction mixture, and the mixture was stirred overnight. After 1 day, the reaction was quenched with H$_2$O (Milli Q grade, 15 mL) and dichloromethane (10 mL). The aqueous layer was separated from the organic layer and extracted with dichloromethane (10 mL). The combined organic layers were purified by column chromatography (50 g C18 column) eluting with 10 mM N,N-dimethylhexylammonium bicarbonate buffer (pH 7.5) to 30% acetonitrile in 10 mM N,N-dimethylhexylammonium bicarbonate buffer (pH 7.5). The product-containing fractions were combined and concentrated in vacuo to give the title compound (197 mg).

$^1$H NMR (400 MHz, D$_2$O) δ 0.84 (s, 9H, 3 Me(CH$_2$)$_5$N), 1.29 (s,) 1.29 (m, 18H, 3 MeCH$_2$CH$_2$CH$_2$CH$_2$CH$_2$N), 1.67 (m, 6H, 3 CH$_2$CH$_2$N), 2.84 (s, 18H, 3 Me$_2$N), 3.09 (m, 6H, 3 NCH$_2$), 3.98-4.18 (m, 4H, 2H$_2$-5), 4.24 (m, 2H, 2H-2'), 4.43 (m, 2H, 2H-3'), 4.71 (m, 2H, 2H-2'), 5.80 (d, 2H, 2H-1'), 7.97 (s, 2H, 2H-8); $^{31}$P NMR (161 MHz, D$_2$O) δ 1.03.

Synthesis of Compound 2

Step 1:

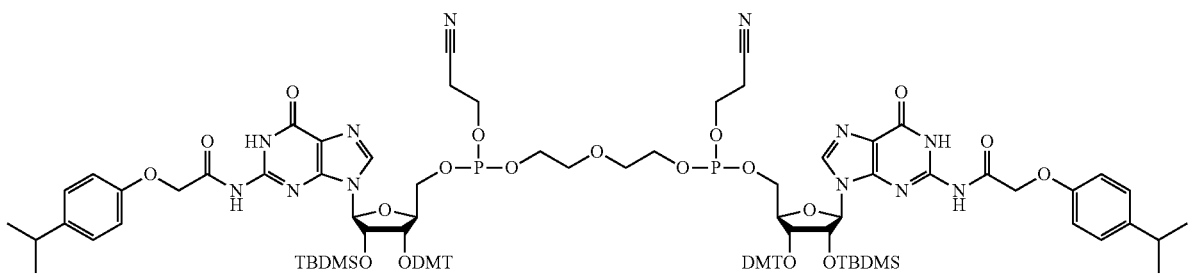

To a flame dried round bottom flask containing 4A molecular sieves in acetonitrile (4 ml) was added 2'-tBDSilyl-3'-DMT-Guanosine(n-iPr-PAC)-5'-CED phosphoramidite (0.3 g, 0.28 mmol), followed by diethylene glycol (0.03 ml, 0.31 mmol). 1H-tetrazole (0.45M in acetonitrile, 0.14 ml, 0.06 mmol) was then added and the resulting reaction mixture was stirred at ambient temperature under N$_2$ until $^{31}$P NMR indicated the disappearance of phosphoramidite (3 days). Tert-butylhydroperoxide (5.5M in decane, 0.11 ml, 0.6 mmol) was added and the resulting reaction mixture was stirred overnight at ambient temperature under N$_2$. The reaction was then filtered and concentrated to provide crude product which was used without further purification. $^{31}$P NMR (CD$_3$CN) δ 139.9 (1P), 140.3 (1P).

Step 2:

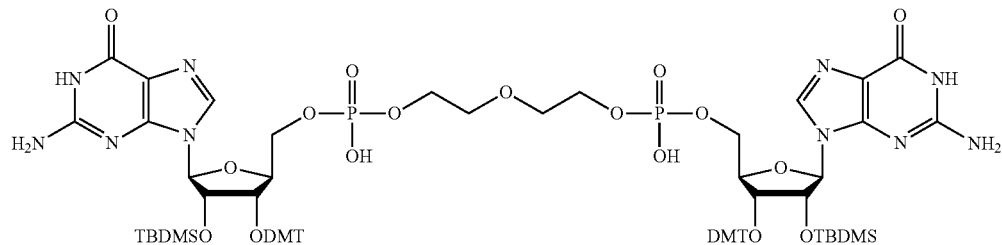

To a suspension containing the product from Step 1 (0.28 mmol) in THF (5 ml) was added methylamine (2M in THF, 1.4 ml, 2.8 mmol). The resulting reaction mixture was stirred at ambient temperature under $N_2$ until $^{31}P$ NMR indicated consumption of starting material and LCMS indicated removal of n-isopropyl-PAC protecting group (24 hours). The reaction was diluted with water and extracted with dichloromethane. The organics were concentrated to provide crude product which was used without further purification. $^{31}P$ NMR (CD$_3$CN) δ −1.22 (2P).

Step 3:

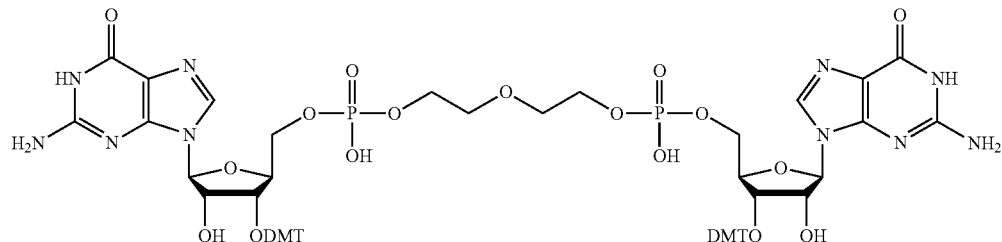

To a solution containing the product from Step 2 (0.28 mmol) in THF (4 ml) was added tetrabutylammonium fluoride (1M in THF, 3 ml, 3 mmol). The resulting reaction mixture was stirred at ambient temperature under $N_2$ until LCMS indicated removal of the 2' silyl protecting group (16 hours). The reaction was diluted with water and extracted with chloroform. The organics were concentrated to provide crude product which was used without further purification.

Step 4:

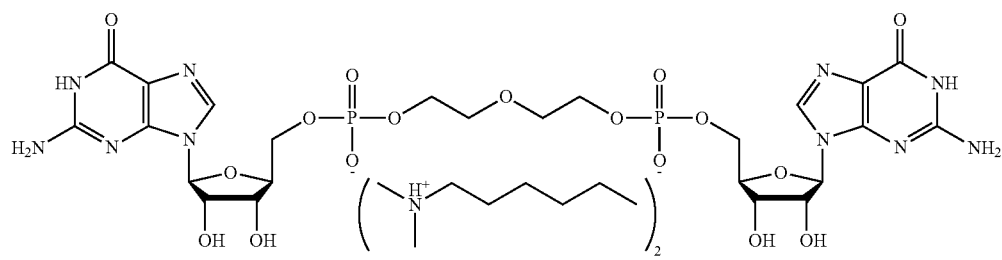

To a solution containing the product from Step 3 (0.28 mmol) in THF (3 ml) was added trifluoroacetic acid (0.35 ml, 4.5 mmol) followed by 1-decanethiol (0.22 ml, 0.9 mmol). The resulting reaction mixture was stirred at ambient temperature overnight then concentrated under reduced pressure. The resulting crude material was purified by weak anion exchange column chromatography (Sepharose, 0-100% 1M triethylammonium bicarbonate/water) to provide 0.117 g of the desired product as a white solid.

Step 5:

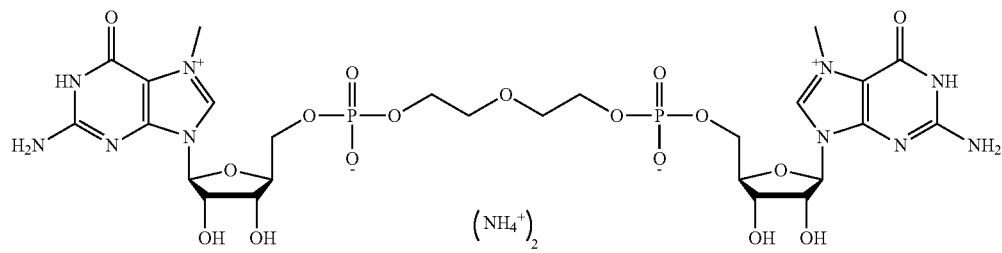

The product obtained in Step 4 (0.117 g, 0.11 mmol) was dissolved in water and the pH was adjusted to 4 by addition of glacial acetic acid. Dimethyl sulfate (0.16 ml, 1.7 mmol) was added dropwise over 90 minutes and pH was maintained between 4.0-4.1 by addition of 5M NaOH. The reaction was stirred an additional 30 minutes following addition then diluted with water to 900 ml. The product was purified by weak anion exchange column chromatography (Sepharose, 0-100% 1M triethylammonium bicarbonate/water) to provide the product as the triethylammonium salt. The triethylammonium salt was then converted to the dimethylhexylammonium salt by reverse phase chromatography (Isco, C18, 0-40% 10 mM dimethylhexylammonium bicarbonate/acetonitrile). Lastly, the product was converted to the ammonium salt by precipitation with ammonium perchlorate/acetone. $^1$H NMR (D$_2$O) δ 3.67 (4H, s), 3.94 (4H, bs), 4.03 (6H, s), 4.15 (2H, m), 4.30 (2H, bs), 4.38 (2H, m), 4.57 (2H, m), 5.94 (2H, m). $^{31}$P NMR (D$_2$O) δ 0.32 (2P, s).

Compounds 25 was synthesized in a manner similar to that described above for Compound 2.

Compound 25:

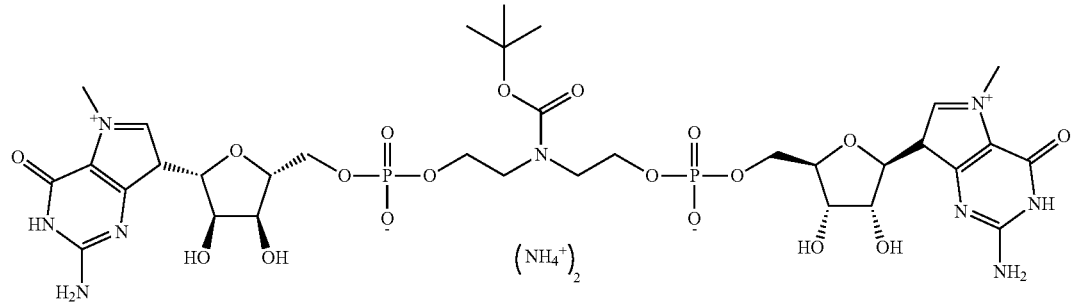

Synthesis of Compound 7:
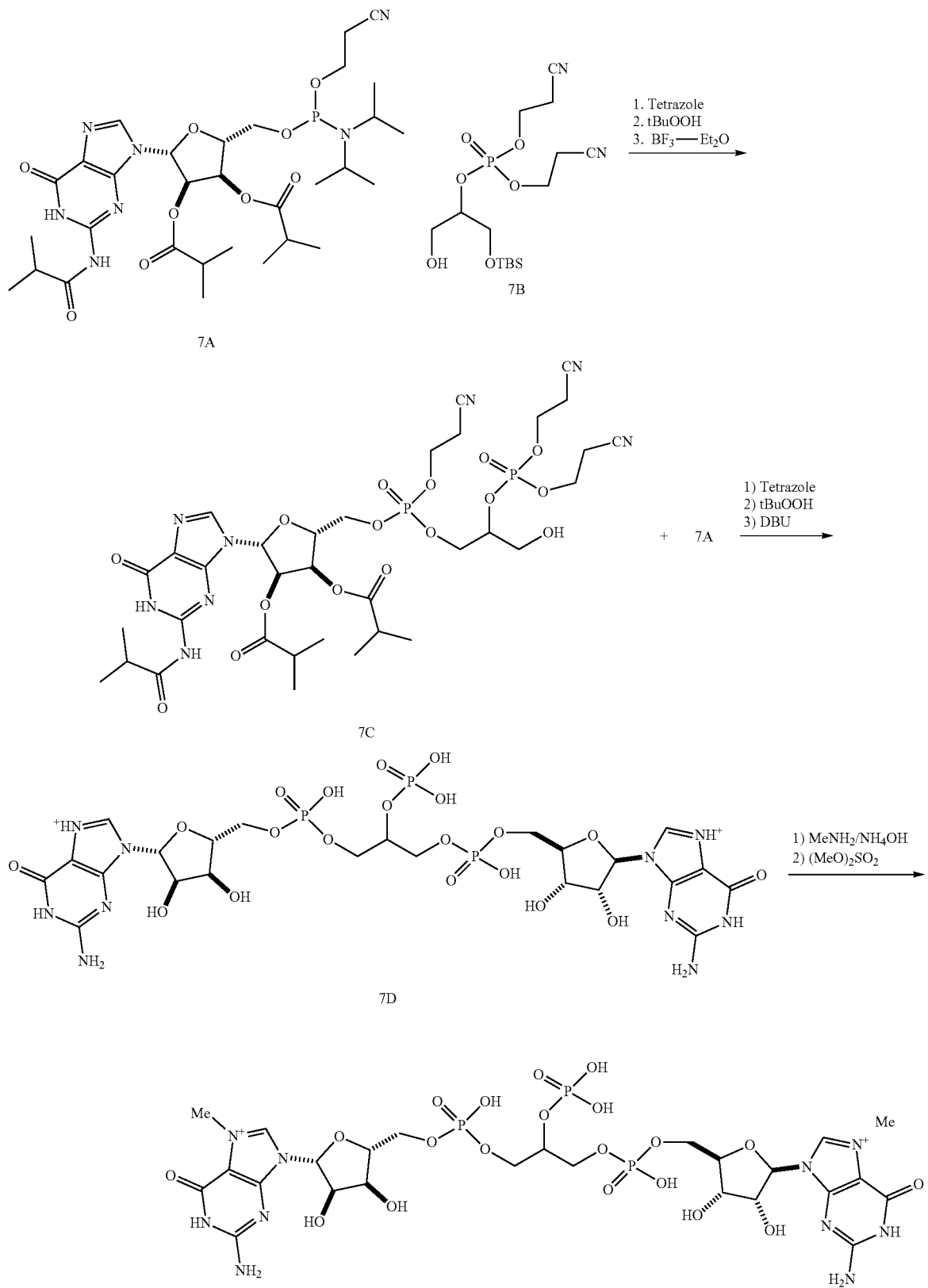

Step 1 Synthesis of (2R,3R,4R,5R)-2-((((2-((bis(2-cyanoethoxy)phosphoryl)oxy)-3-hydroxypropoxy)(2-cyanoethoxy)phosphoryl)oxy)methyl)-5-(2-isobutyramido-6-oxo-1,6-dihydro-9H-purin-9-yl)tetrahydrofuran-3,4-diyl bis(2-methylpropanoate) (7C).

A 250 mL single-neck round-bottom flask equipped with a stir bar and nitrogen inlet adapter was charged with (2R,3R,4R,5R)-2-((((2-cyanoethoxy)(diisopropylamino)phosphanyl)oxy)methyl)-5-(2-isobutyramido-6-oxo-1,6-dihydro-9H-purin-9-yl)tetrahydrofuran-3,4-diyl bis(2-methylpropanoate) (7A) [3.37 g, 4.86 mmol, 1 eq.] in 27 mL of $CH_3CN$ ($K_f$=2743 ppm). 3 Å molecular sieves were added to the flask. 1-((tert-butyldimethylsilyl)oxy)-3-hydroxypropan-2-yl bis(2-cyanoethyl) phosphate (7B) [1.91 g, 4.86 mmol, 1 eq.] was azeotroped twice with $CH_3CN$, dissolved in 30 mL of $CH_3CN$, and added to the reaction flask to give a final $K_f$ reading of 1507 ppm. The flask was charged with 1H-tetrazole [11.87 mL 0.5 M, 5.34 mmol, 1.1 eq.], resulting in a cloudy, white mixture after 5 min. LCMS indicated complete consumption of the starting guanosine analog after 45 min, at which point the flask was cooled to 0° C. in an ice-water bath and charged with tert-Butyl hydroperoxide [1.77 mL 5.5 M, 9.72 mmol, 2 eq.]. The reaction mixture stirred at RT for 15 h, and LCMS showed consumption of the intermediate after 15 h. Filtration and concentration via rotary evaporation afforded 6.1 g of a yellow suspension, which was purified through column chromatography on silica gel (80 g) with 5% MeOH/DCM. Concentration of the product-containing fractions yielded 3.7 g (76%) of protected intermediate, (2R,3R,4R,5R)-5-{[(2-{[bis(2-cyanoethoxy)phosphoryl]oxy}-3-[(tert-butyldimethylsilyl)oxy]propoxy(2-cyanoethoxy)phosphoryl)oxy]methyl}-2-[2-(2-methylpropanamido)-6-oxo-1H-purin-9-yl]-4-[(2-methylpropanoyl)oxy]oxolan-3-yl 2-methylpropanoate, as a viscous, colorless oil. A 500 mL single-neck round-bottom flask equipped with a stir bar and nitrogen inlet adapter was charged with (2R,3R,4R,5R)-5-{[(2-{[bis(2-cyanoethoxy)phosphoryl]oxy}-3-[(tert-butyldimethylsilyl)oxy]propoxy(2-cyanoethoxy)phosphoryl)oxy]methyl}-2-[2-(2-methylpropanamido)-6-oxo-1H-purin-9-yl]-4-[(2-methylpropanoyl)oxy]oxolan-3-yl 2-methylpropanoate [3.6 g, 3.6 mmol, 1 eq.] and 100 mL of DCM. The flask was then charged with $BF_3$ etherate [0.89 mL, 7.19 mmol, 2 eq.], immediately causing the colorless solution to turn orange. LC/MS showed little consumption of the starting material after 6 min, so another equiv. of $BF_3$ etherate was added. An additional equiv. (total of 4.0 equiv.) was added after a total 50 min of reaction time. LC/MS indicated complete consumption of the starting material after 80 min, at which point the reaction mixture was neutralized with 100 mL of 5% $NaHCO_{3(aq)}$ and stirred for 5 min. The aqueous and organic layers in the cloudy, light orange mixture were separated by using a 500 mL separatory funnel. The aqueous layer was back-extracted with an additional 100 mL of DCM. The combined organic layers were concentrated via rotary evaporation and purified through column chromatography on silica gel (80 g) with 0-10% MeOH/DCM affording 1.15 g of (2R,3R,4R,5R)-2-((((2-((bis(2-cyanoethoxy)phosphoryl)oxy)-3-hydroxypropoxy)(2-cyanoethoxy)phosphoryl)oxy)methyl)-5-(2-isobutyramido-6-oxo-1,6-dihydro-9H-purin-9-yl)tetrahydrofuran-3,4-diyl bis(2-methylpropanoate) (7C) in 36% yield. $^{31}$P NMR ($D_2O$) δ −2.1 (1P), 6-2.3 (1P); MS (m/z) 885 [M-H].

Step 2: Synthesis of Compound 7

A 250 mL single-neck round-bottom flask equipped with a stir bar and nitrogen inlet adapter was charged with (2R,3R,4R,5R)-2-({[(2-cyanoethoxy)(diisopropylamino)phosphanyl]oxy}methyl)-5-[2-(2-methylpropanamido)-6-oxo-1H-purin-9-yl]-4-[(2-methylpropanoyl)oxy]oxolan-3-yl 2-methylpropanoate (7A)[1.64 g, 2.36 mmol, 1.8 eq.] in 12 mL of MeCN and stirred over 4 Å molecular sieves over about 48 h ($K_f$<1000 ppm). (2R,3R,4R,5R)-5-{[(2-{[bis(2-cyanoethoxy)phosphoryl]oxy}-3-hydroxypropoxy(2-cyanoethoxy)phosphoryl)oxy]methyl}-2-[2-(2-methylpropanamido)-6-oxo-1H-purin-9-yl]-4-[(2-methylpropanoyl)oxy]oxolan-3-yl 2-methylpropanoate(7C) [1.15 g, 1.3 mmol, 1 eq.] were dissolved in 4 mL of MeCN and added to the reaction flask to give a final $K_f$ reading of <800 ppm. The flask was charged with 1H-tetrazole [2.88 mL 0.5 M, 1.3 mmol, 1 eq.], resulting in a cloudy white mixture after 5 min. LCMS indicated complete consumption of the starting guanosine analog after 45 min, at which point the flask was cooled to 0° C. in an ice-water bath and charged with tert-Butyl hydroperoxide [0.47 mL 5.5 M, 2.59 mmol, 2 eq.]. The reaction mixture stirred at RT overnight, and LCMS showed consumption of the intermediate by 15 h. Filtration and concentration via rotary evaporation afforded a yellow suspension, which was purified through column chromatography with 5% MeOH/DCM, affording 520 mg of the protected intermediate (i.e., the intermediate carrying all protecting groups) in 27% yield.

A 100 mL single-neck round-bottom flask equipped with a stir bar and nitrogen inlet adapter was charged with 0.52 g of the starting material, 9 mL of MeCN, and 1,8-Diazabicyclo[5.4.0]undec-7-ene [0.78 mL, 5.22 mmol, 15 eq.]. After 1 hour the light brown reaction mixture was concentrated to dryness and taken up in 8.5 mL of water. The solution was added to methylamine [2.61 mL 2 M, 5.22 mmol, 15 eq.] and 2.6 mL of ammonium hydroxide, and stirred at 60° C. for 2 hours, then cooled to room temperature and loaded onto a C18 column eluting with DMHA buffer/CAN. The desired fractions were partially concentrated and lyophilized overnight, affording 150 mg of the fully deprotected intermediate, [1,3-bis({[(2R,3S,4R,5R)-5-(2-amino-6-oxo-1H-purin-9-yl)-3,4-dihydroxyoxolan-2-yl]methoxy(hydroxy)phosphoryl}oxy)propan-2-yl]oxyphosphonic acid (7D), in 50% yield.

A 250 mL single-neck round-bottom flask was charged with [1,3-bis({[(2R,3S,4R,5R)-5-(2-amino-6-oxo-1H-purin-9-yl)-3,4-dihydroxyoxolan-2-yl]methoxy(hydroxy)phosphoryl}oxy)propan-2-yl]oxyphosphonic acid [0.15 g, 0.17 mmol, 1 eq.] and 20 mL of water. The solution is adjusted to pH=4.0 with AcOH. Dimethyl sulfate [1.25 mL, 13.04 mmol, 75 eq.] was added in 5 uL portions over 2 hours via syringe pump while keeping the pH at 4.0 with 7 uL additions of 5 M $NaOH_{(aq)}$. LCMS indicated complete dimethylation. The reaction mixture was diluted with 500 mL of water and extracted twice with 400 mL of DCM. The aqueous phase was adjusted to pH=7.8 to match the 1 M triethyl ammonium bicarbonate buffer. The crude mixture was pumped onto a Sepharose column. The product-containing fractions were combined, mixed with 60 mL of 100 mM DMHA buffer, and pumped onto a 150 g C18 column. The desired fraction was partially concentrated and then lyophilized overnight. 130 mg of the dimethylated product (Compound 7) were obtained in 83% yield. $^{31}$P NMR ($D_2O$) δ 0.9 (1P), δ 0.1 (1P), δ −0.8 (1P); MS (m/z) 891.2 [M-H]⁻.

Synthesis of Compound 3

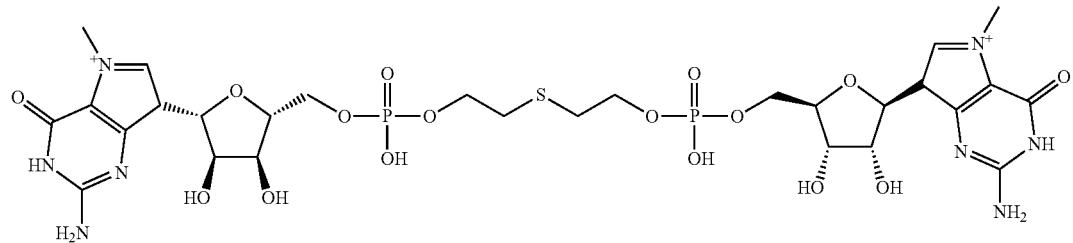 [SMILES: C[N+]1=CC([C@@H]2O[C@H](COP(=O)(O)OCCSCCOP(=O)(O)OC[C@H]3O[C@@H](C4C=[N+](C)c5c4nc(N)[nH]c5=O)[C@H](O)[C@@H]3O)[C@@H](O)[C@H]2O)c2nc(N)[nH]c(=O)c21]

Step 1

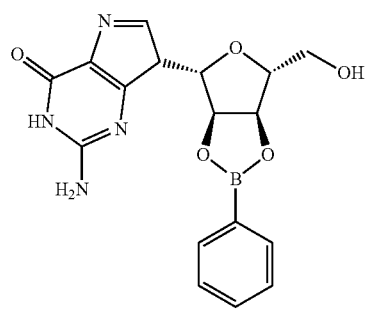 [SMILES: Nc1nc2c(c(=O)[nH]1)N=CC2[C@@H]1O[C@H](CO)[C@H]2OB(c3ccccc3)O[C@H]21]

To a suspension containing guanosine (10.0 g, 35.3 mmol) in acetonitrile (100 ml) was added sodium sulfate (12.5 g, 88.3 mmol) followed by phenylboronic acid (4.52 g, 37.0 mmol). The resulting reaction mixture was heated to reflux and stirred under $N_2$ until NMR indicated the complete conversion of guanosine (3 hours). The reaction mixture was cooled to ambient temperature and the product was isolated by filtration to give 11.1 g of a white solid, used without further purification.

Step 2:

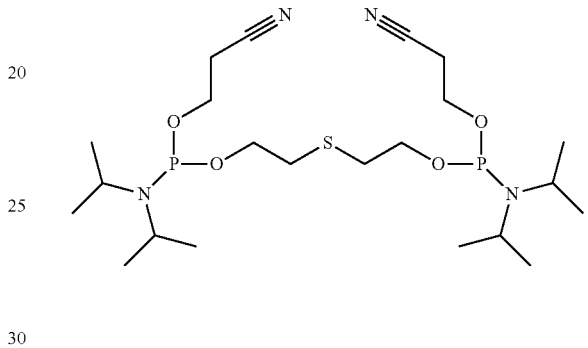

To a solution containing thiodiethanol (0.75 g, 6.1 mmol) in dichloromethane (60 ml) was added diisopropylethylamine (3.2 ml, 18.3 mmol) and the reaction was cooled to 0° C. 2-cyanoethyl N,N-diisopropylchlorophosphoramidite (2.8 ml, 12.8 mmol) was added dropwise over 15 minutes. The resulting reaction mixture was allowed to warm to ambient temperature and stirred under $N_2$. After 2 hours, the reaction was diluted with water and extracted with dichloromethane. The organics were washed with water and brine, dried over sodium sulfate and concentrated. The product was used without further purification.

Step 3:

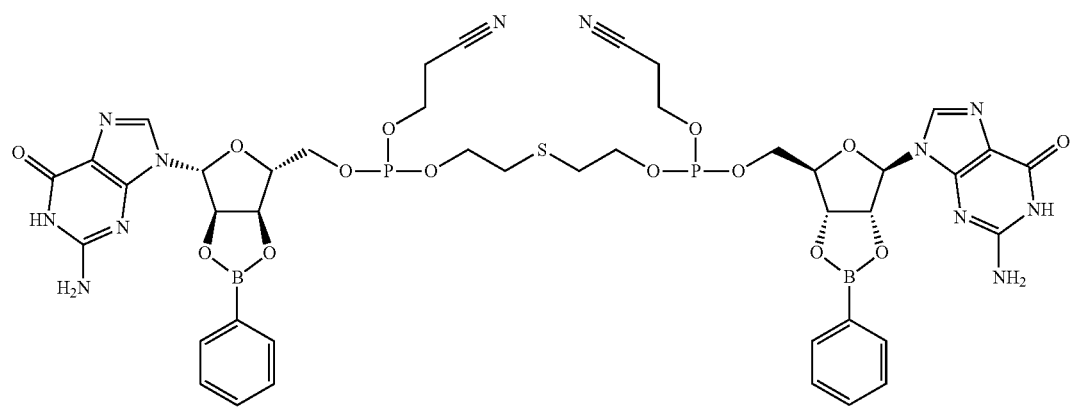 [SMILES: N#CCCOP(OCCSCCOP(OCCC#N)OC[C@H]1O[C@@H](n2cnc3c(=O)[nH]c(N)nc32)[C@@H]2OB(c3ccccc3)O[C@@H]21)OC[C@H]1O[C@@H](n2cnc3c(=O)[nH]c(N)nc32)[C@@H]2OB(c3ccccc3)O[C@@H]21]

To a solution containing the product from Step 1 (0.71 g, 1.92 mmol) and Step 2 (0.5 g, 0.96 mmol) in DMF (15 ml) was added 5-(ethylthio)-1H-tetrazole (0.1 g, 0.72 mmol). The resulting reaction mixture was stirred at ambient temperature under $N_2$ until $^{31}P$ NMR indicated conversion to desired product (3 hours). The reaction mixture was concentrated under reduced pressure and used without further purification.

Step 4:

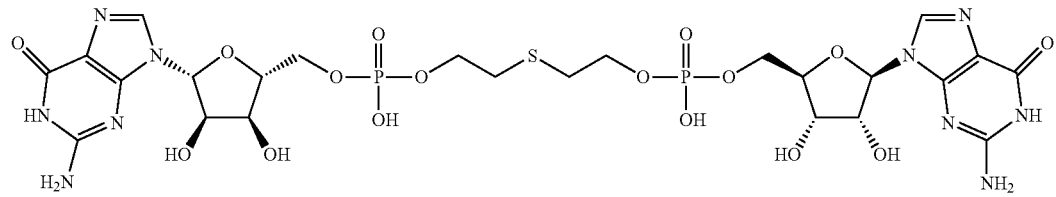 [SMILES: Nc1nc2c(ncn2[C@@H]2O[C@H](COP(=O)(O)OCCSCCOP(=O)(O)OC[C@H]3O[C@@H](n4cnc5c(=O)[nH]c(N)nc54)[C@H](O)[C@@H]3O)[C@@H](O)[C@H]2O)c(=O)[nH]1]

To a solution containing the product from Step 3 (1.92 mmol) in THF (20 ml) was added tert-butylhydroperoxide (0.7 ml, 3.84 mmol). The resulting reaction mixture was stirred at ambient temperature for 16 hours. DBU (2.9 ml, 19.2 mmol) was added and the reaction was stirred for further 16 hours. The reaction mixture was concentrated under reduced pressure and taken up in 900 ml of water. The product was purified by weak anion exchange chromatography (Sepharose, 0-100% 1M triethylammonium bicarbonate/water).

Step 5:

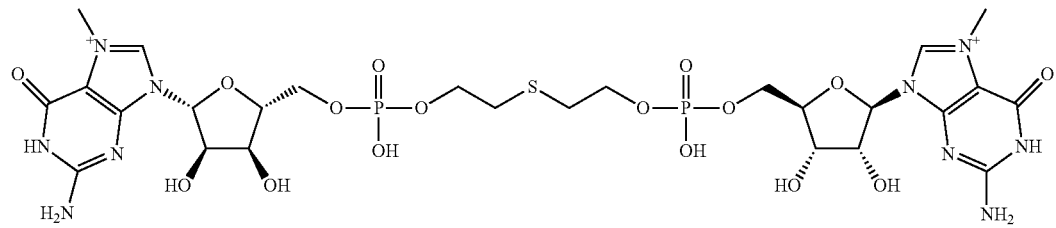 [SMILES: C[n+]1cn([C@@H]2O[C@H](COP(=O)(O)OCCSCCOP(=O)(O)OC[C@H]3O[C@@H](n4c[n+](C)c5c(=O)[nH]c(N)nc54)[C@H](O)[C@@H]3O)[C@@H](O)[C@H]2O)c2nc(N)[nH]c(=O)c21]

This compound was prepared in a manner similar to Step 5 of synthesizing Compound 2.

Compounds 26-29 were synthesized in a manner similar to that described above for Compound 3.

Compounds 26:

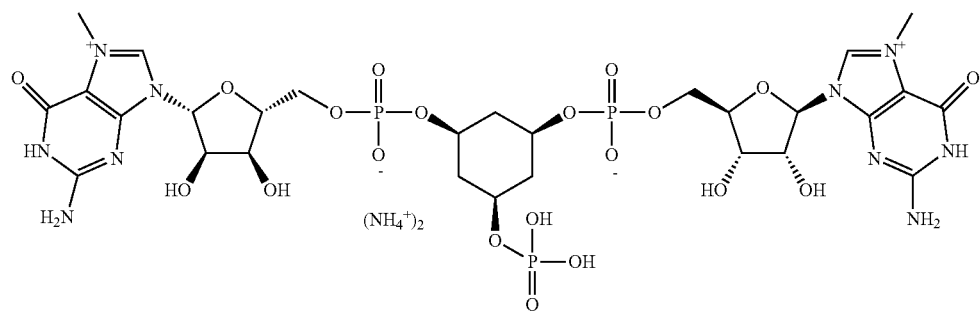 [SMILES: C[n+]1cn([C@@H]2O[C@H](COP(=O)(O)O[C@@H]3C[C@H](OP(=O)(O)O)C[C@H](OP(=O)(O)OC[C@H]4O[C@@H](n5c[n+](C)c6c(=O)[nH]c(N)nc65)[C@H](O)[C@@H]4O)C3)[C@@H](O)[C@H]2O)c2nc(N)[nH]c(=O)c21 ; "(NH4+)2"]

Compounds 27:

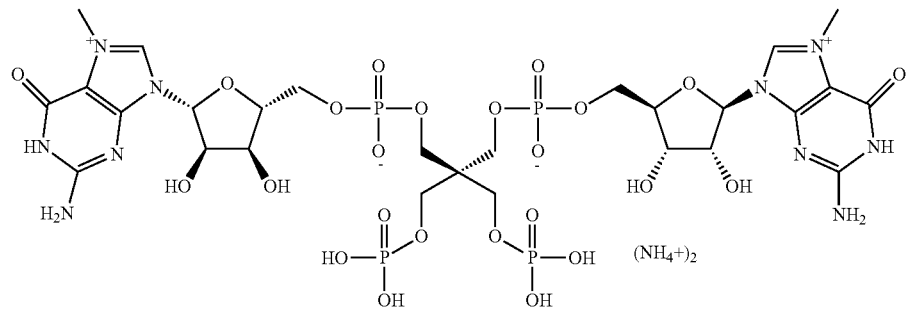

Compounds 28:

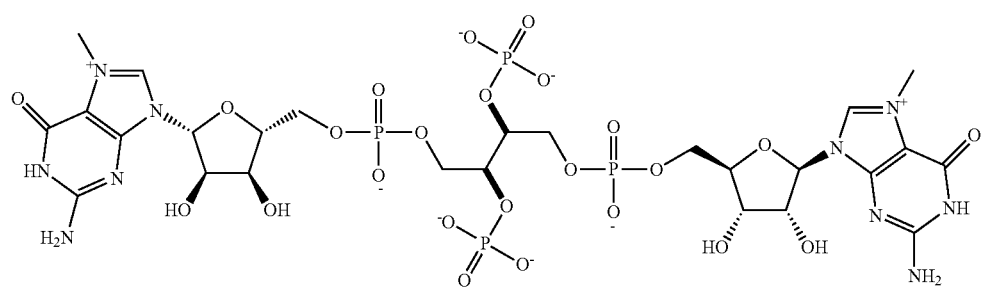

Compounds 29:

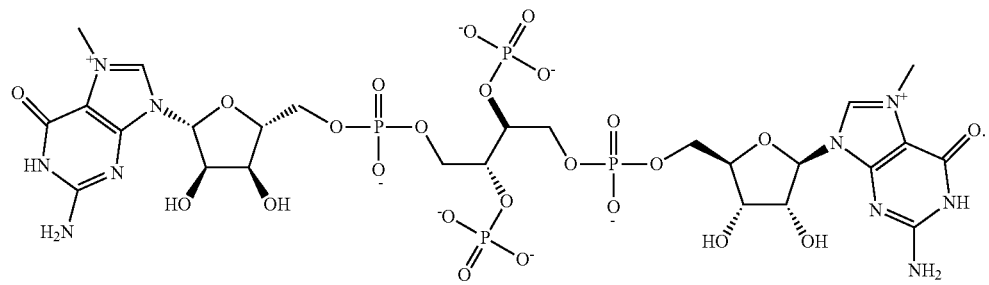

Example 2: Synthesis of mRNAs by In Vitro Transcription (IVT)

The target mRNAs are prepared following IVT Reaction Protocol-Cotranscriptional capping described herein. The materials are described in Table 8.

TABLE 8

| Component | Stock Conc. | Final Conc. | Units |
|---|---|---|---|
| Desired NTPs | 100 | Varied | mM |
| Cap | 100 | Varied | mM |
| 10x Buffer | 10 | 1 | X |
| PPIase | 0.1 | .001 | U/uL |
| T7 RNA Polymerase | 50 | 14 | U/uL |
| Linearized hEPO DNA | Varied | 100 | ng/uL |
| H$_2$O | | | |

1. Ratio of A:U:C:G varies between 1:1:1:0.1 and 1:1:1:1, with the cap added in 10-fold excess to G.
2. T7 RNA polymerase is added after other components except for water.
3. Water is added for a total reaction volume of 100 uL.
4. The mixture is mixed well and spun down in a benchtop centrifuge for 1 minute.
5. The cocktail is incubated at 37 degrees for 4 hours.
6. 2.5 uL of RNase free DNase I is added.
7. The cocktail is incubated at 37° C. for 45 minutes.

As described in this Example, each of A, U, C, and G includes both unmodified and modified NTP. After the IVT reaction is complete, the mixture is cleaned using membrane purification (MegaClear or equivalent), and Oligo dT. Sample concentration is determined using a spectrophotometer, and degradation is quantitated using a bioanalyzer.

Example 3: Binding Affinities to eIF4E Using Surface Plasmon Resonance (SPR)

General Outline of the Assay Procedure

A sensor chip SA (GE Healthcare) is docked into a Biacore 3000 instrument. After washing the surface, protein eIF4E(Elongation Initiation Factor 4E, HNAVIpeptTEVeIF4E 32-217(Biotinylated); pbCPSS1560) is captured non-covalently to the already immobilized streptavidin proteins.

Compound concentration series are injected over the immobilized protein serially in increasing concentration. Interaction models are fitted globally to the experimental traces, enabling determination of $K_d$ or $K_D$ (binding affinity; unit: M) and possibly $k_{on}$ (on-rate, calculated from the association phase; unit: $M^{-1}s^{-1}$) and $k_{off}$ (off-rate, calculated from the dissociation phase; unit: $s^{-1}$).

Methods

Preparation of Sensor Chip

A sensor chip (SAD5001 or SA) was docked into a Biacore 3000 instrument, washed with 50 mM NaOH, 1M NaCl. Protein eIF4E was diluted in running buffer (50 mM HEPES, 150 mM KCl, 10 mM $MgCl_2$, 2 mM TCEP) to ~1 µM. The diluted protein solution was injected for 300-600 seconds. Typical capture levels were 5000-6000 RU.

Test compounds were solubilized in $ddH_2O$ or DMSO to 10 mM. 100 µM stocks were prepared by 100-fold dilution in running buffer (50 mM HEPES, 150 mM KCl, 10 mM $MgCl_2$). Assay was run with or without 1% DMSO.

Data were analyzed in GeneData. Curve fit was accepted or rejected by looking at the resulting sensorgrams and steady state fits.

Assay Validation eIF4E protein was captured according to the above procedure and a set of 7-methyl (m7) guanosine phosphate compounds (m7GMP, m7GDP, m7GTP) as well as a compound with an extra guanosine residue after the tri phosphate chain (m7GTPG) were injected in dose response. Assay has been validated using running buffer with and without DMSO. It was found that surface activity and $K_d$ for m7GTP is not affected by DMSO. It was also found that the surface is extremely stable (continuous use for >6 weeks resulted in 5-10% loss of surface activity). Further, newly captured protein stabilizes slowly, leading to negative responses during the dissociation phase for compounds injected over newly captured protein.

Table 3 below includes the results for certain compounds of the disclosure.

TABLE 3

| Compound No. | $K_d$ (µM) | $k_{off}$ ($s^{-1}$) | τ (s) |
|---|---|---|---|
| Cap0 (i.e., m7GpppG) | 2 | 0.8 | 1.25 |
| 2 | 110 | TBD | |
| 7 | 6.5 | 0.067 | 15 |
| 25 | 300 | TBD | |
| 39 | 45 | TBD | |

Example 4: Kinetic Cell Free In Vitro Translation Assay and Cap Competition Assay The in vitro translation assay was conducted with the HeLa 1-step coupled IVT kit (ThermoFisher Scientific, Waltham, Mass.) according to the manufacturer's instructions to assess performance of new cap analogs as free compounds or as an integral part of capped mRNA. Cap analogs with affinity to eIF4E protein may reduce protein synthesis rate in cell-free translation. Further, RNAs containing such cap analogs ("Cap-modRNA") show different potency of protein synthesis in cell-free translation.

The modified RNAs ("modRNAs") of eGFP and mCitrine-degron, harboring chemical modifications on either the CAP structures, selected ribose units and/or the bases, were diluted in sterile nuclease-free water to a final amount of 500 ng in 5 uL. This volume was added to 20 uL of freshly prepared HeLa Lysate. The in vitro translation reaction was done in a standard 96-well round bottom plate (Corning, Corning, N.Y.), covered with an self-adhesive fluorescence-compatible seal (BioRad, Hercules, Calif.) at 30° C. inside the plate reader Cytation 3 (BioTek, Winooski, Vt.).

The fluorescent signal per reaction increased over time and is considered proportional to the occurring protein synthesis. Each cell-free translation reaction was monitored for 120-180 min with the following settings: eGFP protein—ex. 485 nm, em. 515 nm, gain 80; mCitrine-degron protein—ex. 515, em. 545, gain 70 or 80. The height of the reading head was set to 1 mm above the plate and a reading speed of one per sample every 17 seconds.

For competition assays, the total volume of the cell-free translation reaction was increased to 27.8 uL by addition of either water or diluted free CAP analogs in water. The stock concentration of the free CAP analogs was 1 mM. With two-fold dilutions in water, the concentration was reduced sequentially. After cell-free translation reaction, modRNA (e.g., an m7GpppG(2'-Om) capped mRNA (i.e., a Cap1-tipped mRNA) coding for eGFP) and diluted CAP analogs were combined, the titration curve had a final concentration of 100 uM, 50 uM, 25 uM, 12.5 uM, 6.25 uM, 3.12 uM and 0 uM of free CAP analogs. The CAP analogs used in this study were either commercial products serving as reference material (TriLink, San Diego, Calif.) or compounds disclosed herein. It is hypothesized that the small molecule cap analogs interfere with the assembly of the "closed loop" in a $K_d$-dependent fashion.

After the fluorescent signal in cell-free translation reaction reached a stable plateau, absolute values thereof were transferred to a statistical analysis program (GraphPad Software, La Jolla, Calif.) and curve fitting or $IC_{50}$ calculations were derived with settings according to the instructions of the manufacturer.

The results from the cap competition assay are illustrated in FIG. 1. In this study, the modRNA used comprises 1-methyl-pseudouridine, which replaces each uridine in the RNA sequence and 5-methyl cytidine, which replaces each cytidine in the RNA sequence. Further, Table 4 below includes the $IC_{50}$ values of certain compounds of the disclosure.

TABLE 4

| Compound No. | $IC_{50}$ (µM) | $K_d$ (µM) |
|---|---|---|
| Cap0 (i.e., m7GpppG) | 36 | 2 |
| 7 | 23 | 6.5 |

Cell free translation assays were also conducted using modRNAs comprises 5-methoxy uridine, which replaces each uridine in the RNA sequence, except otherwise specified. The results are shown in Table 5. Table 5 discloses the hEPO levels after 3 hours of a cell-free translation assay.

TABLE 5

| Compound No. | CFT (norm to conc. & capping & cap1) | τ (s) |
|---|---|---|
| 7 | 1.85 | 3.7 |
| Cap1 | 1.00 | 1.3 |
| ARCA | 1.93 | 0.6 |

Example 5: Cell-Based Expression Assay

The cell-based expression assay was conducted following the protocol as described below.

1) Day 1: Seed Hela/Vero/BJ-Fibroblast at 20K cells in 100 uL media/well of a 96 well plate
2) Day 2: Transfection
   Transfect 250 ng/rxn on mCherry/deg mCitrine; 25 ng/rxn on nanoLuc
   Dilute nanoLuc mRNA to 10 ng/uL, in 96 well plates.
   Plate map from Manufacturing (100 ng/uL, per well)

|   |   | 1 | 2 | 3 | 4 | 5 | 6 | 7 | 8 | 9 | 10 | 11 | 12 |
|---|---|---|---|---|---|---|---|---|---|---|---|---|---|
| mcherry | A | M1 | M2 | M3 | M4 | M5 | M6 | M7 | M8 | M9 | M10 | M11 | M12 |
|  | B | M13 | M14 | M15 | M16 | M17 | M18 | M19 | M20 | M21 | M22 | M23 | M24 |
|  | C |  |  |  |  |  |  |  |  |  |  |  |  |
|  | D |  |  |  |  |  |  |  |  |  |  |  |  |
|  | E |  |  |  |  |  |  |  |  |  |  |  |  |
|  | F |  |  |  |  |  |  |  |  |  |  |  |  |
| nanoluc | G | N1 | M2 | M3 | M4 | M5 | M6 | M7 | M8 | M9 | M10 | N11 | N12 |
|  | H | N13 | N14 | N15 | N16 | N17 | N18 | N19 | N20 | N21 | N22 | N23 | N24 |

Make a NanoLuc Dilution Plate (1:10 dil from manufactory, given 10 ng/uL, per well)
Master mix plate map:

|   | 1 | 2 | 3 | 4 | 5 | 6 | 7 | 8 | 9 | 10 | 11 | 12 |
|---|---|---|---|---|---|---|---|---|---|---|---|---|
| A |  |  |  |  |  |  |  |  |  |  |  |  |
| B |  | media | LF2000 | G0 | G1 | G2 | G5 | G0(N21) | G1(N22) | G1(N23) | G5(N24) |  |
| C |  |  |  |  |  |  |  |  |  |  |  |  |
| D |  | B8.1 | B8.2 | B8.3 | B8.4 | B8.5 | B8.6 | B8.7 | B8.8 | B8.9 | B8.10 |  |
| E |  |  |  |  |  |  |  |  |  |  |  |  |
| F |  | B8.11 | B8.12 | B8.13 | B8.14 | B8.15 | B8.16 | B8.17 | B8.18 | B8.19 | B8.20 |  |
| G |  |  |  |  |  |  |  |  |  |  |  |  |
| H |  |  |  |  |  |  |  |  |  |  |  |  |

Make a mCherry/deg mCitrine Master mix plate and a nanoLuc Master mix plate for duplicates, using the layout above.
Stamp out mCherry/deg mCitrine samples directly from manufactory plate. Using the same plate map as NanoLuc.
Destination Plate map (Cell plates):

|   | 1 | 2 | 3 | 4 | 5 | 6 | 7 | 8 | 9 | 10 | 11 | 12 |
|---|---|---|---|---|---|---|---|---|---|---|---|---|
| A |  |  |  |  |  |  |  |  |  |  |  |  |
| B |  | media | LF2000 | G0 | G1 | G2 | G5 | G0(N21) | G1(N22) | G2(N23) | G5(N24) |  |
| C |  | media | LF2000 | G0 | G1 | G2 | G5 | G0(N21) | G1(N22) | G2(N23) | G5(N24) |  |
| D |  | B8.1 | B8.2 | B8.3 | B8.4 | B8.5 | B8.6 | B8.7 | B8.8 | B8.9 | B8.10 |  |
| E |  | B8.1 | B8.2 | B8.3 | B8.4 | B8.5 | B8.6 | B8.7 | B8.8 | B8.9 | B8.10 |  |

-continued

| | | | | | | | | | | |
|---|---|---|---|---|---|---|---|---|---|---|
| F | B8.11 | B8.12 | B8.13 | B8.14 | B8.15 | B8.16 | B8.17 | B8.18 | B8.19 | B8.20 |
| G | B8.11 | B8.12 | B8.13 | B8.14 | B8.15 | B8.16 | B8.17 | B8.18 | B8.19 | B8.20 |
| H | | | | | | | | | | |

| | 1 RNX | 4 RNX |
|---|---|---|
| mRNA | 2.5 uL | 10 uL |
| Lipo 2K | 0.5 uL | 2 uL |
| Optimem | 17 uL | 68 uL |
| Total | 20 uL | |

Incubate Lipofectamine/Optimem for 15 mins, 70 uL added to each well of master mix plate.

Add 10 uL of mRNA(per well) to 70 uL L2K/Optimem mixture.

Incubate mRNA with L2K/Optimem mixture for another 15 mins.

Add 20 uL of mRNA mixture to each well of CELL PLATE.

3) Day 3: Assay (24 hours for expression; 48 hours for cytokine):

mCherry:
  Wash with 100 uL PBS 1×
  Add 100 uL PBS for reading
  Take read on Synergy:
  Program: Fluorescence Endpoint at Excitation:585, emission:615, Gain: 100

Degron mCitrine
  Wash with 100 uL PBS 1×
  Add 100 uL PBS for reading
  Take reads on Synergy at Excitation:510; emission: 540, Gain:100.

NanoLuc:
  Wash with 100 uL PBS 1×
  Add 100 uL Glo Lysis buffer 1×
  Take reads on Synergy
  Program: Luminescence at Gain 115 (default)

4) Day 4 Assay (IFN-b ASSAY):
  Use VeriKine Human Interferon Beta ELISA Kit (#41410-2, PBL Biosciences)
  Follow the protocol of the kit.

The results from the cell-based expression assays in human primary hepatocytes are listed in Table 6. In this study, each of the mRNAs carrying various caps (e.g., Cap1, ARCA or cap analogs disclosed herein) also comprises 5-methoxy uridine, which replaces each uridine in the RNA sequence. Table 6 below shows the normalized expression level using modified mRNAs carrying various caps as compared to mRNA carrying Cap1, in which, mRNA carrying Compound 7 is unmethylated at 2'-OH of the penultimate guanosine (Cap0-like) while all other caps are Cap1-like, i.e., containing the structure of pppG(2'-Om).

TABLE 6

| Compound No. | h-primHeps norm to Capping and Cap1 |
|---|---|
| 7 | 0.22 |
| Cap1 | 1.00 |
| ARCA | 1.52 |

Example 6: In Vivo Expression Assay mRNAs encoding hEPO are synthesized according to the method described in Example 2 above, co-transcriptionally incorporating cap analogs of the disclosure. As in the study of Example 5, each of the mRNAs carrying various caps (e.g., Cap1, ARCA, or cap analogs disclosed herein) also comprises 5-methoxy uridine, which replaces each uridine in the RNA sequence. A MC3-based lipid nanoparticle (LNP) formulation of the synthesized mRNA is produced, and is intravenously administered to CD-1 mice (n=3) at a bolus dose of 0.05 mg/kg. The level of hEPO was tested at 6 h, 24 h, or 48 h after injection. Table 7 shows the normalized hEPO levels measured at 6 h after injection, in which, mRNA carrying Compound 7 is unmethylated at 2'-OH of the penultimate guanosine (Cap0-like) while all other caps are Cap1-like, i.e., containing the structure of pppG(2'-Om).

TABLE 7

| Compound No. | capping %/100 | in vivo hEPO normalized to capping and Cap1 |
|---|---|---|
| 7 | 0.68 | 0.17 |
| Cap1 | 1 | 1.00 |
| ARCA | 0.86 | 0.70 |

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. An RNA molecule having a 5' end comprising a compound of formula (III):

(III)

wherein indicates the attachment point of the 5' end to the RNA molecule;

$B_1$ is

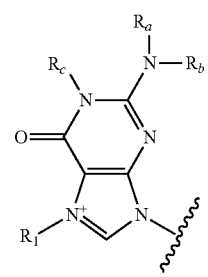

wherein

indicates the attachment point of $B_1$ to the compound;
$R_a$, $R_b$, and $R_c$ are H;
$R_1$ is $CH_3$;
$B_2$ is

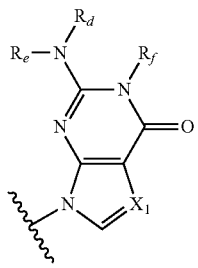

wherein

indicates the attachment point of B₂ to the compound;
$R_d$, $R_e$, and $R_f$ are H;
$X_1$ is N or $N^+(CH_3)$;
$X_2$ is O;
$R_{20}$, $R_{21}$, $R_{22}$, and $R_{23}$ are H;
$R_{27}$ and $R_{28}$ are OH;
$R_2$ is $OR_3$;
$R_3$ is H or $CH_3$; and
$Y_2$ is

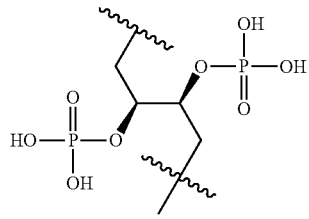 [SMILES: *C[C@H](OP(=O)(O)O)[C@H](C*)OP(=O)(O)O]

wherein

indicates the attachment points of $Y_2$ to the compound.

2. The RNA molecule of claim 1, wherein $X_1$ is N.

3. The RNA molecule of claim 1, wherein $R_3$ is $CH_3$.

4. The RNA molecule of claim 1, wherein $X_1$ is $N^+(CH_3)$.

5. The RNA molecule of claim 1, wherein $R_3$ is H.

6. The RNA molecule of claim 1, wherein $R_3$ is H and $X_1$ is N.

7. The RNA molecule of claim 1, wherein $R_3$ is H and $X_1$ is $N^+(CH_3)$.

8. The RNA molecule of claim 1, wherein $R_3$ is $CH_3$ and $X_1$ is $N^+(CH_3)$.

9. The RNA molecule of claim 1, having a 5' end comprising wherein

indicates the attachment point of the 5' end to the RNA molecule.

10. The RNA molecule of claim 9, wherein $X_1$ is N.

11. The RNA molecule of claim 9, wherein $R_3$ is $CH_3$.

12. The RNA molecule of claim 9, wherein $X_1$ is $N^+(CH_3)$.

13. The RNA molecule of claim 9, wherein $R_3$ is H.

14. The RNA molecule of claim 9, wherein $R_3$ is H and $X_1$ is N.

15. The RNA molecule of claim 9, wherein $R_3$ is H and $X_1$ is $N^+(CH_3)$.

16. The RNA molecule of claim 9, wherein $R_3$ is $CH_3$ and $X_1$ is $N^+(CH_3)$.

17. The RNA molecule of claim 9, wherein the RNA molecule has a half-life that is at least 1.2 times of that of an RNA molecule of the same polynucleotide sequence having a 5' end comprising a natural triphosphate terminal RNA cap in a cellular environment.

18. The RNA molecule of claim 1, having a 5' end comprising

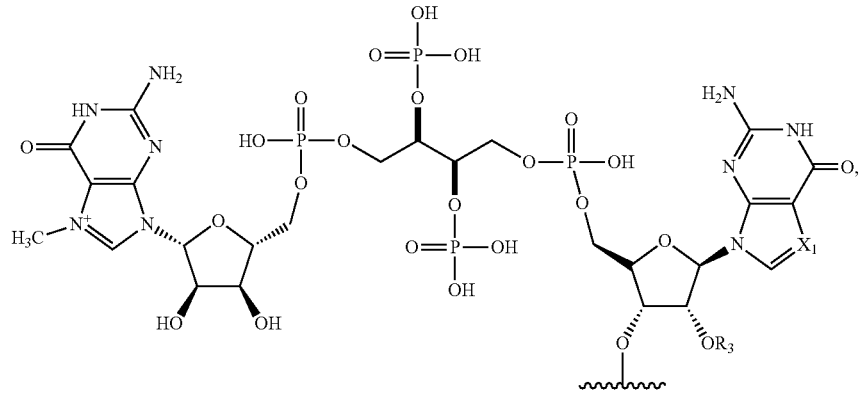

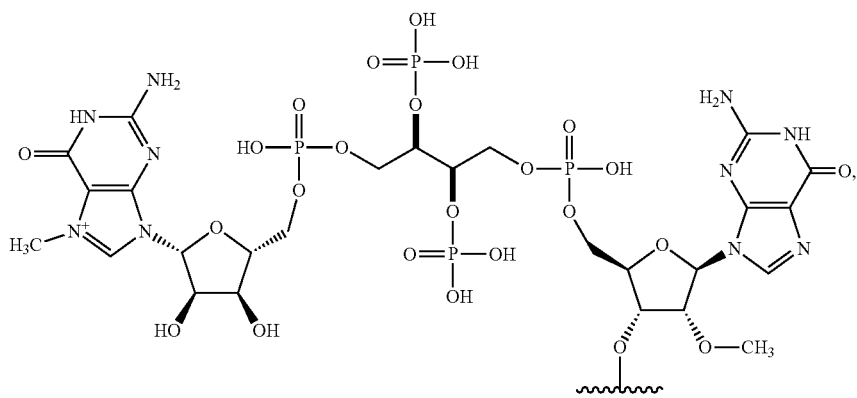 [SMILES: *O[C@H]1[C@@H](OC)[C@H](n2cnc3c(=O)[nH]c(N)nc32)O[C@@H]1COP(=O)(O)OC[C@@H](OP(=O)(O)O)[C@@H](COP(=O)(O)OC[C@H]1O[C@@H](n2c[n+](C)c3c(=O)[nH]c(N)nc32)[C@H](O)[C@@H]1O)OP(=O)(O)O]

wherein

indicates the attachment point of the 5' end to the RNA molecule.

19. The RNA molecule of claim 18, wherein the RNA molecule has a half-life that is at least 1.2 times of that of an RNA molecule of the same polynucleotide sequence having a 5' end comprising a natural triphosphate terminal RNA cap in a cellular environment.

20. The RNA molecule of claim 1, wherein the RNA molecule has a half-life that is at least 1.2 times of that of an RNA molecule of the same polynucleotide sequence having a 5' end comprising a natural triphosphate terminal RNA cap in a cellular environment.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 1
caaaggctct tttcagagcc acca                24

<210> SEQ ID NO 2
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 2
caaaggcucu uuucagagcc acca                24